(12) United States Patent
Lai et al.

(10) Patent No.: US 10,793,623 B2
(45) Date of Patent: Oct. 6, 2020

(54) OPTIMIZED CROSSLINKERS FOR TRAPPING A TARGET ON A SUBSTRATE

(71) Applicant: The University of North Carolina at Chapel Hill, Chapel Hill, NC (US)

(72) Inventors: Samuel Lai, Carrboro, NC (US); M. Gregory Forest, Chapel Hill, NC (US); Christine Henry, Chapel Hill, NC (US); Timothy Wessler, Durham, NC (US); Alexander Chen, Glenville, NY (US); Jennifer Schiller, Chapel Hill, NC (US); Jay Newby, Carrboro, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 15/977,432

(22) Filed: May 11, 2018

(65) Prior Publication Data
US 2018/0258160 A1   Sep. 13, 2018

Related U.S. Application Data

(63) Continuation-in-part of application No. PCT/US2016/061574, filed on Nov. 11, 2016.

(60) Provisional application No. 62/254,856, filed on Nov. 13, 2015.

(51) Int. Cl.
| | |
|---|---|
| *C07K 16/18* | (2006.01) |
| *C07K 16/12* | (2006.01) |
| *G01N 33/557* | (2006.01) |
| *G01N 33/68* | (2006.01) |
| *C07K 16/44* | (2006.01) |
| *G01N 33/569* | (2006.01) |
| *G01N 33/543* | (2006.01) |
| *A61P 31/00* | (2006.01) |
| *C07K 16/08* | (2006.01) |
| *C07K 16/10* | (2006.01) |
| *A61K 38/00* | (2006.01) |

(52) U.S. Cl.
CPC .......... *C07K 16/1235* (2013.01); *A61P 31/00* (2018.01); *C07K 16/087* (2013.01); *C07K 16/1045* (2013.01); *C07K 16/44* (2013.01); *G01N 33/54346* (2013.01); *G01N 33/557* (2013.01); *G01N 33/56983* (2013.01); *G01N 33/6854* (2013.01); *A61K 38/00* (2013.01); *C07K 2317/41* (2013.01); *G01N 2333/16* (2013.01); *G01N 2333/4725* (2013.01)

(58) Field of Classification Search
None
See application file for complete search history.

(56) References Cited

U.S. PATENT DOCUMENTS

2015/0284451 A1* 10/2015 Lai ..................... C07K 16/087
424/133.1

FOREIGN PATENT DOCUMENTS

| WO | 2006/135309 A2 | 12/2006 |
| WO | 2012/078877 A2 | 6/2012 |
| WO | 2014/070786 A1 | 5/2014 |

OTHER PUBLICATIONS

Fahrbach et al (PLoS ONE 8(10): e76176. Oct. 2013).*
Chen et at. "Transient Antibody-Mucin interactions Produce a Dynamic Molecular Shield against Viral Invasion", Biophysical Journal 106:2025-2036 (2014).
Cosio et al. "Binding of human fibronectin to antigen-antibody complexes" J Lab Clin Med. 107(5):453-458 (1986).
Notification of Transmittal of the International Search Report and the Written Opinion of the International Searching Authority, or the Declaration corresponding to International Application No. PCT/US2016/061574 dated Feb. 27, 2017.
Notification Concerning Transmittal of International Preliminary Report on Patentability corresponding to International Application No. PCT/US2016/061574 dated May 24, 2018.

* cited by examiner

*Primary Examiner* — Jennifer E Graser
(74) *Attorney, Agent, or Firm* — Myers Bigel, P.A.

(57) ABSTRACT

The presently-disclosed subject matter relates to crosslinkers, compositions, and methods for trapping a target of interest on a substrate of interest. The methods may be used to inhibit and treat pathogen infection and provide contraception. The methods may be used to trap or separate particles and other substances. The subject matter further relates to methods of identifying and preparing optimal crosslinkers and methods for manipulating targets of interest.

17 Claims, 36 Drawing Sheets

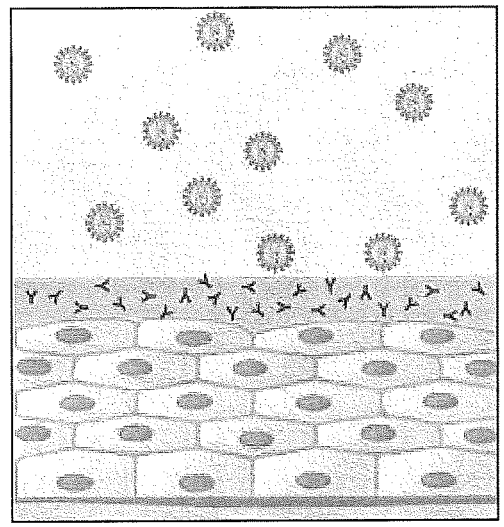
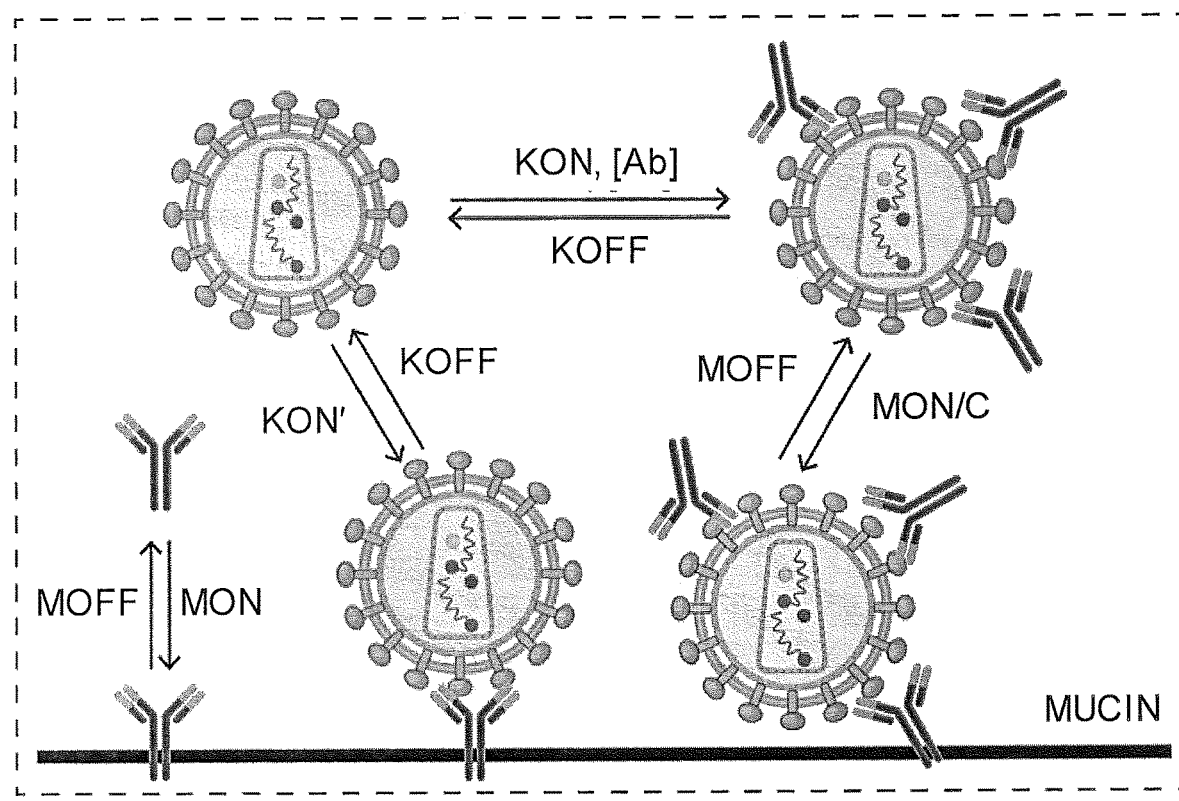
FIG. 1

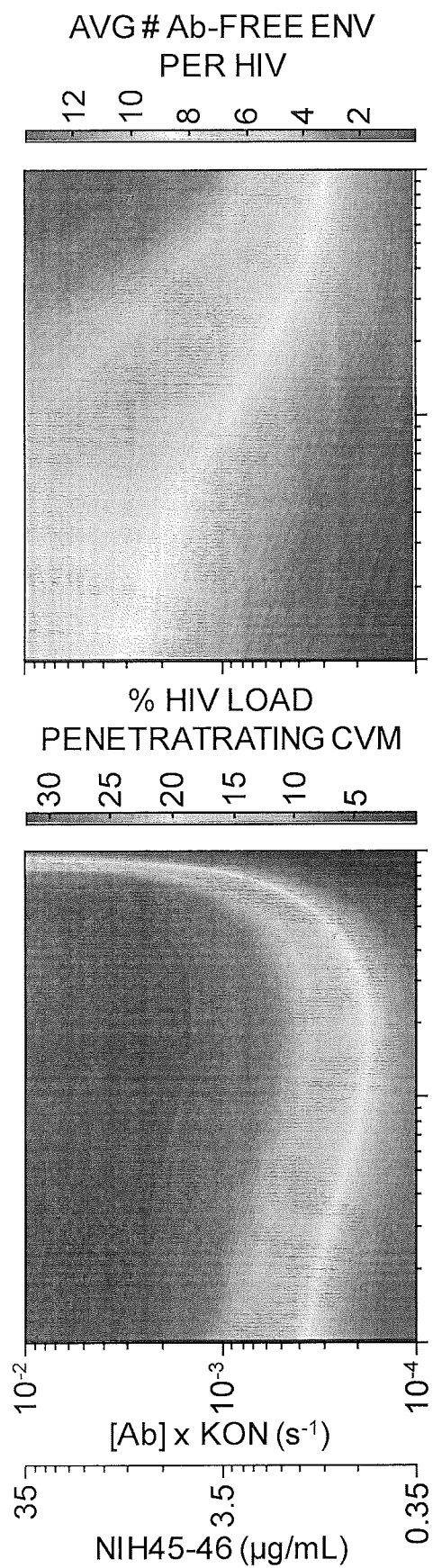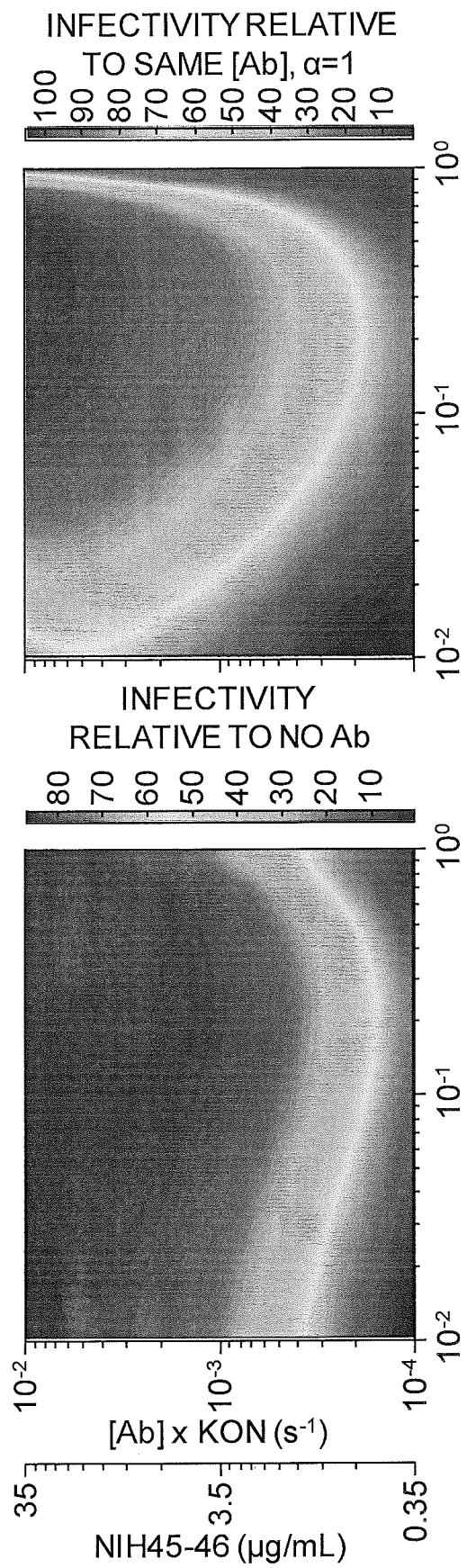

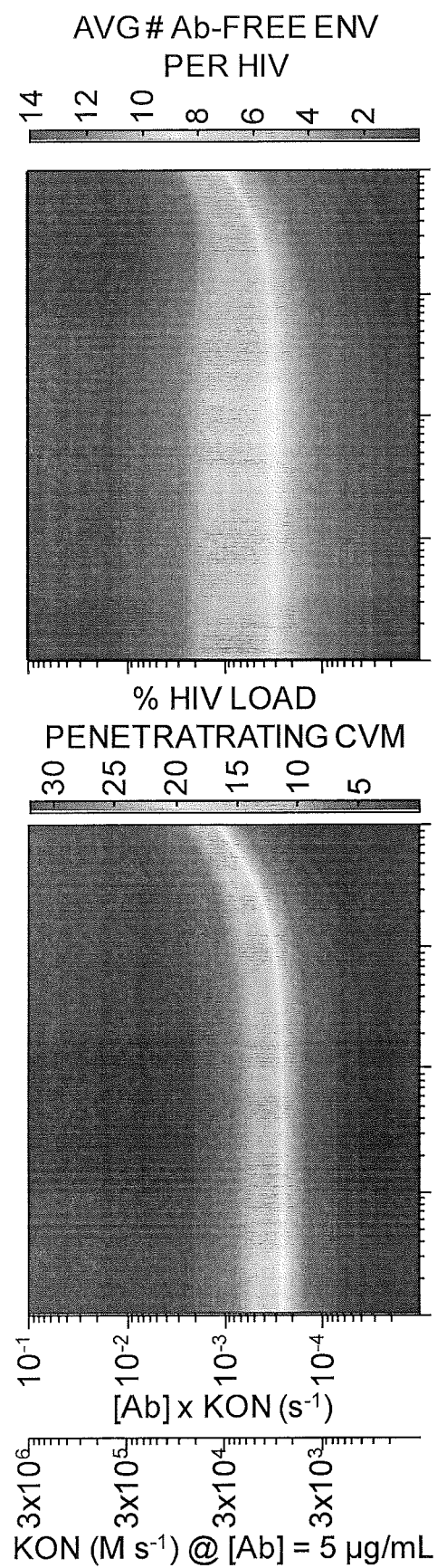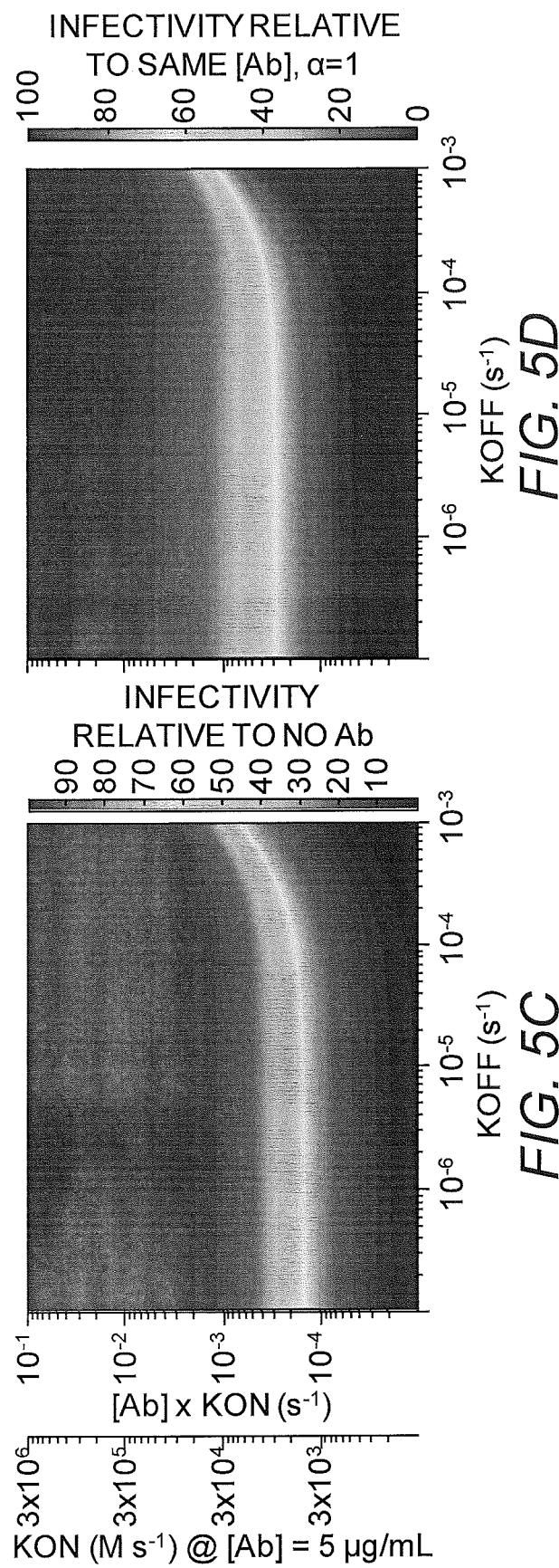

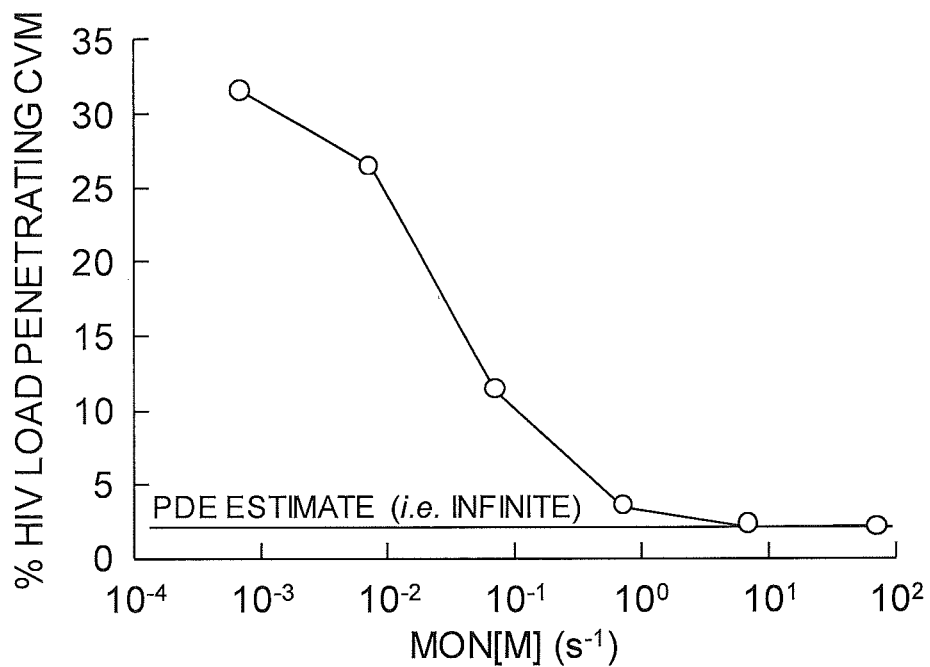
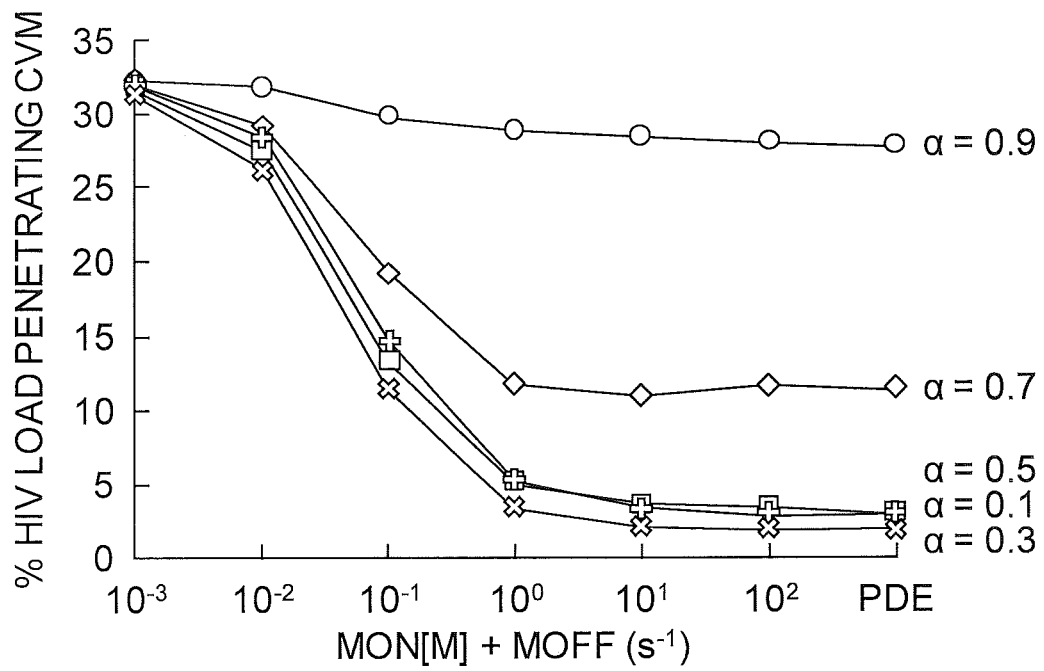
FIG. 7

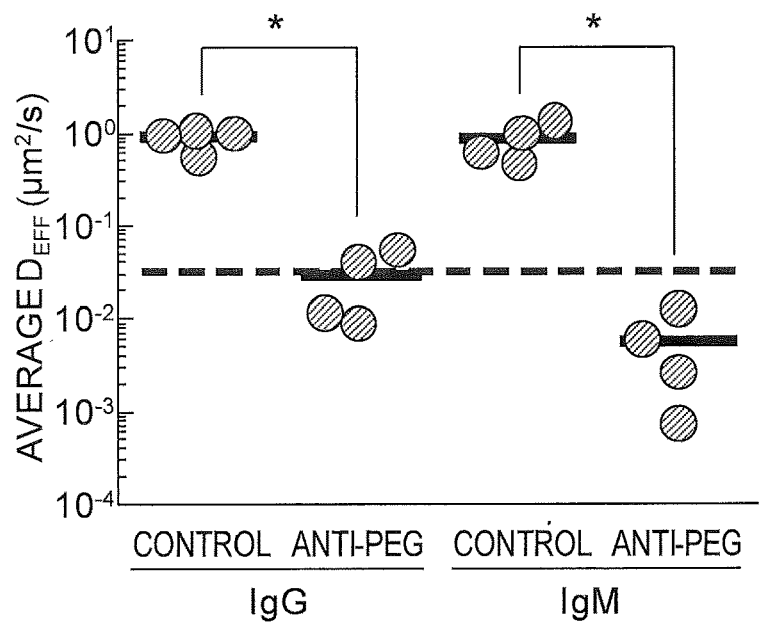
FIG. 9D
+ CONTROL Ab
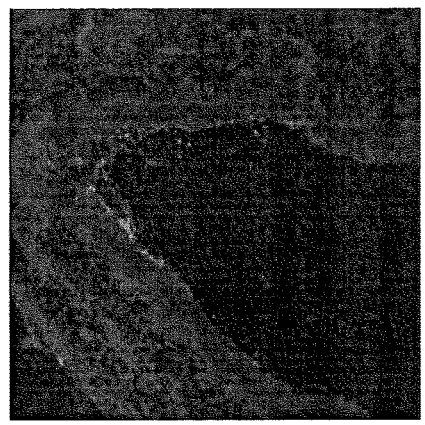
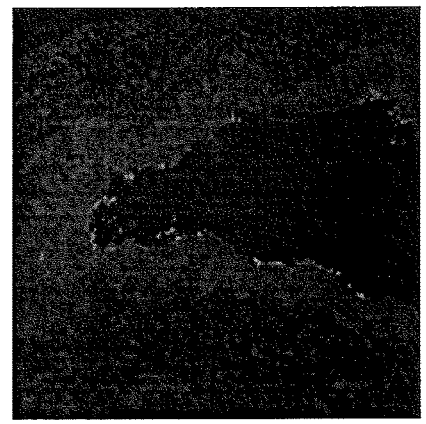
+ ANTI-PEG Ab
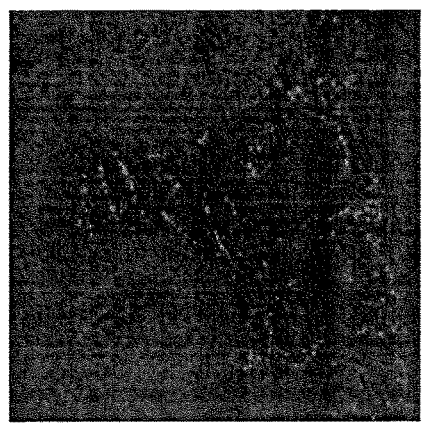
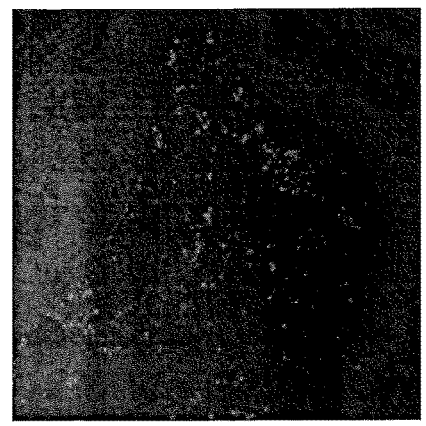
FIG. 10

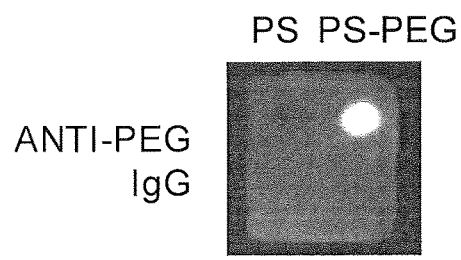
FIG. 12A
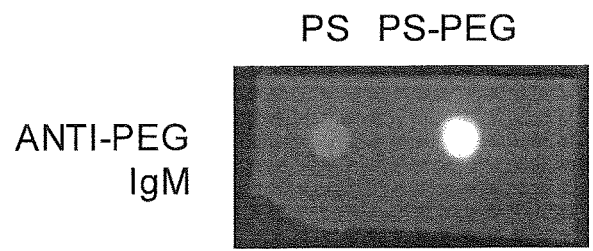
FIG. 12B
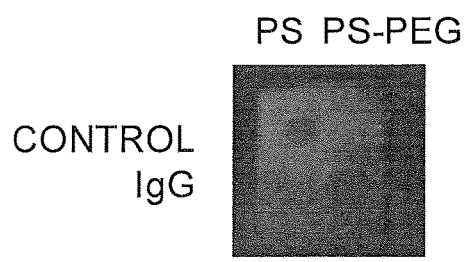
FIG. 12C
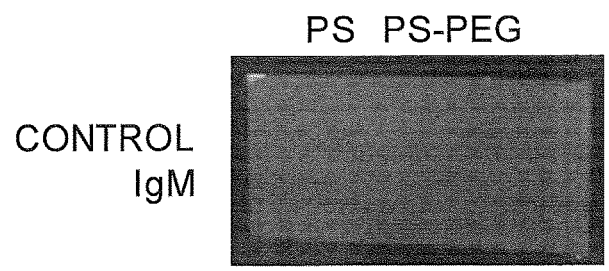
FIG. 12D
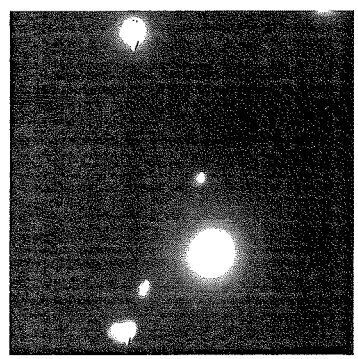
FIG. 13A
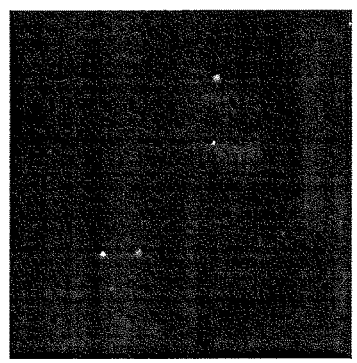
FIG. 13B
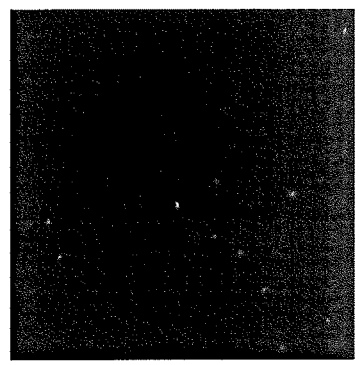
FIG. 13C
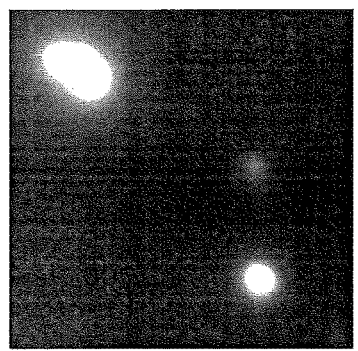
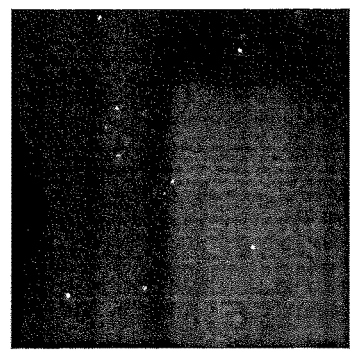
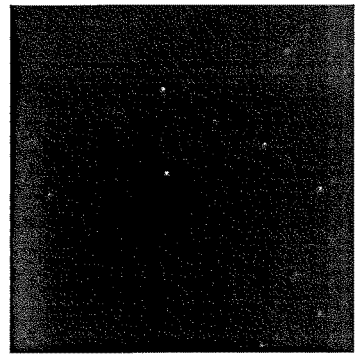

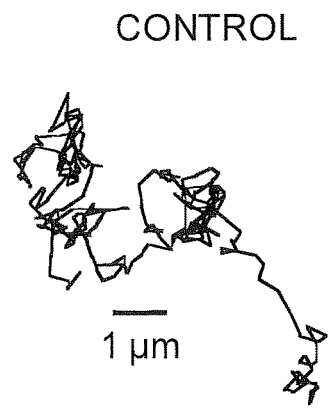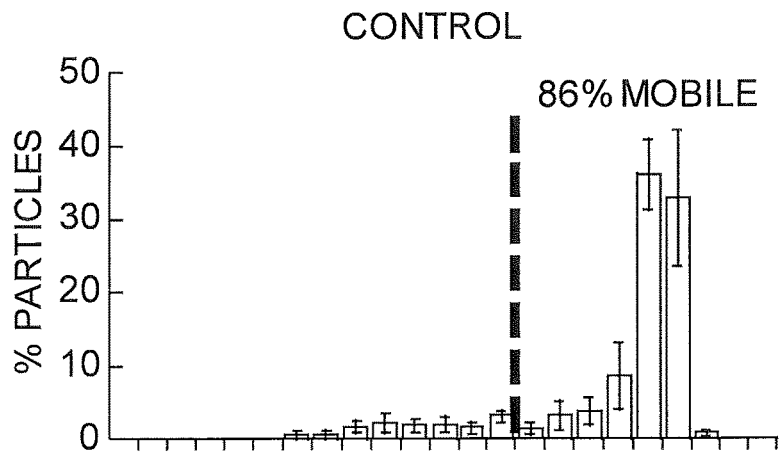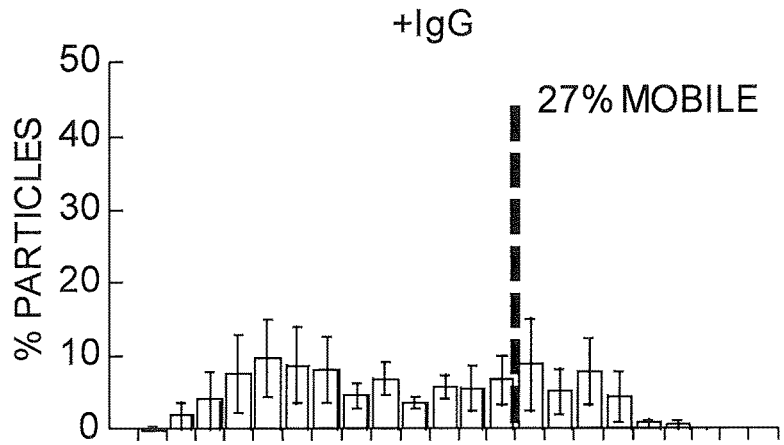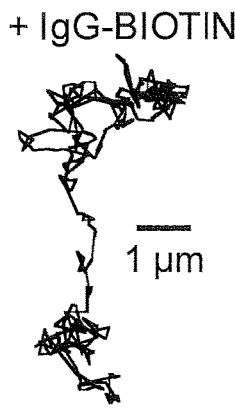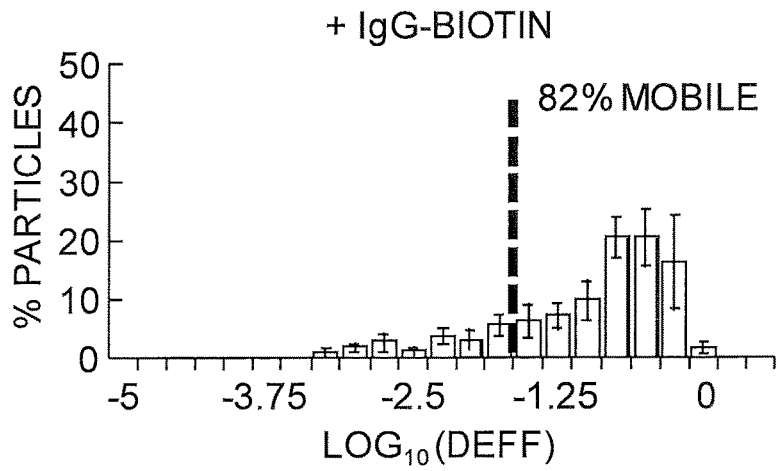
FIG. 14A
FIG. 14B

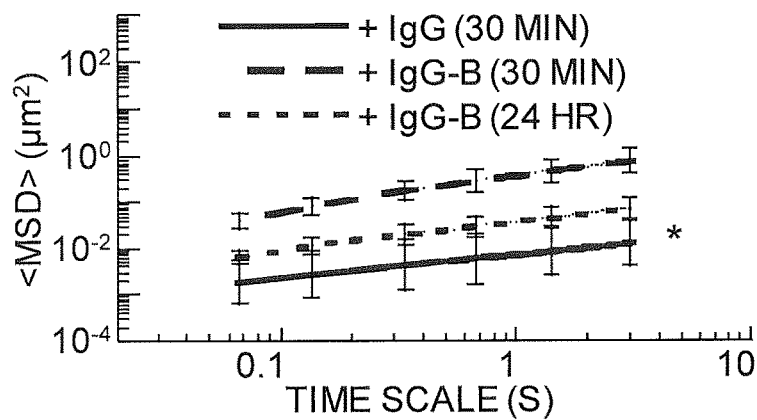
FIG. 16A
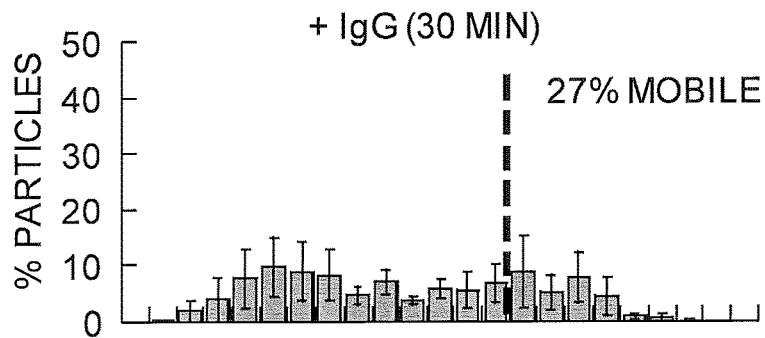
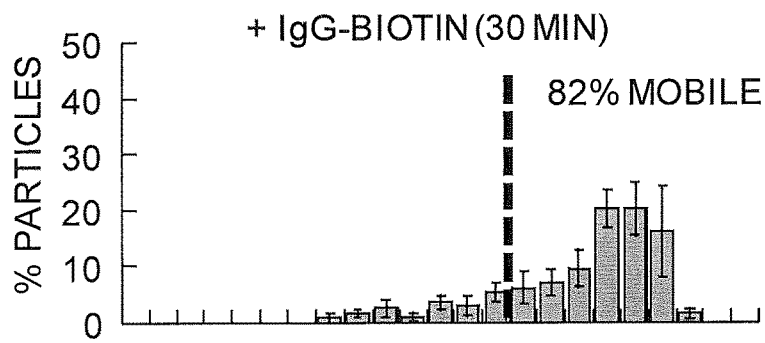
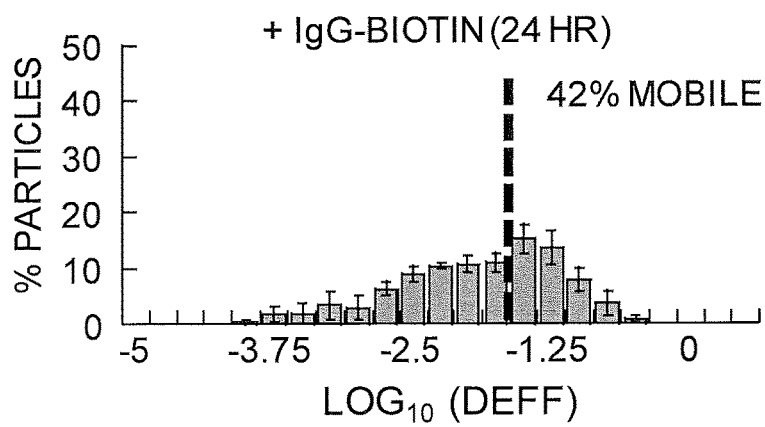
FIG. 16B

IgG-HEAVY CHAIN, 53 KDa

NATIVE    DEGLYCOSYLATED

IgM-HEAVY CHAIN, 70 KDa

NATIVE    DEGLYCOSYLATED

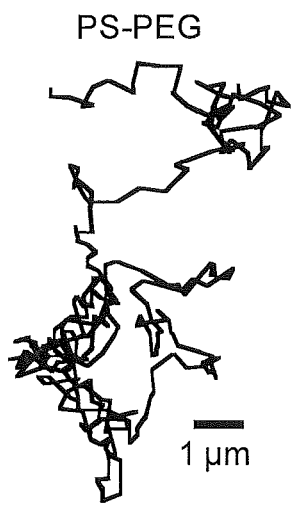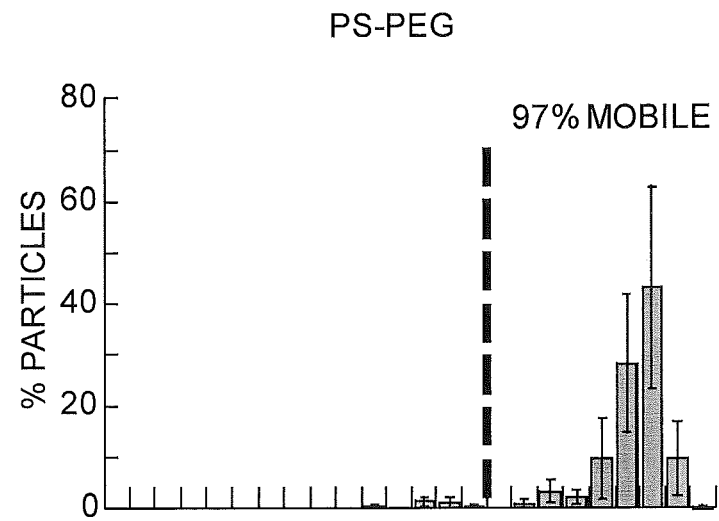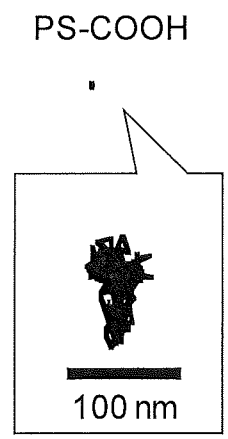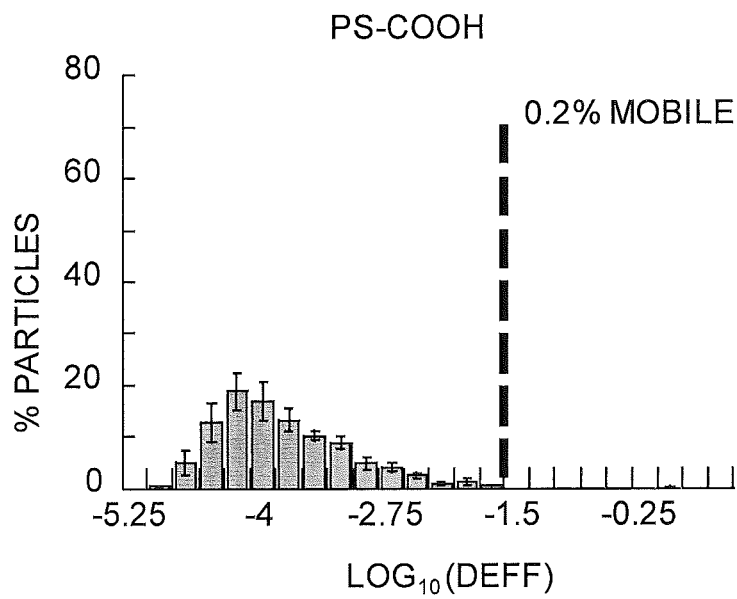
FIG. 23A                FIG. 23B

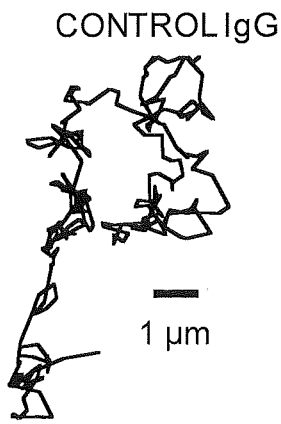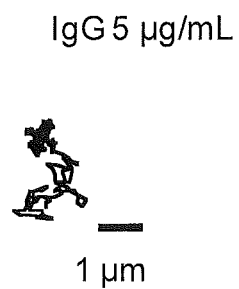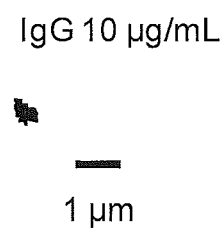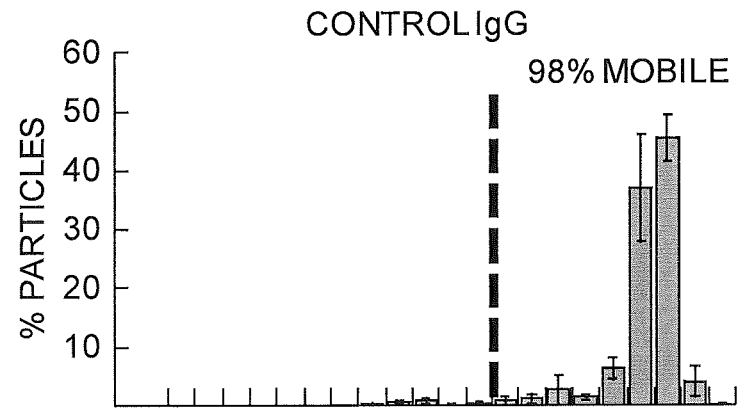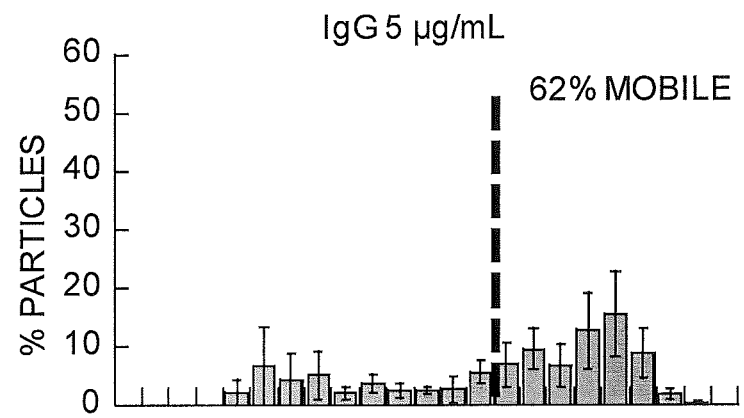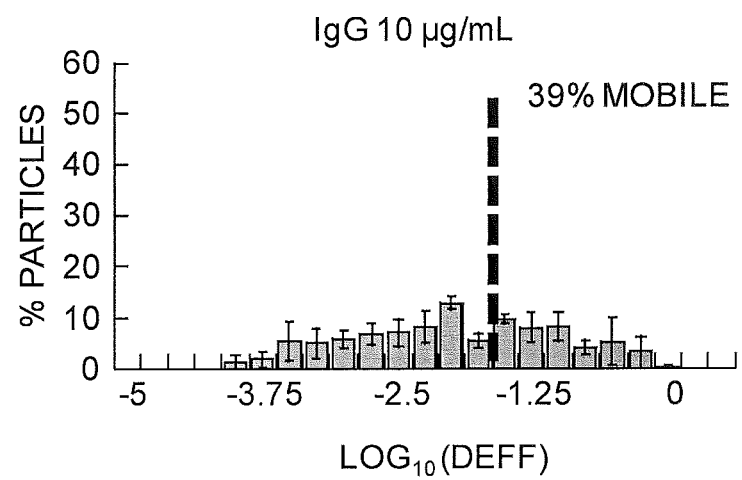
*FIG. 24A*  *FIG. 24B*

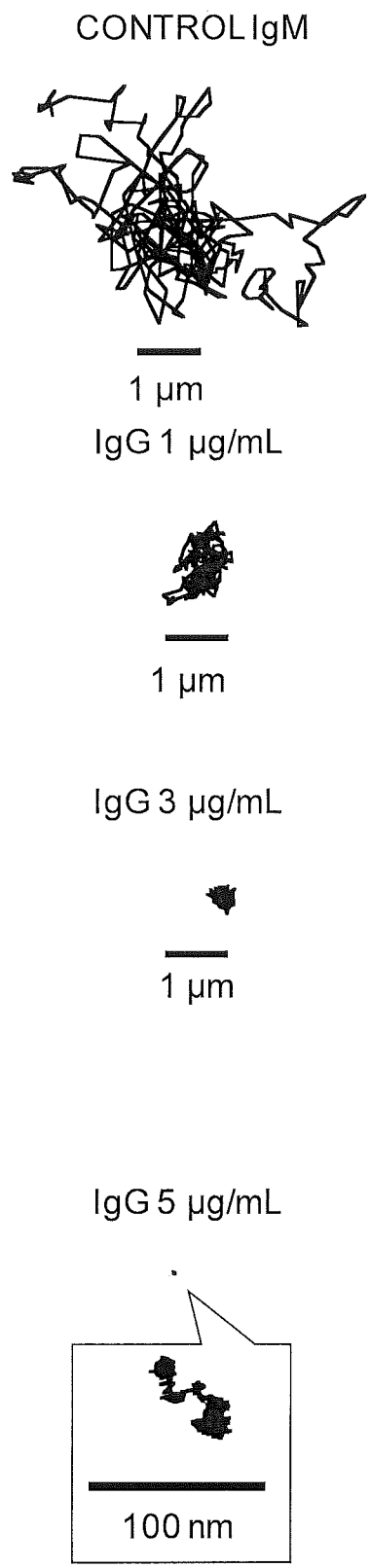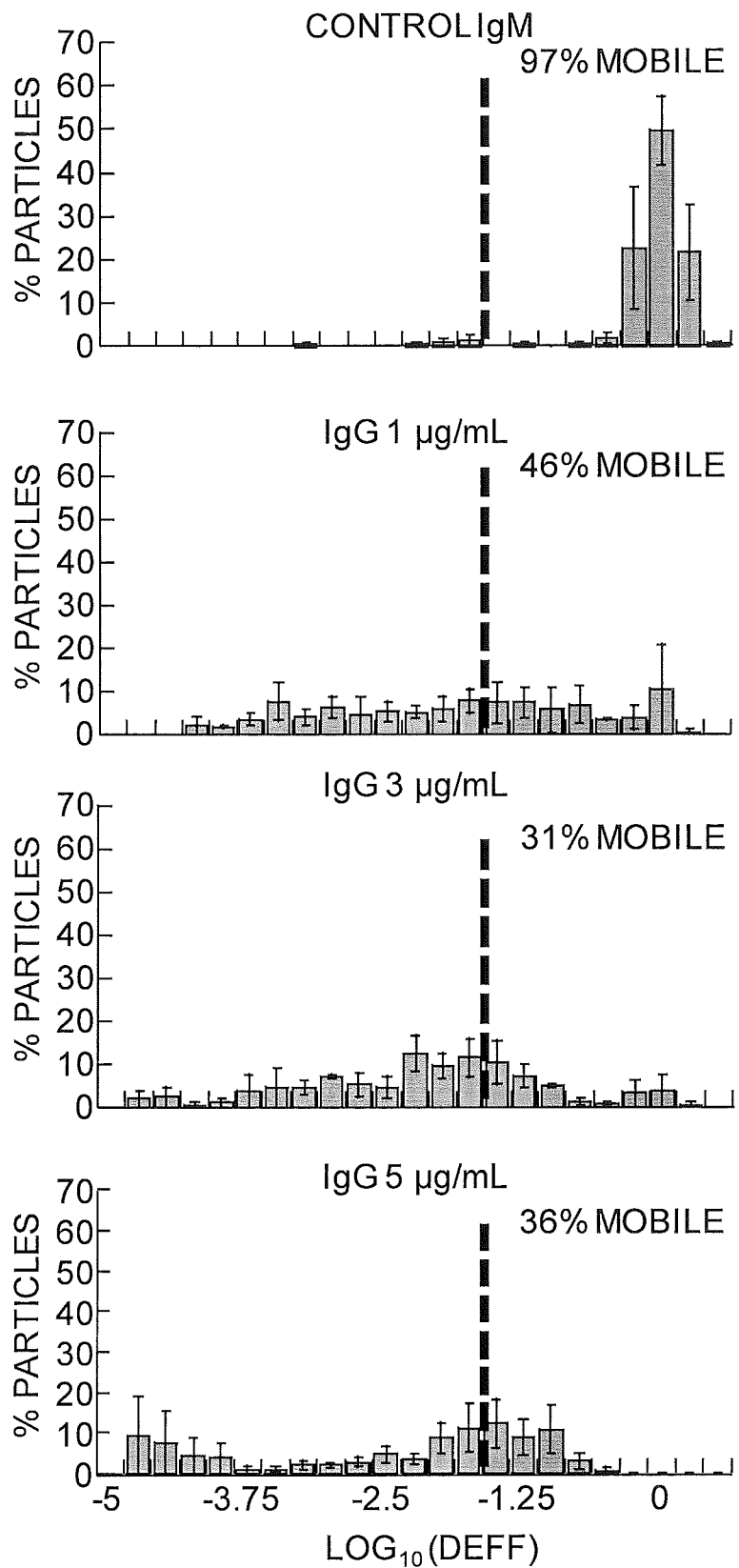
FIG. 25A
FIG. 25B

OPTIMIZED CROSSLINKERS FOR TRAPPING A TARGET ON A SUBSTRATE

STATEMENT OF PRIORITY

This application is a continuation-in-part of PCT Application No. PCT/US2016/061574, filed Nov. 11, 2016, which claims the benefit of U.S. Provisional Application Ser. No. 62/254,856, filed Nov. 13, 2015, the entire contents of each of which are incorporated by reference herein.

GOVERNMENT INTEREST

This invention was made with government support under Grant Numbers R21EB017938 and U19AI096398 awarded by the National Institutes of Health and Grant Number DMR-1151477 awarded by the National Science Foundation. The government has certain rights in the invention.

FIELD OF THE INVENTION

The presently-disclosed subject matter relates to crosslinkers, compositions, and methods for trapping a target of interest on a substrate of interest. The methods may be used to inhibit and treat pathogen infection and provide contraception. The methods may be used to trap or separate particles and other substances. The subject matter further relates to methods of identifying and preparing optimal crosslinkers and methods for manipulating targets of interest.

BACKGROUND OF THE INVENTION

Antibodies (Ab) produced by our immune system are found in abundant quantities in both blood and mucosal secretions, and serve as key messenger molecules that help regulate numerous complex defense mechanisms against foreign pathogens (Casadevall et al., *Nat. Immunol.* 13:21 (2012); Corthesy, *Future Microbiol.* 5:817 (2010); Kozlowski et al., *Curr. Mol. Med.* 3:217 (2003)). For example, Ab can directly block contact between viruses and target cells, a process known as neutralization (Burton et al., *Nat. Immunol.* 16:571 (2015); van Gils et al., *Virology* 435:46 (2013)). Ab can also facilitate other protective functions, such as ingestion and destruction of the pathogens (opsonization) or infected cells (antibody-dependent cellular cytotoxicity, or ADCC) by specialized immune cells, as well as activation of a cascade of enzymes that lead to direct lysis of the pathogen membrane (complement) (Dunkelberger et al., *Cell Res.* 20:34 (2010); Huber et al., Olson W C, Trkola A (2008) Antibodies for HIV treatment and prevention: window of opportunity? Curr. *Top. Microbiol. Immunol.* 317:39 (2008); Kilian et al., Function of mucosal immunoglobulins. In: Ogra et al., editors. Handbook of Mucosal Immunology. San Diego: Academic Press. pp. 127-137 (1994)). These various protective mechanisms most certainly contribute in part to the robust protection observed with topically delivered antibody against mucosally transmitted infections in a multitude of animal studies (Whaley et al., *J Infect. Dis.* 169:647 (1994); Zeitlin et al., *Virology* 225:213 (1996); Veazey et al., *Nat. Med.* 9:343 (2003); Mascola et al., *Nat. Med.* 6:207 (2000)).

In the female reproductive tract, IgG is the predominant Ab secreted into cervicovaginal mucus (CVM) coating the female reproductive tract (Chipperfield et al., *Infect. Immun.* 11:215 (1975); Usala et al., *J Reprod. Med.* 34:292 (1989); Wang et al., *Mucosal Immunol.* 7:1036 (2014)). We have recently shown that IgG can facilitate an alternative mechanism of immune protection based on trapping viruses in CVM (Wang et al., *Mucosal Immunol.* 7:1036 (2014)). Interestingly, since the diffusivity of IgG in mucus is only slowed ~10-20% compared to in buffer (Saltzman et al., *Biophys. J.* 66:508 (1994); Olmsted et al., *Biophys. J* 81:1930 (2001)), individual IgG appears to possess only weak and transient affinity with mucins, and thus were thought incapable of effectively crosslinking viruses to mucins. Nevertheless, as IgG accumulates on the virus surface, the array of virion-bound IgG can collectively impart to the individual virion multiple weak Ab-mucin bonds, thereby generating sufficient avidity to slow or even immobilize individual virions in mucus akin to a Velcro® patch. Trapping viruses in mucus greatly reduces the flux of virus reaching target cells in the vaginal epithelium, and trapped viruses are eliminated along with natural mucus clearance mechanisms, as evident by protection against vaginal Herpes transmission using a non-neutralizing monoclonal IgG (Wang et al., *Mucosal Immunol.* 7:1036 (2014)).

Most viruses, including HIV, can quickly penetrate mucus secretions, suggesting that there may be only a limited window of opportunity for Ab to accumulate on the virus surface before they can reach and infect the underlying vaginal epithelium (McKinley et al., *PLoS One* 9:e100598 (2014)) [18]. The extent to which IgG can hinder the diffusion of viruses in mucus, and consequently the potency of protection based on IgG-mediated trapping of viruses, is thus heavily influenced by the tandem effect of IgG-mucin affinity as well as virion-binding kinetics of topically-delivered or vaccine-elicited Ab. IT is desirable to develop more potent 'muco-trapping' IgG, as that can directly reduce the dose of IgG needed for passive immunization of the vagina as well as enhance protection against viruses with limited antigens on the virus surface. Nevertheless, a conundrum quickly arises: although fewer number of virus-bound IgG is needed to trap a virus if individual IgG possesses increased affinity to mucins, the greater affinity to mucins would also directly reduce the diffusional freedom of any mucin-bound IgG and thus limits the rates with which the IgG can bind to antigens on the virus surface. The exact IgG-mucin affinity and IgG-antigen binding kinetics that maximizes viral trapping and protection likely depend on specific characteristics of the virus, such as its size and surface antigen density, and empirical determination of both parameters experimentally is undoubtedly challenging.

There is a need in the art for new compositions comprising optimized Ab, and methods of using such compositions, to prevent and treat infectious diseases and provide contraception, as well as to manipulate targets by trapping on a substrate.

SUMMARY OF THE INVENTION

To better understand the subtle yet significant interplay between the various kinetic and diffusive processes associated with CVM laden with IgG with distinct mucin affinities, the introduction of virus-laden semen and subsequent unfolding of events, a mathematical model was developed whereby the kinetic and diffusion constants of both IgG and viruses can be freely tuned. As a proof-of-concept, a focus on HIV was chosen, given the sore need for alternative strategies to prevent vaginal HIV transmission; indeed, passive immunization has recently garnered attention as a promising approach for HIV prophylaxis (Klein et al., *Science* 341:1199 (2013); Whaley et al., *J. Infect. Dis.* 210 Suppl 3:S674 (2014)). The model described here allows one to simulate the diffusion of HIV from seminal secretions through CVM containing neutralizing IgG against HIV immediately after ejaculation, with IgG concentration, IgG-antigen binding kinetics and IgG-mucin affinity as tunable model parameters (FIG. 1). This allows one to explore quantitatively whether tuning IgG-mucin affinity can facilitate improved protection against vaginal HIV infection.

Development and validation of the mathematical model has allowed optimization of antibodies and other crosslinkers that can be used for preventing and treating infection, monitoring the effectiveness of vaccines, providing contraception, as well as the purification and manipulation of target molecules.

Thus, one aspect of the invention relates to a method of selecting a crosslinker for trapping a target of interest on a substrate of interest, comprising:

(a) determining an optimal target binding affinity and substrate binding affinity for the target of interest and the substrate of interest using a mathematical model;

(b) measuring the target binding affinity and substrate binding affinity of one or more crosslinkers; and (c) selecting a crosslinker that substantially matches the optimal target binding affinity and substrate binding affinity determined in step (a).

A further aspect of the invention relates to a method of selecting a crosslinker for trapping a target of interest on a substrate of interest, comprising:

(a) determining an optimal target binding affinity and substrate binding affinity for the target of interest and the substrate of interest using a mathematical model;

(b) altering the target binding affinity and/or substrate binding affinity of one or more crosslinkers;

(c) measuring the target binding affinity and substrate binding affinity of the one or more altered crosslinkers; and (d) selecting an altered crosslinker that substantially matches the optimal target binding affinity and substrate binding affinity determined in step (a).

Another aspect of the invention relates to a method of selecting a crosslinker for trapping a target of interest on a substrate of interest, comprising:

(a) measuring the target binding affinity and substrate binding affinity of one or more crosslinkers; and (b) selecting a crosslinker that substantially matches a predetermined optimal target binding affinity and substrate binding affinity.

An additional aspect of the invention relates to a method of selecting a crosslinker suitable for trapping a target of interest on a substrate of interest, comprising:

(a) altering the target binding affinity and/or substrate binding affinity of one or more crosslinkers;

(b) measuring the target binding affinity and substrate binding affinity of the one or more crosslinkers; and (c) selecting an altered crosslinker that substantially matches a predetermined optimal target binding affinity and substrate binding affinity.

In some embodiments, the target is a pathogen, a sperm cell, or a particle. In some embodiments, the substrate is a biopolymer. In some embodiments, the crosslinker is an antibody or an antibody fragment or derivative.

A further aspect of the invention relates to a crosslinker identified by the methods of the invention.

Another aspect of the invention relates to a crosslinker for trapping a target of interest on a substrate of interest, wherein the crosslinker associates with the substrate of interest at least about 10% of the time but less than 99.9% of the time, and has a rate of binding to the target of interest greater than about $10^4$ $M^{-1}$ $s^{-1}$.

For example, described herein are methods for trapping a foreign substance (e.g., a pathogen) in mucus containing mucins, said method comprising contacting the foreign substance (e.g., the pathogen) with an antibody in an amount effective to trap the foreign substance (e.g., the pathogen) in mucus, wherein the antibody associates with the mucins about 20% to less than 99% of the time (e.g., about 25% to 95%, about 25% to 90%, about 25% to 85%, about 30% to 85%, etc.), has a rate of binding to the foreign substance such as pathogen greater than about $1\times10^4$ $M^{-1}$ $s^{-1}$, and has a diffusion coefficient about 20% to 99% (e.g., about 25% to 95%, about 25% to 90%, about 25% to 85%, about 30% to 85%, etc.), less compared to the diffusion coefficient of the antibody in water.

For example, the antibody may associate with the mucins about 75% of the time (e.g., between 30% and 85% of the time). As described in greater detail herein, antibodies having a biding affinity of less than $1\times10^4$ $M^{-1}$ $s^{-1}$, and that associate with the mucins outside of this range (e.g., greater than 85-95% of the time, less than 25-30% of the time) may not be effective.

As described in greater detail herein, the crosslinker may be an antibody or portion of an antibody. Although any appropriate antibody (e.g., IgG, IgM) may be used, in some variations, the antibody is an IgG antibody or a fragment or derivative thereof. In some variations, the antibody is an IgM antibody or a fragment or derivative thereof The antibody may bind to a non-neutralizing epitope on the pathogen; alternatively, in some variations, the antibody binds to a neutralizing epitope on the pathogen.

The antibody may have a trapping potency at a sub-neutralization dose.

The antibody may be formulated into a composition suitable for delivering to a mucosal surface. For example, the antibody may be formulated as a topical composition (e.g., an aerosol or the like). The composition may be formulated as a composition suitable for oral administration. The composition may further comprise a second antibody. The second antibody may be directed to a second epitope of the same or a different epitope.

A method for trapping a foreign substance (e.g., a pathogen) in mucus containing mucins may include: administering to a subject an effective amount of an antibody to trap the foreign substance such as the pathogen in mucus, wherein the antibody associates with the mucins about 20% to less than 99% of the time (e.g., between 30%-85% of the time, between about 25% to 95%, between about 25% to 90%, between about 25% to 85%, between about 30% to 85%, etc., about 75% of the time, etc.), has a rate of binding to the foreign substance such as the pathogen greater than about $1\times10^4$ $M^{-1}$ $s^{-1}$, and has a diffusion coefficient about 20% to 99% (e.g., about 25% to 95%, about 25% to 90%, about 25% to 85%, about 30% to 85%, etc.), less compared to the diffusion coefficient of the antibody in water.

Also described herein are methods for preventing or treating an infection at a mucosa in a subject (e.g., at one or more of: an oral mucosa, a nasal mucosa, a lung mucosa, a genital mucosa, uterine mucosa, a vaginal mucosa an ocular mucosa and a gastrointestinal mucosa), wherein the infection is caused by a foreign substance (e.g., a pathogen), said method comprising: administering to the subject in need thereof an effective amount of an antibody, wherein the antibody associates with the mucins about 20% to less than 99% of the time (e.g., between about 25% to 95%, between about 25% to 90%, between about 25% to 85%, between about 30% to 85%, etc., of the time, about 75% of the time, etc.), has a rate of binding to the foreign substance such as the pathogen greater than about $1 \times 10^4$ $M^{-1}$ $s^{-1}$, and has a diffusion coefficient about 20% to 99% (e.g., about 25% to 95%, about 25% to 90%, about 25% to 85%, about 30% to 85%, etc.) less compared to the diffusion coefficient of the antibody in water.

Administering may include topically administering the antibody to the mucosa of the subject. The antibody may be formulated into a composition suitable for intranasal, oral, intravaginal, by inhalation, or topical administration to a mucosal surface.

An additional aspect of the invention relates to a composition, pharmaceutical composition, or kit comprising one or more crosslinkers of the invention.

A further aspect of the invention relates to a method of trapping a target of interest on a substrate of interest, the method comprising contacting the target of interest with the crosslinker or composition of the invention in an amount effective to trap the target of interest on the substrate of interest.

Another aspect of the invention relates to a method of inhibiting an infection by a pathogen or a disease or disorder caused by an infection by a pathogen in a subject in need thereof, comprising administering to a mucosa of the subject the crosslinker or composition of the invention in an amount effective to inhibit the infection or the disease or disorder caused by the infection; wherein the crosslinker specifically binds the pathogen.

An additional aspect of the invention relates to a method of treating an infection by a pathogen or a disease or disorder caused by an infection by a pathogen in a subject in need thereof, comprising administering to a mucosa of the subject the crosslinker or composition of the invention in an amount effective to treat the infection or the disease or disorder caused by the infection; wherein the crosslinker specifically binds the pathogen.

A further aspect of the invention relates to a method of providing contraception in a female subject, comprising administering to a mucosa of a reproductive tract of the subject the crosslinker or composition of the invention in an amount effective to provide contraception, wherein the crosslinker specifically binds a sperm cell.

Another aspect of the invention relates to a computer program product comprising: a computer readable storage medium having computer readable code embodied in the medium, the computer code comprising: computer readable code to perform operations to determine an optimal target binding affinity and substrate binding affinity for a target of interest and an substrate of interest using a mathematical model.

An additional aspect of the invention relates to a computer system, comprising: a processor; and a memory coupled to the processor, the memory comprising computer readable program code embodied therein that, when executed by the processor, causes the processor to perform operations to determine an optimal target binding affinity and substrate binding affinity for a target of interest and an substrate of interest using a mathematical model.

In general, the method and compositions described herein are directed to trapping one or more target pathogen on a surface or in a material to inhibit infection by the pathogen. The surface or material may be any one in which pathogens are found, including both natural surfaces/materials (e.g., mucus, extracellular matrix, basement membranes, etc.) and man-made or applied surfaces/materials (e.g., hydrogels). For example, any of the methods described herein may include improving or enhancing trapping of a pathogen in a hydrogel that is applied to a subject as part of a film, bandage, garment, implant, tool, or the like. The hydrogel may be matched to the crosslinker (e.g., antibody) with an affinity for the pathogen(s).

For example, described herein are methods for improving or enhancing the barrier property of a hydrogel against a foreign substance (e.g., a pathogen), said method comprising contacting the foreign substance (e.g., the pathogen) with an IgG or IgM antibody, or a fragment or derivative thereof in an amount effective to immobilize the foreign substance (e.g., the pathogen), wherein the antibody has a binding affinity less than about $10^{-2}$ M (e.g., between about $10^{-9}$ M and about $10^{-7}$ M) with a constituent of the hydrogel. The hydrogel may be a biological hydrogel. The antibody or fragment thereof may therefore bind to both the foreign substance such as the pathogen and to the hydrogel; the binding to the hydrogel may be within a predetermined range so that when a composition (e.g., solution, aerosol, etc.) of the antibody is exposed to the hydrogel it will bind to it with a binding affinity within the ranges described herein as effective.

In general the antibody may bind to the pathogen with a relatively high affinity. For example, the antibody (or fragment thereof) may have a rate of binding to pathogen greater than $10^4$ $M^{-1}/s^{-1}$.

As described above, any appropriate antibody or region of antibody may be used; for example, the Fc region of the antibody binds to the constituent of the biological hydrogel.

Any of these methods may include adding a hydrogel to the patient (e.g., directly to a subject's skin, tissue, wound, etc. and/or indirectly, via an implant, bandage, etc.). The hydrogel may include a constituent of a biological hydrogels such as collagen, laminin, actin, fibronectin, entactin and a combination thereof.

In some embodiments, the antibody (or fragment thereof) may be an IgG antibody with a concentration less than about 100 µg/mL. In some variations, the antibody (or fragment thereof) is an IgM antibody. As mentioned, the antibody binds to a non-neutralizing epitope on the pathogen.

For example, described herein are methods for improving or enhancing the barrier property of a hydrogel against a foreign substance (e.g., a pathogen) in a subject, said method comprising administering to the subject an effective amount of an IgG or IgM antibody to immobilize the foreign substance (e.g., the pathogen), wherein the antibody has a binding affinity of less than about $10^{-2}$ M (e.g., from $10^{-9}$ M to about $10^{-7}$ M) with a constituent of the hydrogel. Any of these methods may also applying the hydrogel to the subject. The hydrogel may be applied externally or internally. The hydrogel may be applied via a device (e.g., a bandage, implant or garment, including as a layer or coating on the device.

A method for trapping a foreign substance (e.g., a pathogen) in a hydrogel as described herein may be a method of treating a pathogen and/or reducing the likelihood or infection by a foreign substance such as a pathogen. For example, any of these methods may include contacting the foreign substance (e.g., the pathogen) with an IgG or IgM antibody in an amount effective to trap the pathogen, wherein the antibody has a binding affinity less than about $10^{-2}$ M (e.g., between about $10^{-9}$ M and about $10^{-7}$ M) with a constituent of the hydrogel.

The antibody may be directed to one or more pathogens, including, but not limited to, classes of pathogens (e.g., bacteria, gram positive bacterial, gram negative bacteria, etc.

For example, a method for preventing or treating an infection in a subject (wherein the infection is caused by a foreign substance such as a pathogen) may include: applying a hydrogel to the subject; and administering to the subject an effective amount of an IgG or IgM antibody, wherein the antibody has a binding affinity of less than about $10^{-2}$ M (e.g., from $10^{-9}$ M to about $10^{-7}$ M) with a constituent of the hydrogel.

As mentioned above, in general, the antibody may be formulated in to a composition suitable for intranasal, oral, by inhalation, or topical administration to a mucosal surface.

Also described herein are matrix complexes (e.g., extracellular matrix complexes) comprising a hydrogel, a plurality of IgG antibodies or IgM antibodies, a plurality of immobilized pathogens, wherein the Fc region of the plurality of IgG antibodies or IgM antibodies binds to a constituent of the biological hydrogel and the Fab region of the plurality of IgG antibodies or IgM antibodies binds to the surface of the plurality of pathogens to immobilize the plurality of the pathogens, and wherein the plurality of IgG antibodies or IgM antibodies has a rate of binding to the plurality of pathogen greater than $10^4$ $M^{-1}$ $s^{-1}$ and a binding affinity of about $10^{-9}$ M to about $10^{-7}$ M with the constituent of the biological hydrogel.

These and other aspects of the invention are set forth in more detail in the description of the invention below.

BRIEF DESCRIPTION OF THE DRAWINGS

FIG. 1 shows a schematic of the model that captures the dynamics of HIV from seminal secretions diffusing across cervicovaginal mucus (CVM) layer containing HIV-binding IgG to reach the underlying vaginal epithelium. To reduce infection, IgG must bind to HIV in sufficient quantities to neutralize or to trap the virions in mucus before HIV virions successfully penetrate CVM and reach the vaginal epithelium. The model captures the tandem effects of IgG-antigen binding kinetics ($k_{on}$, $k_{off}$) as well as IgG-mucin interactions ($m_{on}$, $m_{off}$).

FIGS. 4A-4D show phase diagram mapping of the predicted trapping potency and protection as a function of NIH45-46 concentration in CVM and IgG affinity to mucins as characterized by a, which reflects the ratio of the diffusion coefficients of the monoclonal IgG in mucus vs. water. (A) Fraction of HIV load initially in semen that can diffuse across CVM containing NIH45-46 over the first two hours post-deposition. (B) Average number of NIH45-46 bound to HIV arriving the vaginal epithelium. (C-D) Extent of NIH45-46-mediated protection, as quantified by infectivity relative to (C) no NIH45-46 present in CVM, or (D) the same amount of NIH45-46 present but without any affinity to mucins.

FIGS. 5A-5D show phase diagram mapping of the predicted trapping potency and protection as a function of NIH45-46 unbinding kinetics from HIV virions (koff) as well as accumulation kinetics on HIV virions, which is influenced by both the local NIH45-46 concentrations and binding rate (kon). (A) Fraction of HIV load initially in semen that can diffuse across CVM containing NIH45-46 over the first two hours post-deposition. (B) Average number of NIH45-46 bound to HIV arriving the vaginal epithelium. (C-D) Extent of NIH45-46-mediated protection, as quantified by infectivity relative to (C) no NIH45-46 present in CVM, or (D) the same amount of NIH45-46 present but without any affinity to mucins.

FIG. 7 shows simulations of crosslinker binding to substrate.

FIGS. 9A-9D show diffusion rates of PEG-coated nanoparticles in mCVM treated with different IgM antibodies. (A) Representative trajectories for particles exhibiting effective diffusivities within one SEM of the ensemble average at a time scale of 0.2667 s. (B) Ensemble-averaged geometric mean square displacements (<MSD>) as a function of time scale. (C) Distributions of the logarithms of individual particle effective diffusivities ($D_{eff}$) at a time scale of 0.2667 s. Log $D_{eff}$ values to the left of the dashed line correspond to particles that are effectively trapped, with displacements of less than 100 nm (i.e., less than the particle diameter) within 0.2667 s. (D) Ensemble averaged geometric effective diffusion coefficients at a timescale of 0.2667 s for mucus treated with different IgG and IgM antibodies. Distinct samples are indicated with different circles; averages are indicated by solid lines. * indicates a statistically significant difference (p<0.05). Data represent the ensemble average of four independent experiments, with n≥40 particles per frame (n≥120 particle traces per experiment) on average for each experiment.

FIG. 10 shows representative transverse 50 μm thick frozen tissue sections showing distribution of PEG-coated nanoparticles in mouse vagina treated with control or anti-PEG Ab. Light gray corresponds to PEG-coated nanoparticles, and dark gray corresponds to DAPI-stained cell nuclei.

FIGS. 12A-12D show a dot blot assay demonstrating binding of anti-PEG antibodies to PS-PEG vs. control PS beads. PS and PS-PEG beads were blotted onto nitrocellulose membrane and incubated with (a) anti-PEG IgG, (b) anti-PEG IgM, (c) control IgG or (d) control IgM.

FIGS. 13A-13C show nanoparticle agglutination in mCVM with anti-PEG IgM was only observed when nanoparticles were pre-mixed with anti-PEG IgM prior to addition to mucus (a); no agglutination was observed when anti-PEG IgM was added to mucus first (b) or with control IgM (c). Two representative images are shown for each condition.

FIGS. 14A-14D show diffusion of nanoparticles that are modified with polyethylene glycol and are muco-inert (PS-PEG) in biotinylated basement membrane with neutravidin. (A) Representative trajectories for PS-PEG particles with anti-PEG antibody or biotinylated anti-PEG antibody or without antibody exhibiting effective diffusivities within one SEM of the ensemble average at a time scale of 1 s. (B) Distributions of the logarithms of individual particle effective diffusivities ($D_{eff}$) at a time scale of 0.2667 s. Log $D_{eff}$ values to the left of the dashed line correspond to particles with displacements of less than 100 nm (i.e., roughly the particle diameter) within 0.2667 s. (C) Ensemble-averaged geometric mean square displacements (<MSD>) as a function of time scale. (D) Estimated time for 10% and 50% of viruses and particles to diffuse through a 50 µm thick mucus layer. Data represent the ensemble average of 14 independent AM specimens, with n≥ZZ particles per frame on average (n≥ZZ particle traces per experiment) for each experiment. Error bars represent standard error of the mean (SEM). * indicates a statistically significant difference (p<0.05).

FIGS. 16A-16B show diffusion of PEG-modified nanoparticles in biotinylated basement membrane with biotinylated anti-PEG IgG together with neutravidin, after 30 min and after 24 hr incubation. (A) Ensemble-averaged geometric mean square displacements (<MSD>) as a function of time scale. (B) Distributions of the logarithms of individual particle effective diffusivities ($D_{eff}$) at a time scale of 0.2667 s. Log $D_{eff}$ values to the left of the dashed line correspond to particles with displacements of less than 100 nm (i.e., roughly the particle diameter) within 0.2667 s. Data represent the ensemble average of 4-5 independent experiments per condition, with n≥50 particles per frame on average (n≥61 particle traces per experiment) for each experiment. Error bars represent standard error of the mean (SEM).

where p can be $\tau_P/\tau_M$, N, or $D_A/D_P$. Fixed parameters were $D_A/D_P$=20, N=20, $\tau_P/\tau_M$=20, and [A]$k_{on}/k_{off}$=2.

Figure 22A:
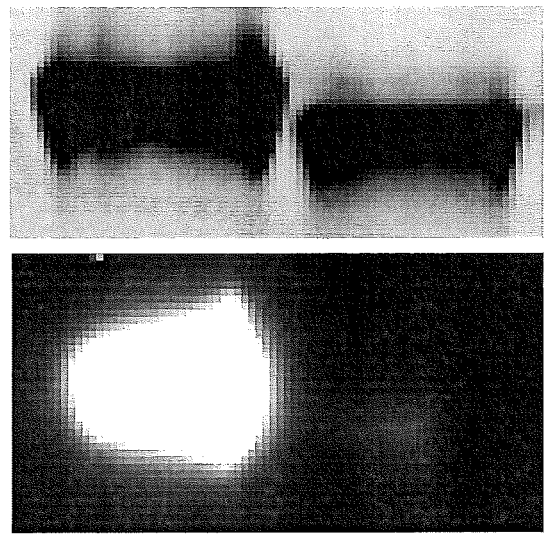
Figure 22B:
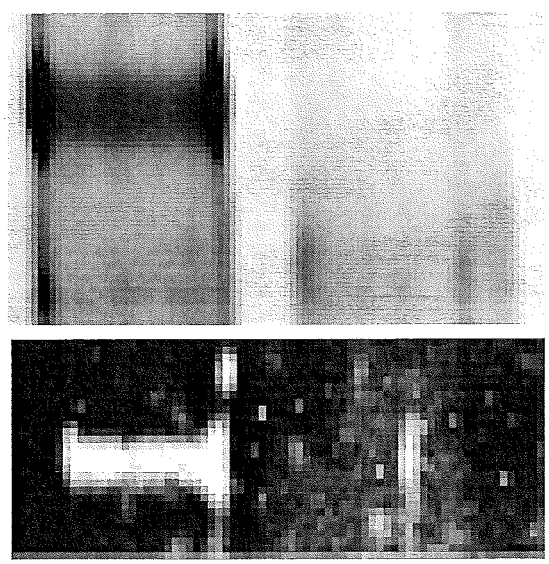
Figure 23C:
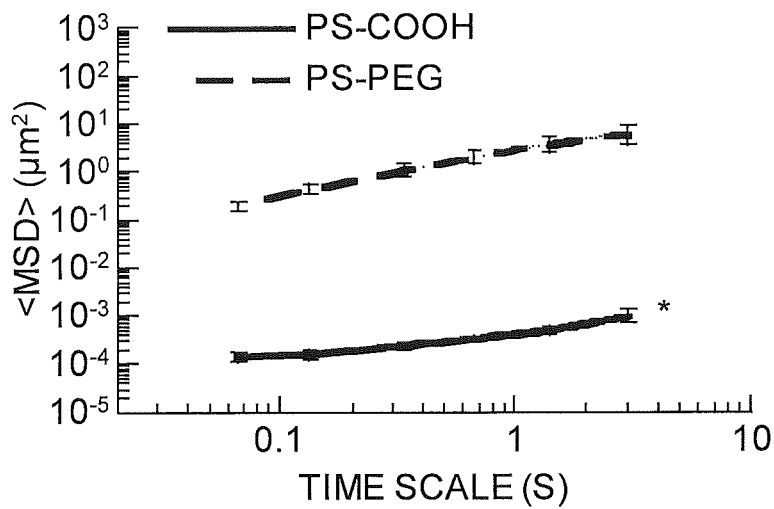
Figure 23D:
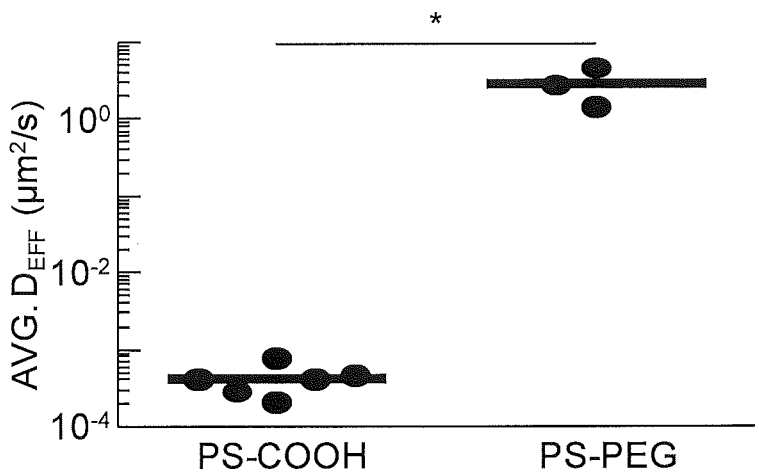
Figure 23E:
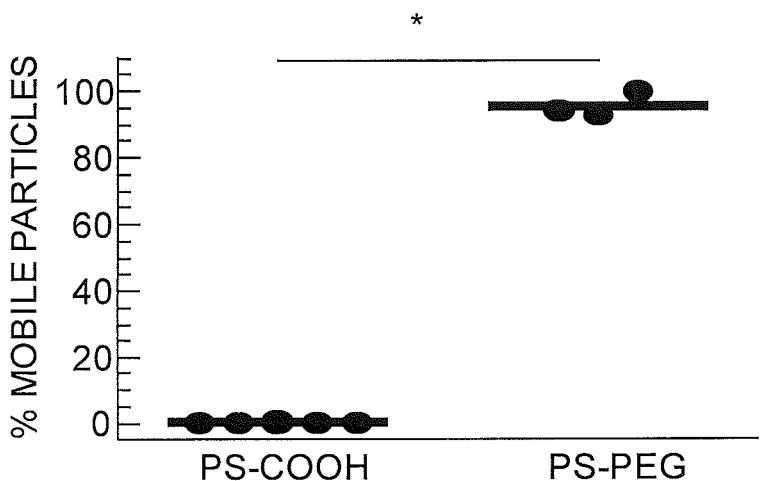

FIGS. 22A-22B show antibody deglycosylation. (A) Heavy chain of reduced, denatured glycosylated IgG (left) and deglycosylated IgG (right) and (B) heavy chain of reduced, denatured glycosylated IgM (left) and deglycosylated IgM (right). Top, silver stain, and bottom, lectin blot for both.

FIGS. 23A-23E show PS-COOH, PS-PEG in Matrigel. (A) Representative particle trajectories of 200 nm PEG-modified polystyrene beads in Matrigel or PS-COOH. (B) Log Deff. (C) MSD trajectories. (D) Avg Deff at t=1 s. (E) % Mobile.

FIGS. 24A-24E show initial IgG anti-PEG in Matrigel (A) Representative particle trajectories of 200 nm PEG-modified polystyrene beads in Matrigel with non-specific antibody or anti-PEG IgG (5 or 10 µg/mL). (B) Log Deff. (C) MSD trajectories. (D) Avg Deff at t=1 s. (E) % Mobile.

FIGS. 25A-25E show initial IgM anti-PEG in Matrigel. (A) Representative particle trajectories of 200 nm PEG-modified polystyrene beads in Matrigel with non-specific antibody or anti-PEG IgM (1, 3, or 5 µg/mL). (B) Log Deff. (C) MSD trajectories. (D) Avg Deff at t=1 s. (E) % Mobile.

FIGS. 26A-26E show deglycosylated IgG, IgM anti-PEG in Matrigel. (A) Representative particle trajectories of 200 nm PEG-modified polystyrene beads in Matrigel with non-specific antibody or deglycosylated anti-PEG IgG or IgM. (B) Log Deff. (C) MSD trajectories. (D) Avg Deff at t=1 s. (E) % Mobile.

Figure 28:
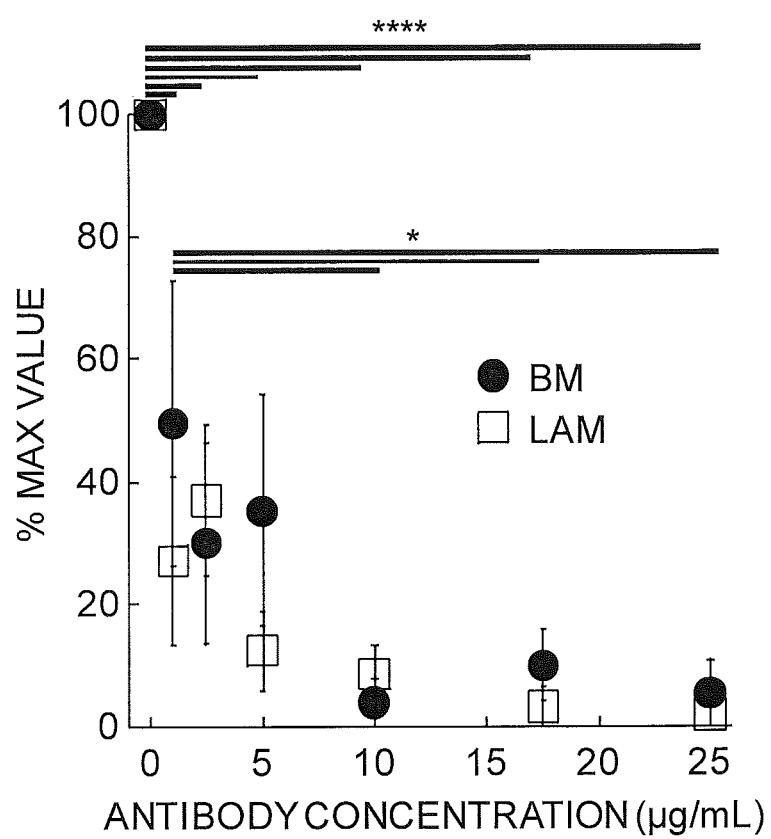

FIGS. 27A-27E show IgG, IgM anti-PEG in LAM. (A) Representative particle trajectories of 200 nm PEG-modified polystyrene beads in LAM with non-specific antibody or anti-PEG IgG or IgM. (B) Log Deff. (C) MSD trajectories. (D) Avg Deff at t=1 s. (E) % Mobile FIG. 28 shows IgG anti-*Salmonella typhimurium* in BM and LAM impairs the flux of *Salmonella* in a transwell experiment. OD600 of *Salmonella* in bottom well was normalized to OD600 of LB alone and of *Salmonella* through matrix without antibody. *p<0.05, ****p<0.0001.

Figure 29A:
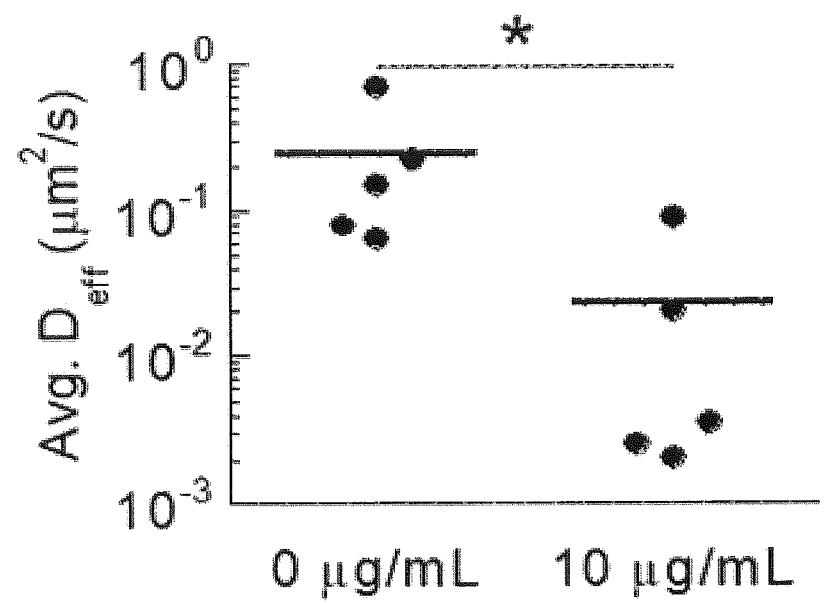
Figure 29B:
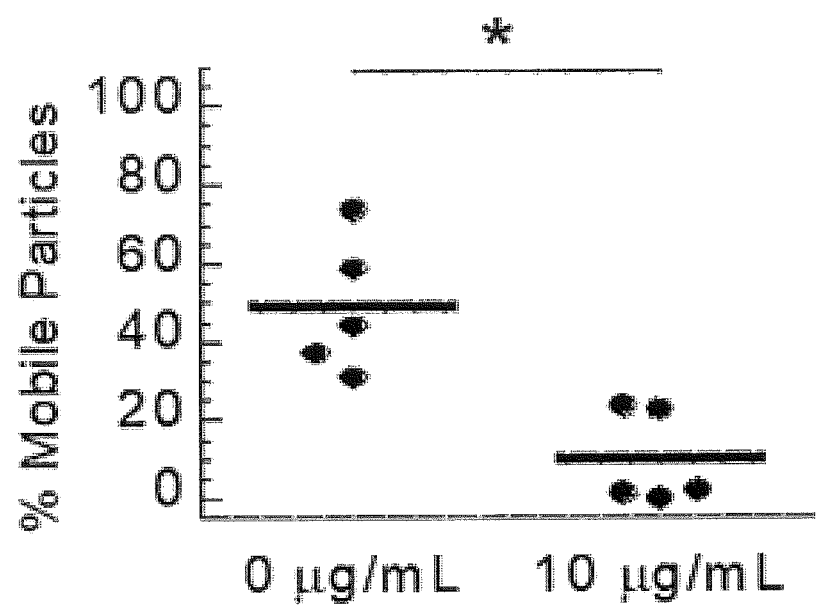

FIGS. 29A-29B show anti-biotin IgG mediates trapping of biotinylated PS-PEG in BM: (A) Average ensemble effective diffusivities ($<D_{eff}>$) at a time scale of 1 s. (B) Fraction of mobile nanoparticles.

Figure 30A:
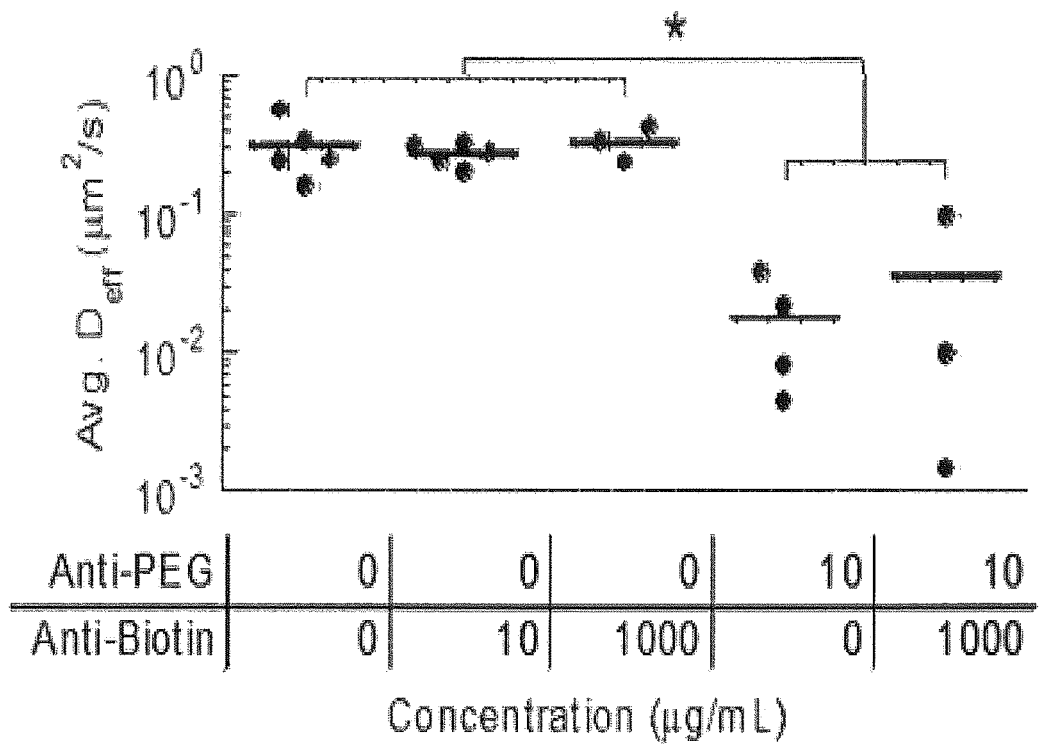
Figure 30B:
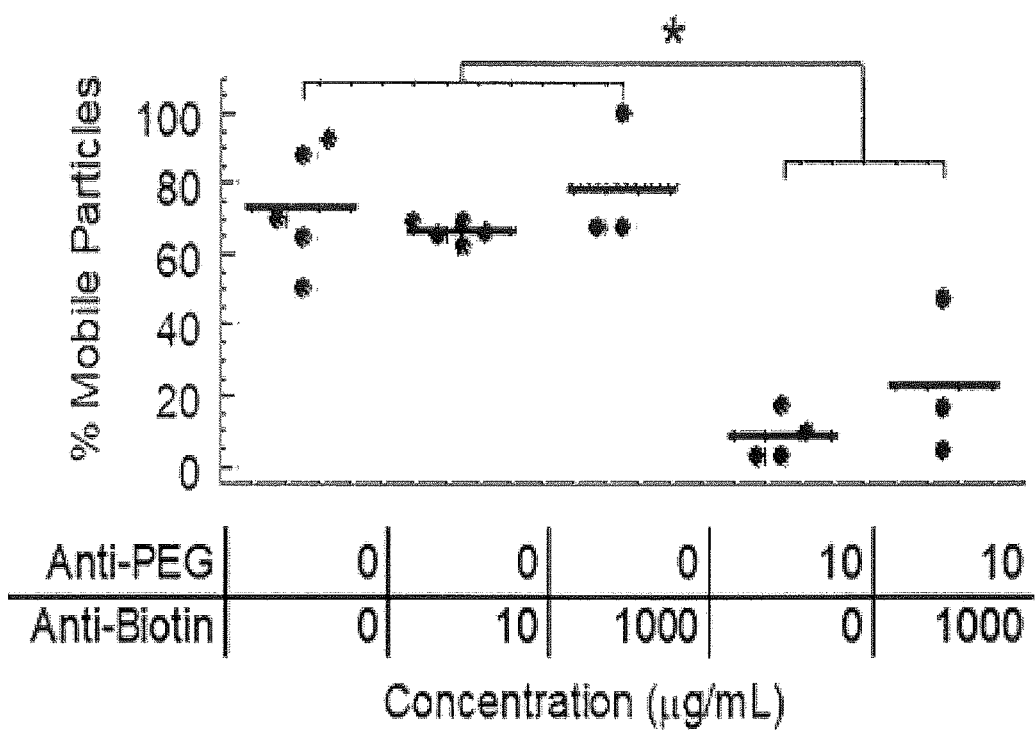

FIGS. 30A-30B show anti-PEG IgG effectively traps ~100 nm PS-PEG in the presence of high concentrations of anti-biotin IgG: (A) Average ensemble effective diffusivities ($<D_{eff}>$) at a time scale of 1 s. (B) Fraction of mobile nanoparticles.

Figure 31:
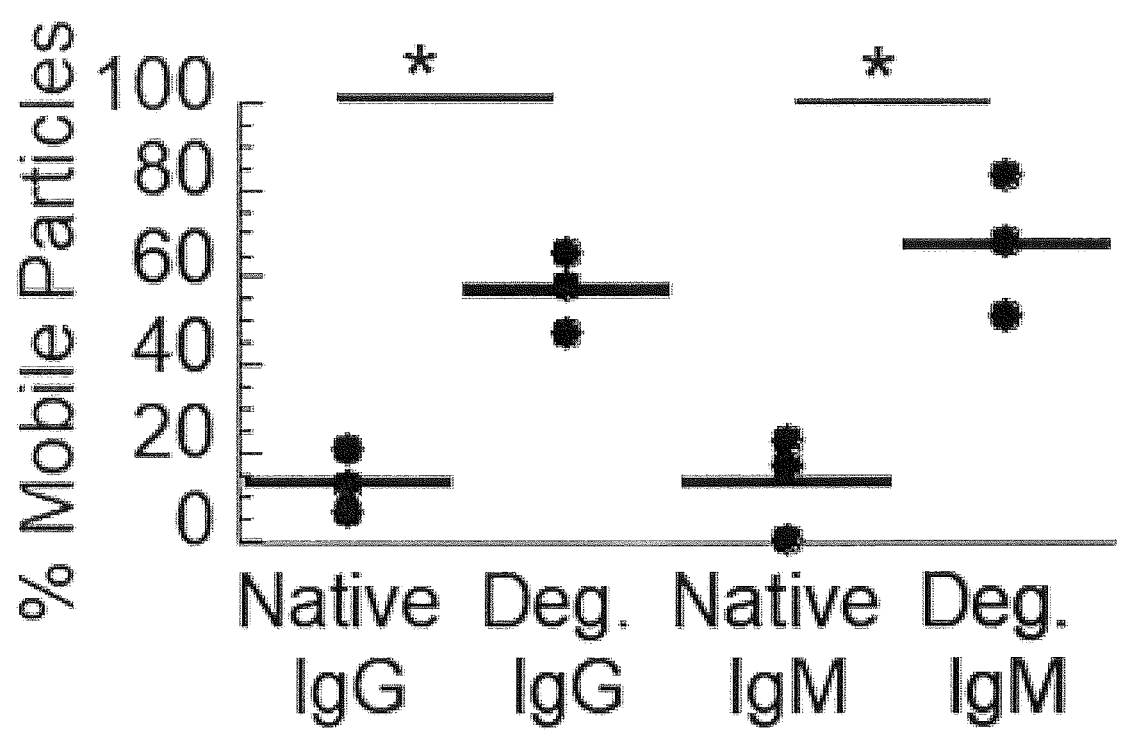

FIG. 31 shows deglycosylated IgG, IgM anti-PEG in Matrigel. Fraction of mobile nanoparticles. * indicates a statistically significant difference (p<0.001) compared to native antibody by one-way ANOVA with post hoc Šidák test in FIG. 24E.

DETAILED DESCRIPTION OF THE INVENTION

The present invention is based, in part, on the development of mathematical models of interactions between antibodies, targets, and substrates. The models permit the identification and/or development of crosslinkers that can bind the target to the substrates and the use of such crosslinkers in methods for preventing and treating infection, providing contraception, monitoring the effectiveness of vaccines, and manipulating (e.g., separating, purifying, washing) the target.

The present invention is explained in greater detail below. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure which do not depart from the instant invention. Hence, the following specification is intended to illustrate some particular embodiments of the invention, and not to exhaustively specify all permutations, combinations and variations thereof.

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a complex comprises components A, B and C, it is specifically intended that any of A, B or C, or a combination thereof, can be omitted and disclaimed singularly or in any combination.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

Except as otherwise indicated, standard methods known to those skilled in the art may be used for production of recombinant and synthetic polypeptides, antibodies or antigen-binding fragments thereof, manipulation of nucleic acid sequences, and production of transformed cells. Such techniques are known to those skilled in the art. See, e.g., SAMBROOK et al., MOLECULAR CLONING: A LABORATORY MANUAL 2nd Ed. (Cold Spring Harbor, N.Y., 1989); F. M. AUSUBEL et al. CURRENT PROTOCOLS IN MOLECULAR BIOLOGY (Green Publishing Associates, Inc. and John Wiley & Sons, Inc., New York).

All publications, patent applications, patents, nucleotide sequences, amino acid sequences and other references mentioned herein are incorporated by reference in their entirety.

I. Definitions

As used in the description of the invention and the appended claims, the singular forms "a," "an" and "the" are intended to include the plural forms as well, unless the context clearly indicates otherwise.

As used herein, "and/or" refers to and encompasses any and all possible combinations of one or more of the associated listed items, as well as the lack of combinations when interpreted in the alternative ("or").

Moreover, the present invention also contemplates that in some embodiments of the invention, any feature or combination of features set forth herein can be excluded or omitted.

Furthermore, the term "about," as used herein when referring to a measurable value such as an amount of a compound or agent of this invention, dose, time, temperature, and the like, is meant to encompass variations of ±20%, ±10%, ±5%, ±1%, ±0.5%, or even ±0.1% of the specified amount.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units is also disclosed. For example, if 10 and 15 are disclosed, then 11, 12, 13, and 14 are also disclosed.

The transitional phrase "consisting essentially of" means that the scope of a claim is to be interpreted to encompass the specified materials or steps recited in the claim, and those that do not materially affect the basic and novel characteristic(s) of the claimed invention.

As used herein, the term "polypeptide" encompasses both peptides and proteins, unless indicated otherwise.

A "nucleic acid" or "nucleotide sequence" is a sequence of nucleotide bases, and may be RNA, DNA or DNA-RNA hybrid sequences (including both naturally occurring and non-naturally occurring nucleotide), but is preferably either single or double stranded DNA sequences.

As used herein, an "isolated" antibody means an antibody separated or substantially free from at least some of the other components of the naturally occurring organism or virus, for example, the cell structural components or other polypeptides or nucleic acids commonly found associated with the antibody. The term also encompasses antibodies that have been prepared synthetically.

By the terms "treat," "treating," or "treatment of" (or grammatically equivalent terms) it is meant that the severity of the subject's condition is reduced or at least partially improved or ameliorated and/or that some alleviation, mitigation or decrease in at least one clinical symptom is achieved and/or there is a delay in the progression of the condition.

As used herein, the terms "prevent," "prevents," or "prevention" and "inhibit," "inhibits," or "inhibition" (and grammatical equivalents thereof) are not meant to imply complete abolition of disease and encompasses any type of prophylactic treatment that reduces the incidence of the condition, delays the onset of the condition, and/or reduces the symptoms associated with the condition after onset.

An "effective," "prophylactically effective," or "therapeutically effective" amount as used herein is an amount that is sufficient to provide some improvement or benefit to the subject. Alternatively stated, an "effective," "prophylactically effective," or "therapeutically effective" amount is an amount that will provide some delay, alleviation, mitigation, or decrease in at least one clinical symptom in the subject. Those skilled in the art will appreciate that the effects need not be complete or curative, as long as some benefit is provided to the subject.

As used herein, the term "trapping potency" refers to the ability of a crosslinker that specially binds to a target to inhibit movement of the target on a substrate. Trapping potency can be measured by methods known in the art and as disclosed herein. Trapping potency can be quantitated, e.g., as the amount of crosslinker (e.g., concentration of crosslinker in mucus) needed to reduce the mobility of at least 50% of the target in the presence of the substrate to at least one-tenth of its mobility in solution (e.g., saline). Mobility in the presence of the substrate can be measured using techniques well known in the art and described herein. Alternatively, trapping potency can be quantitated as the reduction in percentage of target (e.g., pathogens or sperm) that penetrate mucus.

As used herein, the term "bind specifically" or "specifically binds" in reference to a crosslinker of the presently-disclosed subject matter means that the crosslinker of the invention will bind with a target, but does not substantially bind to other unrelated molecules. In certain embodiments, the term refers to a crosslinker that exhibits at least about 60% binding, e.g., at least about 70%, 80%, 90%, or 95% binding, to the target relative to binding to other unrelated molecules.

The term "crosslinker" refers to a molecule that can non-covalently bind a target of interest to a substrate of interest.

II. Methods of Identifying Crosslinkers

The present invention is based on the development of mathematical models that may be used to identify a crosslinker suitable for trapping a target of interest on a substrate of interest. The models may be used to identify the optimal binding affinity between a crosslinker and any given target of interest and substrate of interest for trapping the target on the substrate. The mathematical model takes into account several factors that are important for determining optimal trapping, including two or more factors selected from the fraction of time the crosslinker spends associated with the substrate, the rate of binding of the crosslinker to the target, the crosslinker concentration, the size of the target, the diffusivity of the target, the diffusivity of the crosslinker, and the number of target binding sites. In some embodiments, the model includes at least three, four, or five or more of these factors.

As would be understood by one of skill in the art, the optimal binding affinity for the crosslinker may vary for each target of interest and substrate of interest. In some embodiments, the methods of the present invention may involve determining optimal binding affinities for a given target of interest and substrate of interest using the mathematical models of the invention and then identifying crosslinkers that match the optimal affinities. In other embodiments, crosslinkers are identified that match optimal affinities that have been predetermined for a given target of interest and substrate of interest, e.g., the mathematical models have been used previously (prior to identification of the crosslinkers) to determine optimal affinities for the given target of interest and substrate of interest.

In some embodiments, of the invention, the methods can be used to screen for crosslinkers that match the optimal target binding affinity and substrate binding affinity. In other embodiments, one or more preexisting crosslinkers may be modified to alter the target binding affinity and/or substrate binding affinity of the one or more crosslinkers, which are then screened to identify optimal crosslinkers. The phrase "altering binding affinity" refers to the physical and/or chemical modification of a crosslinker to increase or decrease the binding affinity. For example, one or more crosslinkers may be modified, e.g., by random mutagenesis, and the resulting molecules screened for the desired binding affinity, e.g., using phage display or other techniques known in the art. As another example, a library of molecules, e.g., a combinatorial library, can be prepared and screened for the desired binding affinity.

Thus, one aspect of the invention relates to a method of selecting a crosslinker for trapping a target of interest on a substrate of interest, comprising:

(a) determining an optimal target binding affinity and substrate binding affinity for the target of interest and the substrate of interest using a mathematical model;

(b) measuring the target binding affinity and substrate binding affinity of one or more crosslinkers; and (c) selecting a crosslinker that substantially matches the optimal target binding affinity and substrate binding affinity determined in step (a).

A further aspect of the invention relates to a method of selecting a crosslinker for trapping a target of interest on a substrate of interest, comprising:

(a) determining an optimal target binding affinity and substrate binding affinity for the target of interest and the substrate of interest using a mathematical model;

(b) altering the target binding affinity and/or substrate binding affinity of one or more crosslinkers;

(c) measuring the target binding affinity and substrate binding affinity of the one or more altered crosslinkers; and (d) selecting an altered crosslinker that substantially matches the optimal target binding affinity and substrate binding affinity determined in step (a).

Another aspect of the invention relates to a method of selecting a crosslinker for trapping a target of interest on a substrate of interest, comprising:

(a) measuring the target binding affinity and substrate binding affinity of one or more crosslinkers; and (b) selecting a crosslinker that substantially matches a predetermined optimal target binding affinity and substrate binding affinity.

An additional aspect of the invention relates to a method of selecting a crosslinker for trapping a target of interest on a substrate of interest, comprising:

(a) altering the target binding affinity and/or substrate binding affinity of one or more crosslinkers;

(b) measuring the target binding affinity and substrate binding affinity of the one or more crosslinkers; and (c) selecting an altered crosslinker that substantially matches a predetermined optimal target binding affinity and substrate binding affinity.

The terms "for trapping" and "suitable for trapping" as used herein refer to a crosslinker that provides a binding interaction between a target and a substrate that results in the desired level of immobilization (trapping) of the target on the substrate.

The term "optimal" as used herein with respect to binding affinity refers to a binding affinity that results in the desired level of immobilization of the target on the substrate.

The term "substantially matches the optimal binding affinity" as used herein refers to a crosslinker that has a binding affinity that differs from the calculated affinity by no more than about 20%, e.g., no more than about 15%, 10%, 5%, 4%, 3%, 2%, or 1%. The crosslinker may substantially match the calculated binding affinity of the target binding affinity, the substrate binding affinity, or both.

In some embodiments, the target of interest is a pathogen. The crosslinker is useful for binding target pathogens to trap the pathogen on a surface or in a material to inhibit infection by the pathogen. The surface or material may be any one in which pathogens are found. Examples include, without limitation, mucus, extracellular matrix, basement membranes, hydrogels, and any other gel/matrix systems. Target pathogens of the crosslinker can include any pathogen that can infect a subject through a mucus membrane or other surface as discussed below. Pathogens can be in the categories of algae, bacteria, fungi, parasites (helminths, protozoa), viruses, and subviral agents. Target pathogens further include synthetic systems comprising an antigen having an epitope, for example particles or particulates (e.g., polystyrene beads) comprising attached proteins, e.g., as might be used for bioterrorism.

In some embodiments, the target of interest is a particle or other particulate matter. The particle may be a microparticle (diameter less than 1 mm) or a nanoparticle (diameter less than 1 μm). The particulate matter may be, for example, proteins, nucleic acids, polymers, toxins, and/or small molecules. In some embodiments, the crosslinker binds directly to the particle or particulate matter. In other embodiments, the particle comprises attached proteins, nucleic acids, polymers, and/or small molecules and the crosslinker binds to the attached moieties.

In some embodiments, the substrate of interest is a polymer, e.g., a biopolymer, and the crosslinker traps the target on the polymer. As used herein, the term "biopolymer" refers to a polymer composed of naturally-occurring units. In certain embodiments, the biopolymer is, without limitation, mucin, extracellular matrix, laminin, collagen, actin, or fibronectin. In certain embodiments, the substrate of interest is mucin and the crosslinker traps the target in mucus.

In certain embodiments, the crosslinker is an antibody or an antibody fragment or derivative as described below. In some embodiments, the crosslinker is not a naturally occurring molecule. In some embodiments, the crosslinker is derived from a naturally occurring molecule (e.g., an antibody), such as by chemical modification of the molecule.

The methods of the present invention, including steps of determining optimal binding affinities, can be readily incorporated into kit or system formats that are well known in the art. The terms "kit" and "system," as used herein refer, e.g., to combinations of reagents, or one or more reagents in combination with one or more other types of elements or components (e.g., other types of reagents, containers, packages such as packaging intended for commercial sale, electronic hardware components, etc.).

III. Crosslinkers and Compositions

The presently-disclosed subject matter includes crosslinkers for modulating the movement of a target of interest on a substrate of interest. In particular, the presently-disclosed subject matter relates to crosslinkers and compositions capable of trapping a target of interest on a substrate of interest. As used herein, the term "trapping" refers to the noncovalent binding of a target to a substrate such that the target is at least temporarily restrained in its movement. The crosslinkers can be used advantageously to trap pathogens and sperm in mucus, thereby inhibiting transport of pathogens or sperm across or through mucus secretions, or to trap a target on a substrate for purposes of purification, washing, filtration, etc.

A crosslinker of the invention is a molecule that can noncovalently bind a target of interest to a substrate of interest. In certain embodiments, the crosslinker is a non-naturally occurring molecule. In some embodiments, the crosslinker is an antibody or an antibody fragment or derivative. In other embodiments, the crosslinker is a target binding moiety covalently linked to a substrate binding moiety. The binding moieties may be naturally occurring moieties (e.g., polypeptide sequences) that are synthetically linked together. The crosslinker may be a naturally occurring molecule that has been modified to be non-naturally occurring, e.g., to increase stability or to modify the binding capacity.

One aspect of the invention relates to crosslinkers having optimal binding affinities for both the target of interest and the substrate of interest to provide trapping of the target on the substrate. One important factor for optimization is the affinity of the crosslinker for the substrate, i.e., the amount of time the crosslinker spends associated with the substrate. In certain embodiments, the crosslinker associates with the substrate of interest with an affinity that is sufficient to trap the target of interest on the substrate of interest but not so high that the crosslinker is overly limited in its ability to move in the presence of the substrate. Many naturally occurring antibodies bind the substrate weakly, e.g., an α value of about 0.8-0.9, where α=0 is permanent affinity and α=1 is no affinity. The optimized crosslinkers of the invention will generally have a higher affinity for the substrate of interest than many naturally occurring antibodies. In some embodiments, the crosslinker associates with the substrate of interest at least about 1% of the time but less than 100% of the time, e.g., about 1% of the time to about 95% of the time, e.g., about 1% of the time to about 90% of the time, e.g., about 50% of the time to about 90% of the time, e.g., about 65% of the time to about 85% of the time, e.g., about 75% of the time e.g., about 1% of the time to about 50% of the time, e.g., about 10% of the time to about 45% of the time, e.g., about 20% of the time to about 40% of the time, e.g., about 25% of the time to about 30% of the time. In some embodiments, the crosslinker associates with the substrate of interest about 1%, 5%, 10%, 15%, 20%, 25%, 30%, 35%, 40%, 45%, 50%, 55%, 60%, 65%, 70%, 75%, 80%, 85%, 90%, 95%, or 99% of the time or any range therein. In some embodiments, the crosslinkers of the invention will have an α value of about 0.01 to about 0.9, e.g., about 0.05 to about 0.7, e.g., about 0.1 to about 0.5, e.g., about 0.2 to about 0.4, e.g., about 0.25 to about 0.3. In some embodiments, the crosslinkers of the invention will have an α value of about 0.01, 0.05, 0.1, 0.15, 0.2, 0.25, 0.3, 0.35, 0.4, 0.45, 0.5, 0.55, 0.6, 0.65, 0.7, 0.75, 0.8, 0.85, or 0.9 or any range therein. In some embodiments, the crosslinker associates with the substrate of interest, and has a reduced diffusion coefficient compared to the diffusion coefficient of the crosslinker in water. In some embodiments, the crosslinker is a modified non-native antibody when associates with the substrate of interest such as mucin, has a diffusion coefficient reduced about 25%, about 30%, about 35%, about 40%, about 45%, about 50%, about 55%, about 60%, about 65%, about 70%, about 75%, about 80%, about 85%, about 90%, about 95%, or about 99% or any range therein compared to the diffusion coefficient of the antibody in water. In some embodiments, the antibody has a diffusion coefficient about 20% to 99% less or about 25% to 95% less compared to the diffusion coefficient of the antibody in water. In some embodiments, the antibody associates with the mucins about 20% to 99% of the time, about 25% to 95% of the time or about 30% to about 85% of the time. In one embodiment, the antibody associates with the mucins about 75% of the time and has a diffusion coefficient about 75% less compared to the diffusion coefficient of the antibody in water. Surprisingly, in mucus, native antibody, such as native IgG only associates with mucin about 5 to 10% of the time and has a diffusion coefficient reduced about 5 to 10% compared to the diffusion coefficient of the native antibody in water.

Another important factor for optimization is the rate at which the crosslinker binds to the target of interest. A rapid rate of binding to the target of interest has been found to be an important characteristic, even if the rate of release form the target of interest is also rapid. This is in contrast to most characterizations of antibodies which are based on the affinity of the antibody to the target, not the rate of binding. In certain embodiments, the crosslinker has a rapid rate of binding to the target of interest. In some embodiments, the crosslinker has a rate of binding to the target of interest greater than about $10^4$ $M^{-1}$ $s^{-1}$, e.g., greater than about $2.5 \times 10^4$ $M^{-1}$ $s^{-1}$, $5 \times 10^4$ $M^{-1}$ $s^{-1}$, $1 \times 10^5 M^{-1}$ $s^{-1}$, $2.5 \times 10^5 M^{-1}$ $s^{-1}$, $5 \times 10^5 M^{-1}$ $s^{-1}$, $1 \times 10^6$ $M^{-1}$ $s^{-1}$, $2.5 \times 10^6$ $M^{-1}$ $s^{-1}$, $5 \times 10^6$ $M^{-1}$ $s^{-1}$, or $1 \times 10^7$ $M^{-1}$ $s^{-1}$.

In certain embodiments of the invention, the crosslinker is an antibody, an antibody fragment or derivative, or a molecule that has binding affinities similar to antibodies. The prevailing view of how antibodies protect a subject at mucosal surfaces assumes that neutralization of the pathogen is the primary mechanism of protection. Surprisingly and unexpectedly, in light of this widespread view, the present inventors disclose herein that neutralization is not necessary to protect against infection at mucosal surfaces in a subject. Indeed, it is demonstrated herein that sub-neutralization doses of antibodies to neutralizing epitopes of pathogens can be quite effective at inhibiting infection. Furthermore, it is demonstrated herein that use of antibodies to non-neutralizing epitopes of pathogens can also be quite effective at inhibiting infection.

Antibodies are naturally found in mucus. The current thoughts on antibody-mediated mucosal protection are that secretory IgA (sIgA) antibodies are important for protection because very large amounts of this isotype are found in the gastrointestinal tract. It is further thought that IgG does not play a role in mucosal protection. However, IgG is the dominant isotype in genital secretions and there is approximately a 50:50 ratio of IgG:IgA in respiratory mucus secretions. In contrast to the prevailing thought in the scientific community, it is shown herein that certain antibodies, e.g., IgG, found in CVM can diffuse rapidly through the CVM, slowed only slightly by weak, transient adhesive interactions with mucins within the mucus. This rapid diffusion allows antibodies to accumulate rapidly on pathogen or sperm surfaces. When a plurality of antibodies have accumulated on the surface of a pathogen, the adhesive interactions between the plurality of antibodies and the mucus become sufficient to trap the bound pathogen or sperm in the mucus, thereby preventing infection/providing contraception. Pathogens or sperm trapped in CVM cannot reach their target cells in the mucosal surface, and will instead be shed with post-coital discharge and/or inactivated by spontaneous thermal degradation as well as additional protective factors in mucus, such as defensins (Cole, *Curr. Top. Microbiol. Immunol.* 306:199 (2006); Doss et al., *J. Leukoc. Biol.* 87:79 (2010). As disclosed herein, this pathogen trapping activity provides for protection without neutralization, and can effectively inhibit infection at sub-neutralization doses and/or using antibodies to non-neutralizing epitopes of a pathogen.

In addition to trapping pathogens or sperm in mucus, the crosslinkers (e.g., antibodies) may be used to bind a target of interest to a substrate of interest in any location in vitro or in vivo. In certain embodiments, the crosslinkers may be used to manipulate a target by binding it to a substrate, e.g., to separate, purify, wash, or filter the target. For example, the substrate may be part of a chromatography, dialysis, or filtration medium.

In some embodiments, the crosslinker of the invention is a mixture of crosslinkers that bind to different targets or bind to different portions of the same target.

The crosslinker is useful for binding target pathogens to trap the pathogen in mucus to inhibit infection by the pathogen. Target pathogens of the crosslinker can include any pathogen that can infect a subject through a mucus membrane. Pathogens can be in the categories of algae, bacteria, fungi, parasites (helminths, protozoa), viruses, and subviral agents. Target pathogens further include synthetic systems comprising an antigen having an epitope, for example particles or particulates (e.g., polystyrene beads) comprising attached proteins, e.g., as might be used for bioterrorism.

Pathogens include those that cause sexually-transmitted diseases (listed with the diseases caused by such pathogens), including, without limitation, *Neisseria gonorrhoeae* (gonorrhea); *Chlamydia trachomatis* (*chlamydia*, lymphogranuloma venereum); *Treponema pallidum* (syphilis); *Haemophilus ducreyi* (chancroid); *Klebsiella granulomatis* or *Calymmatobacterium granulomatis* (donovanosis), *Mycoplasma genitalium, Ureaplasma urealyticum* (mycoplasmas); human immunodeficiency virus HIV-1 and HIV-2 (HIV, AIDS); HTLV-1 (T-lymphotrophic virus type 1); herpes simplex virus type 1 and type 2 (HSV-1 and HSV-2); Epstein-Barr virus; cytomegalovirus; human herpesvirus 6; varicella-zoster virus; human papillomaviruses (genital warts); hepatitis A virus, hepatitis B virus, hepatitis C virus (viral hepatitis); molluscum contagiosum virus (MCV); *Trichomona vaginalis* (trichomoniasis); and yeasts, such as *Candida albicans* (vulvovaginal candidiasis). The antibodies and compositions may also be active against other diseases that are transmitted by contact with bodily fluids that may also be transmissible by sexual contact and are capable of being prevented by administration of the compositions according to this invention. Accordingly, the phrase "sexually transmitted diseases (STDs)" is to be interpreted herein as including any disease that is capable of being transmitted in the course of sexual contact, whether or not the genital organs are the site of the resulting pathology.

Pathogens also include those that cause respiratory diseases, including, without limitation, influenza (including influenza A, B, and C); severe acute respiratory syndrome (SARS); respiratory syncytial virus (RSV); parainfluenza; adenovirus; human rhinovirus; coronavirus; and norovirus.

Other pathogens include, without limitation, *Salmonella* and *Escherichia coli*.

Pathogens include those that affect non-human animals, such as livestock, e.g., swine (e.g., porcine epidemic diarrhea virus (PEDV), transmissible gastroenteritis virus (TGEV), rotavirus, classical swine fever virus (CSFV), porcine circovirus type 2 (PCV2), encephalomyocarditis virus (EMCV), porcine reproductive and respiratory syndrome virus (PRRSV), porcine parvovirus (PPV), pseudorabies virus (PRV), Japanese encephalitis virus (JEV), *Brucella, Leptospira, Salmonella*, and *Lawsonia intracellularis, Pasteurella multocida, Brachyspira hyodysenteriae, Mycoplasma hyopneumoniae*), ruminants (e.g., bovine virus diarrhoea virus (BVDV), border disease virus (BDV), bovine papular stomatitis virus (BPSV), pseudocowpox virus (PCPV), *Pasteurella haemolytica, Pasteurella multocida, Haemophilus somnus, Haemophilus agnii, Moraxella bovis, Mycoplasma mycoides, Theileria annulata, Mycobacterium avium* paratuberculosis), ungulates (e.g., *Brucella abortus, Mycobacterium bovis, Theileria parva*, Rift Valley fever virus, foot-and-mouth disease virus, lumpy skin disease virus), horses (e.g., *Rhodococcus equi, Salmonella choleraesuis, Pasteurella multocida*, equine herpesvirus-1, equine herpesvirus-4, equine influenza virus, *Streptococcus equi*), poultry (e.g., fowl pox virus, Newcastle disease virus, Marek's disease virus, avian influenza virus, infectious bursal disease virus (IBDV), avian infectious bronchitis virus (IBV)), and the like.

The terms virus and viral pathogen are used interchangeably herein, and further refer to various strains of virus, e.g., influenza is inclusive of new strains of influenza, which would be readily identifiable to one of ordinary skill in the art. The terms bacterium, bacteria, and bacterial pathogen are used interchangeably herein, and further refer to antibiotic-resistant or multidrug resistant strains of bacterial pathogens. As used herein when referring to a bacterial pathogen, the term "antibiotic-resistant strain" or "multidrug resistant strain" refers to a bacterial pathogen that is capable of withstanding an effect of an antibiotic or drug used in the art to treat the bacterial pathogen (i.e., a non-resistant strain of the bacterial pathogen).

In some embodiments, it is contemplated that a crosslinker according to the presently-disclosed subject matter is capable of broadly binding to viruses containing lipid envelopes, which are not necessarily specific to one virus.

As noted above, it was surprisingly discovered that sub-neutralization doses of a crosslinker can be used to effectively trap a target pathogen or sperm in mucus. As such, in some embodiments, wherein the crosslinker specifically binds a neutralizing epitope of the target pathogen, a sub-neutralization dose can be used. A sub-neutralization doses is a dose below that which would be needed to achieve effective neutralization.

As will be recognized by one of skill in the art, doses appropriate for trapping bacterial pathogens can be higher in some embodiments than the doses appropriate for trapping viral pathogens. It will further be recognized that appropriate doses may differ between pathogens, between mucosal surfaces, and also between individuals.

It is further proposed herein that crosslinkers that selectively bind non-neutralizing epitopes of a target pathogen can be used to effectively trap the target pathogen in mucus. As such, in some embodiments, the crosslinker specifically binds a non-neutralizing epitope, e.g., one or more non-neutralizing epitopes.

The presently-disclosed subject matter further includes a crosslinker that selectively binds a conserved epitope of a target pathogen. A benefit of targeting a conserved epitope would be to preserve efficacy of the crosslinker as against new strains of the pathogen. Targeting such epitopes has been avoided at times in the past because they were viewed as being ineffective targets; however, in view of the disclosure herein that non-neutralizing epitopes can serve as effective targets and/or that sub-neutralization doses can be effective for inhibiting infection, previously dismissed conserved epitopes of target pathogens can be seen as effective targets.

Crosslinkers of the invention are useful for binding sperm to trap the sperm in mucus to inhibit fertilization of an egg by the sperm. Sperm specific antigens that can be used as antibody targets are well known in the art. See, e.g., U.S. Pat. Nos. 8,211,666, 8,137,918, 8,110,668, 8,012,932, 7,339,029, 7,230,073, and 7,125,550, each incorporated by reference in its entirety.

As noted above, it was determined that the low-affinity binding interactions that an antibody forms with mucins are Fc-dependent. As such, the presently-disclosed subject matter includes antibodies having a preserved and/or engineered Fc region. Such antibodies can be, for example, one or more of IgG, IgA, IgM, IgD, or IgE. In certain embodiments, the antibodies are IgG. In some embodiments, the antibodies are one or more subclasses of IgG, e.g., $IgG_1$, $IgG_2$, $IgG_3$, $IgG_4$, or any combination thereof.

In some embodiments, the crosslinker has a sufficient binding rate and/or binding affinity to the target pathogen or sperm to accumulate on the surface of the pathogen or sperm at sufficient levels to trap the pathogen or sperm within one hour after administration of the crosslinker at a crosslinker concentration of less than about 5 µg/ml. The term "trap" in this instance refers to reduction of further movement through the mucus. In some embodiments, the target pathogen or sperm is trapped within about 30 minutes, e.g., about 25, 20, 15, or 10 minutes after administration of the crosslinker. In some embodiments, the crosslinker traps the target pathogen or sperm at a crosslinker concentration of less than about 4, 3, 2, or 1 µg/ml.

In some embodiments, the crosslinker binds to a target of interest that is a particle. The particle may be a microparticle (diameter less than 1 mm) or a nanoparticle (diameter less than 1 µm). In some embodiments, the crosslinker binds directly to the particle. In other embodiments, the particle comprises attached proteins, nucleic acids, polymers, and/or small molecules and the crosslinker binds to the attached moieties.

In some embodiments, the crosslinker binds to a substrate of interest that is a polymer, e.g., a biopolymer, and the crosslinker traps the target on the polymer. In certain embodiments, the biopolymer is, without limitation, mucin, extracellular matrix, laminin, collagen, actin or fibronectin. In certain embodiments, the substrate of interest is mucin and the crosslinker traps the target in mucus.

The following discussion is presented as a general overview of the techniques available for the production of antibodies; however, one of skill in the art will recognize that many variations upon the following methods are known.

The term "antibody" or "antibodies" as used herein refers to all types of immunoglobulins, including IgG, IgM, IgA, IgD, and IgE. The antibody can be monoclonal or polyclonal and can be of any species of origin, including (for example) mouse, rat, rabbit, horse, goat, sheep, camel, or human, or can be a chimeric or humanized antibody. See, e.g., Walker et al., *Molec. Immunol.* 26:403 (1989). The antibodies can be recombinant monoclonal antibodies produced according to the methods disclosed in U.S. Pat. No. 4,474,893 or 4,816,567. The antibodies can also be chemically constructed according to the method disclosed in U.S. Pat. No. 4,676,980. The antibody can be a single monoclonal antibody or a combination of different monoclonal antibodies, e.g., that bind to the same target of interest or different targets of interest.

Antibody fragments and derivatives included within the scope of the present invention include, for example, Fab, Fab', F(ab')$_2$, and Fv fragments; domain antibodies, diabodies; vaccibodies, linear antibodies; single-chain antibody molecules; and multispecific antibodies formed from antibody fragments. Such fragments and derivatives can be produced by known techniques. For example, F(ab')$_2$ fragments can be produced by pepsin digestion of the antibody molecule, and Fab fragments can be generated by reducing the disulfide bridges of the F(ab')$_2$ fragments. Alternatively, Fab expression libraries can be constructed to allow rapid and easy identification of monoclonal Fab fragments with the desired specificity (Huse et al., *Science* 254:1275 (1989)). In some embodiments, the term "antibody fragment or derivative" as used herein may also include any protein construct that is capable of binding a target of interest and associate with a substrate of interest to trap the target on the substrate.

Antibodies of the invention may be altered or mutated for compatibility with species other than the species in which the antibody was produced. For example, antibodies may be humanized or camelized. Humanized forms of non-human (e.g., murine) antibodies are chimeric immunoglobulins, immunoglobulin chains or fragments or derivatives thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues from a complementarity determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the framework (FR) regions (i.e., the sequences between the CDR regions) are those of a human immunoglobulin consensus sequence. The humanized antibody optimally also will comprise at least a portion of an immunoglobulin constant region (Fc), typically that of a human immunoglobulin (Jones et al., *Nature* 321:522 (1986); Riechmann et al., *Nature,* 332:323 (1988); and Presta, *Curr. Op. Struct. Biol.* 2:593 (1992)).

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can essentially be performed following the method of Winter and co-workers (Jones et al., *Nature* 321:522 (1986); Riechmann et al., *Nature* 332:323 (1988); Verhoeyen et al., *Science* 239:1534 (1988)), by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues (e.g., all of the CDRs or a portion thereof) and possibly some FR residues are substituted by residues from analogous sites in rodent antibodies.

Human antibodies can also be produced using various techniques known in the art, including phage display libraries (Hoogenboom and Winter, *J Mol. Biol.* 227:381 (1991); Marks et al., *J Mol. Biol.* 222:581 (1991)). The techniques of Cole et al. and Boerner et al. are also available for the preparation of human monoclonal antibodies (Cole et al., *Monoclonal Antibodies and Cancer Therapy*, Alan R. Liss, p. 77 (1985) and Boerner et al., *J. Immunol.* 147:86 (1991)). Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., *Bio/Technology* 10:779 (1992); Lonberg et al., *Nature* 368:856 (1994); Morrison, *Nature* 368:812 (1994); Fishwild et al., *Nature Biotechnol.* 14:845 (1996); Neuberger, *Nature Biotechnol.* 14:826 (1996); Lonberg and Huszar, *Intern. Rev. Immunol.* 13:65 (1995).

Immunogens (antigens) are used to produce antibodies specifically reactive with target polypeptides. Recombinant or synthetic polypeptides and peptides, e.g., of at least 5 (e.g., at least 7 or 10) amino acids in length, or greater, are the preferred immunogens for the production of monoclonal or polyclonal antibodies. In one embodiment, an immunogenic polypeptide conjugate is also included as an immunogen. The peptides are used either in pure, partially pure or impure form. Suitable polypeptides and epitopes for target pathogens and sperm are well known in the art. Polynucleotide and polypeptide sequences are available in public sequence databases such as GENBANK®/GENPEPT®. Large numbers of neutralizing and non-neutralizing antibodies that specifically bind to target pathogens and sperm have been described in the art and can be used as starting material to prepare the antibodies of the present invention. Alternatively, new antibodies can be raised against target pathogens and sperm using the techniques described herein and well known in the art.

Recombinant polypeptides are expressed in eukaryotic or prokaryotic cells and purified using standard techniques. The polypeptide, or a synthetic version thereof, is then injected into an animal capable of producing antibodies. Either monoclonal or polyclonal antibodies can be generated for subsequent use in immunoassays to measure the presence and quantity of the polypeptide.

Methods of producing polyclonal antibodies are known to those of skill in the art. In brief, an immunogen, e.g., a purified or synthetic peptide, a peptide coupled to an appropriate carrier (e.g., glutathione-S-transferase, keyhole limpet hemocyanin, etc.), or a peptide incorporated into an immunization vector such as a recombinant vaccinia virus is optionally mixed with an adjuvant and animals are immunized with the mixture. The animal's immune response to the immunogen preparation is monitored by taking test bleeds and determining the titer of reactivity to the peptide of interest. When appropriately high titers of antibody to the immunogen are obtained, blood is collected from the animal and antisera are prepared. Further fractionation of the antisera to enrich for antibodies reactive to the peptide is performed where desired. Antibodies, including binding fragments and single chain recombinant versions thereof, against the polypeptides are raised by immunizing animals, e.g., using immunogenic conjugates comprising a polypeptide covalently attached (conjugated) to a carrier protein as described above. Typically, the immunogen of interest is a polypeptide of at least about 10 amino acids, in another embodiment the polypeptide is at least about 20 amino acids in length, and in another embodiment, the fragment is at least about 30 amino acids in length. For example, the polypeptide can comprise amino acids acid residues 1 through 200 from the N-terminal of the papillomavirus L2 protein. The immunogenic conjugates are typically prepared by coupling the polypeptide to a carrier protein (e.g., as a fusion protein) or, alternatively, they are recombinantly expressed in an immunization vector.

Monoclonal antibodies are prepared from cells secreting the desired antibody. These antibodies are screened for binding to normal or modified peptides, or screened for agonistic or antagonistic activity. Specific monoclonal and polyclonal antibodies will usually bind with a $K_D$ of at least about 50 mM, e.g., at least about 1 mM, e.g., at least about 0.1 mM or better. In some instances, it is desirable to prepare monoclonal antibodies from various mammalian hosts, such as mice, rodents, primates, humans, etc. Description of techniques for preparing such monoclonal antibodies are found in Kohler and Milstein 1975 *Nature* 256:495-497. Summarized briefly, this method proceeds by injecting an animal with an immunogen, e.g., an immunogenic peptide either alone or optionally linked to a carrier protein. The animal is then sacrificed and cells taken from its spleen, which are fused with myeloma cells. The result is a hybrid cell or "hybridoma" that is capable of reproducing in vitro. The population of hybridomas is then screened to isolate individual clones, each of which secrete a single antibody species to the immunogen. In this manner, the individual antibody species obtained are the products of immortalized and cloned single B cells from the immune animal generated in response to a specific site recognized on the immunogenic substance.

Alternative methods of immortalization include transformation with Epstein Barr Virus, oncogenes, or retroviruses, or other methods known in the art. Colonies arising from single immortalized cells are screened for production of antibodies of the desired specificity and affinity for the antigen, and yield of the monoclonal antibodies produced by such cells is enhanced by various techniques, including injection into the peritoneal cavity of a vertebrate (preferably mammalian) host. The polypeptides and antibodies of the present invention are used with or without modification, and include chimeric antibodies such as humanized murine antibodies. Other suitable techniques involve selection of libraries of recombinant antibodies in phage or similar vectors. See, Huse et al. 1989 *Science* 246:1275-1281; and Ward et al. 1989 *Nature* 341:544-546.

Antibodies specific to the target polypeptide can also be obtained by phage display techniques known in the art.

Antibodies can sometimes be labeled by joining, either covalently or noncovalently, a substance which provides a detectable signal. A wide variety of labels and conjugation techniques are known and are reported extensively in both the scientific and patent literature. Suitable labels include radionuclides, enzymes, substrates, cofactors, inhibitors, fluorescent moieties, chemiluminescent moieties, magnetic particles, and the like. Such antibodies are useful for detecting or diagnosing the presence of a microbe on which an antigen is found.

Crosslinkers with altered binding affinity to a target of interest and/or a substrate of interest may be created by methods known in the art. Methods include starting with a known crosslinker or crosslinkers (e.g., antibodies) and modifying the structure of the crosslinker to produce a crosslinker with a desired binding affinity. Methods of modification include, without limitation, random mutagenesis or targeted mutagenesis, e.g., to increase the number of moieties on crosslinkers that can interact with the scaffold, such as N-glycans and Fc domains on antibodies, and chemical modification, e.g., whereby a moiety which some affinity to the scaffold is covalently linked to the crosslinker of interest. Screening of modified crosslinkers for altered binding affinity may be carried out using techniques routinely used in the art.

As would be recognized by one skilled in the art, the crosslinkers of the presently-disclosed subject matter can also be formed into suitable compositions, e.g., pharmaceutical compositions for administration to a subject in order to treat or prevent an infection caused by a target pathogen or a disease or disorder caused by infection by a target pathogen or to provide contraception. In one embodiment, the compositions comprise, consist essentially of, or consist of a crosslinker of the invention in a prophylactically or therapeutically effective amount and a pharmaceutically-acceptable carrier. In other embodiments, the compositions comprise, consist essentially of, or consist of a crosslinker of the invention in an amount suitable for in vitro uses, such as manipulation of a target of interest. Such compositions may further comprise water, buffer, or another carrier for the crosslinker.

Pharmaceutical compositions containing the compositions comprise, consist essentially of, or consist of a crosslinker of the invention as disclosed herein can be formulated in combination with any suitable pharmaceutical vehicle, excipient or carrier that would commonly be used in this art, including such conventional materials for this purpose, e.g., saline, dextrose, water, glycerol, ethanol, and combinations thereof. As one skilled in this art would recognize, the particular vehicle, excipient or carrier used will vary depending on the subject and the subject's condition, and a variety of modes of administration would be suitable for the compositions of the invention. Suitable methods of administration of any pharmaceutical composition disclosed in this application include, but are not limited to, topical, oral, intranasal, buccal, inhalation, anal, and vaginal administration, wherein such administration achieves delivery of the crosslinker to a mucus membrane of interest.

The composition can be any type of composition suitable for delivering crosslinker to a mucosal surface and can be in various forms known in the art, including solid, semisolid, or liquid form or in lotion form, either oil-in-water or water-in-oil emulsions, in aqueous gel compositions. Compositions include, without limitation, gel, paste, suppository, douche, ovule, foam, film, spray, ointment, pessary, capsule, tablet, jelly, cream, milk, dispersion, liposomes, powder/talc or other solid, suspension, solution, emulsion, microemulsion, nanoemulsion, liquid, aerosol, microcapsules, time-release capsules, controlled release formulation, sustained release formulation or bioadhesive gel (e.g., a mucoadhesive thermogelling composition) or in other forms embedded in a matrix for the slow or controlled release of the crosslinker to the surface onto which it has been applied or in contact.

If topical administration is desired, the composition may be formulated as needed in a suitable form, e.g., an ointment, cream, gel, lotion, drops (such as eye drops and ear drops), or solution (such as mouthwash). The composition may contain conventional additives, such as preservatives, solvents to promote penetration, and emollients. Topical formulations may also contain conventional carriers such as cream or ointment bases, ethanol, or oleyl alcohol. Other formulations for administration, including intranasal administration, etc., are contemplated for use in connection with the presently-disclosed subject matter. All formulations, devices, and methods known to one of skill in the art which are appropriate for delivering the crosslinker or composition containing the crosslinker to one or more mucus membranes of a subject can be used in connection with the presently-disclosed subject matter.

The compositions used in the methods described herein may include other agents that do not negatively impact or otherwise affect the inhibitory and/or contraceptive effectiveness of the components of the composition, including antibodies, antimicrobial agents, and/or sperm-function inhibitors. For example, solid, liquid or a mixture of solid and liquid pharmaceutically acceptable carriers, diluents, vehicles, or excipients may be employed in the pharmaceutical compositions. Suitable physiologically acceptable, substantially inert carriers include water, a polyethylene glycol, mineral oil or petrolatum, propylene glycol, hydroxyethylcellulose, carboxymethyl cellulose, cellulosic derivatives, polycarboxylic acids, linked polyacrylic acids, such as carbopols; and other polymers such as poly(lysine), poly(glutamic acid), poly(maleic acid), poly(lactic acid), thermal polyaspartate, and aliphatic-aromatic resin; glycerin, starch, lactose, calcium sulphate dihydrate, terra alba, sucrose, talc, gelatin, pectin, acacia, magnesium stearate, stearic acid, syrup, peanut oil, olive oil, saline solution, and the like.

The pharmaceutical compositions described herein useful in the methods of the present invention may further include diluents, fillers, binding agents, colorants, stabilizers, perfumes, gelling agents, antioxidants, moisturizing agents, preservatives, acids, and other elements known to those skilled in the art. For example, suitable preservatives are well known in the art, and include, for example, methyl paraben, propyl paraben, butyl paraben, benzoic acid and benzyl alcohol.

For injection, the carrier will typically be a liquid, such as sterile pyrogen-free water, pyrogen-free phosphate-buffered saline solution, bacteriostatic water, or Cremophor EL[R] (BASF, Parsippany, N.J.). For other methods of administration, the carrier can be either solid or liquid.

For oral administration, the crosslinker can be administered in solid dosage forms, such as capsules, tablets, and powders, or in liquid dosage forms, such as elixirs, syrups, and suspensions. Compositions can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate and the like. Examples of additional inactive ingredients that can be added to provide desirable color, taste, stability, buffering capacity, dispersion or other known desirable features are red iron oxide, silica gel, sodium lauryl sulfate, titanium dioxide, edible white ink and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

Compositions suitable for buccal (sub-lingual) administration include tablets or lozenges comprising the crosslinker in a flavored base, usually sucrose and acacia or tragacanth; and pastilles comprising the antibody in an inert base such as gelatin and glycerin or sucrose and acacia. The composition can comprise an orally dissolvable or degradable composition. Alternately, the composition can comprise a powder or an aerosolized or atomized solution or suspension comprising the crosslinker. Such powdered, aerosolized, or atomized compositions, when dispersed, preferably have an average particle or droplet size in the range from about 0.1 to about 200 nanometers.

Compositions of the present invention suitable for parenteral administration comprise sterile aqueous and non-aqueous injection solutions of the crosslinker, which preparations are preferably isotonic with the blood of the intended recipient. These preparations can contain anti-oxidants, buffers, bacteriostats and solutes which render the composition isotonic with the blood of the intended recipient. Aqueous and non-aqueous sterile suspensions can include suspending agents and thickening agents. The compositions can be presented in unit/dose or multi-dose containers, for example sealed ampoules and vials, and can be stored in a freeze-dried (lyophilized) condition requiring only the addition of the sterile liquid carrier, for example, saline or water-for-injection immediately prior to use.

Extemporaneous injection solutions and suspensions can be prepared from sterile powders, granules and tablets of the kind previously described. For example, in one aspect of the present invention, there is provided an injectable, stable, sterile composition comprising a crosslinker, in a unit dosage form in a sealed container. The crosslinker is provided in the form of a lyophilizate which is capable of being reconstituted with a suitable pharmaceutically acceptable carrier to form a liquid composition suitable for injection thereof into a subject.

Compositions suitable for rectal administration are preferably presented as unit dose suppositories. These can be prepared by admixing the crosslinker with one or more conventional solid carriers, for example, cocoa butter, and then shaping the resulting mixture.

The crosslinker can alternatively be formulated for nasal administration or otherwise administered to the lungs of a subject by any suitable means, e.g., administered by an aerosol suspension of respirable particles comprising the crosslinker, which the subject inhales. The respirable particles can be liquid or solid. The term "aerosol" includes any gas-borne suspended phase, which is capable of being inhaled into the bronchioles or nasal passages. Specifically, aerosol includes a gas-borne suspension of droplets, as can be produced in a metered dose inhaler or nebulizer, or in a mist sprayer. Aerosol also includes a dry powder composition suspended in air or other carrier gas, which can be delivered by insufflation from an inhaler device, for example. See Ganderton & Jones, *Drug Delivery to the Respiratory Tract*, Ellis Horwood (1987); Gonda (1990) *Critical Reviews in Therapeutic Drug Carrier Systems* 6:273-313; and Raeburn et al., *J. Pharmacol. Toxicol. Meth.* 27:143 (1992). Aerosols of liquid particles comprising the crosslinker can be produced by any suitable means, such as with a pressure-driven aerosol nebulizer or an ultrasonic nebulizer, as is known to those of skill in the art. See, e.g., U.S. Pat. No. 4,501,729. Aerosols of solid particles comprising the crosslinker can likewise be produced with any solid particulate medicament aerosol generator, by techniques known in the pharmaceutical art.

Alternatively, one can administer the crosslinker in a local rather than systemic manner, for example, in a depot or sustained-release formulation.

One aspect of the invention relates to devices coated or impregnated with the crosslinkers and compositions of the invention. The device can be for delivery of the crosslinkers and compositions of the invention to a mucus membrane, e.g., to the vagina or uterus. In one embodiment, a device includes a solid support adapted to be inserted into the vagina. The support can be impregnated with or coated with a composition. The release of crosslinkers from the devices may be controlled by the material composing these devices, such as silicone elastomers, ethylene vinyl acetate and polyurethane polymers. Devices, such as cervicovaginal and rectal devices, include, without limitation, a ring, rod, applicator, sponge, cervical cap, tampon, diaphragm, or intrauterine device. Applicators can be those currently used commercially to deliver spermicidal gels or anti-yeast compounds and include, without limitation, plunger-type applicators, pessaries, sprays, squeezable tubes, vaginal rings, cervical rings, sponges, and the like. All such means for delivery are intended to be encompassed by the present invention.

As noted herein, crosslinkers of the presently-disclosed subject matter are capable of diffusing through mucus when they are unbound, to allow the crosslinker to bind a target pathogen or sperm at a desirable rate. It is also desirable that, when crosslinkers are bound to the pathogen or sperm, the cumulative effect of the crosslinker-mucin interactions effectively traps the pathogen or sperm in the mucus. To facilitate this goal, in some embodiments, it can be desirable to provide a composition that includes more than one crosslinker, wherein each crosslinker specifically binds a different portion (e.g., epitope) of the target pathogen or sperm. Such a composition provides the ability for an increased number of crosslinkers to become bound to the pathogen or sperm, thereby strengthening the crosslinker-mucin interactions that serve to trap the pathogen or sperm in the mucus.

In some embodiments of the presently-disclosed subject matter, a composition includes a first crosslinker and a second crosslinker, as disclosed herein, wherein the first crosslinker specifically binds a first portion (e.g., epitope) of the target pathogen or sperm and the second crosslinker specifically binds a second portion (e.g., epitope) of the target pathogen or sperm, wherein said first portion is distinct from the second portion. In certain embodiments, the composition includes three or more different crosslinkers, e.g., 3, 4, 5, 6, 7, 8, 9, 10, or more different crosslinkers, wherein each crosslinker specifically binds a different portion or epitope of the target pathogen or sperm.

In some embodiments of the presently-disclosed subject matter, a composition includes a first crosslinker that specifically binds a gG surface glycoprotein of HSV, a second crosslinker that specifically binds a gD surface glycoprotein of HSV, and/or a third crosslinker that specifically binds a gB surface glycoprotein of HSV.

It is also desirable to provide a composition that can provide treatment or prevention of infection due to more than one target pathogen. In some embodiments of the presently-disclosed subject matter, a composition includes a first crosslinker and a second crosslinker, as disclosed herein, wherein the first crosslinker specifically binds a portion (e.g., epitope) of a first target pathogen and the second crosslinker specifically binds a portion (e.g., epitope) of second target pathogen. In certain embodiments, the composition includes three or more different crosslinkers, e.g., 3, 4, 5, 6, 7, 8, 9, 10, or more different crosslinkers, wherein each crosslinker specifically binds a portion or epitope of a different target pathogen.

In other embodiments, a composition provides both contraception and treatment or prevention of infection by one or more target pathogens. In some embodiments of the presently-disclosed subject matter, a composition includes a first crosslinker and a second crosslinker, as disclosed herein, wherein the first crosslinker specifically binds sperm and the second crosslinker specifically binds a target pathogen. In certain embodiments, the composition includes three or more different crosslinkers, e.g., 3, 4, 5, 6, 7, 8, 9, 10, or more different crosslinkers, wherein one or more crosslinkers bind different portions (e.g., epitopes) of sperm and one or more crosslinkers specifically binds a portion (e.g., epitope) of a target pathogen or multiple target pathogens.

In some embodiments, the pharmaceutical composition can further include an additional active agent, e.g., a prophylactic or therapeutic agent. For example, the additional active agent can be an antimicrobial agent, as would be known to one of skill in the art. The antimicrobial agent may be active against algae, bacteria, fungi, parasites (helminths, protozoa), viruses, and subviral agents. Accordingly, the antimicrobial agent may be an antibacterial, antifungal, antiviral, antiparasitic, or antiprotozoal agent. The antimicrobial agent is preferably active against infectious diseases.

Suitable antiviral agents include, for example, virus-inactivating agents such as nonionic, anionic and cationic surfactants, and C31 G (amine oxide and alkyl betaine), polybiguanides, docosanol, acylcarnitine analogs, octyl glycerol, and antimicrobial peptides such as magainins, gramicidins, protegrins, and retrocyclins. Mild surfactants, e.g., sorbitan monolaurate, may advantageously be used as antiviral agents in the compositions described herein. Other antiviral agents that may advantageously be utilized in the compositions described herein include nucleotide or nucleoside analogs, such as tenofovir, acyclovir, amantadine, didanosine, foscarnet, ganciclovir, ribavirin, vidarabine, zalcitabine, and zidovudine. Further antiviral agents that may be used include non-nucleoside reverse transcriptase inhibitors, such as UC-781 (thiocarboxanilide), pyridinones, TIBO, nevaripine, delavirdine, calanolide A, capravirine and efavirenz. From these reverse transcriptase inhibitors, agents and their analogs that have shown poor oral bioavailability are especially suitable for administration to mucosal tissue, in combination with antibodies and compositions of the invention, to prevent sexual transmission of HIV. Other antiviral agents that may be used are those in the category of HIV entry blockers, such as cyanovirin-N, cyclodextrins, carregeenans, sulfated or sulfonated polymers, mandelic acid condensation polymers, monoclonal antibodies, chemokine receptor antagonists such as TAK-779, SCH-C/D, and AMD-3100, and fusion inhibitors such as T-20 and 1249.

Suitable antibacterial agents include antibiotics, such as aminoglycosides, cephalosporins, including first, second and third generation cephalosporins; macrolides, including erythromycins, penicillins, including natural penicillins, penicillinase-resistant penicillins, aminopenicillins, extended spectrum penicillins; sulfonamides, tetracyclines, fluoroquinolones, metronidazole and urinary tract antiseptics.

Suitable antifungal agents include amphotericin B, nystatin, griseofulvin, flucytosine, fluconazole, potassium iodide, intraconazole, clortrimazole, miconazole, ketoconazole, and tolnaftate.

Suitable antiprotozoal agents include antimalarial agents, such as chloroquine, primaquine, pyrimethamine, quinine, fansidar, and mefloquine; amebicides, such as dioloxamide, emetine, iodoquinol, metronidazole, paromomycine and quinacrine; pentamidine isethionate, atovaquone, and eflornithine.

In certain embodiments, the additional active agent can be a sperm-function inhibitor, e.g., an agent that has the ability to inhibit the function of sperm, to otherwise inhibit fertilization of an egg by sperm and/or to otherwise prevent pregnancy, such as by killing and/or functionally inactivating sperm or by other effects on the activity of the sperm. In some embodiments, the active agent may have at least dual functions, such as acting as a sperm-function inhibitor and as an antimicrobial agent.

Sperm-function inhibitors include, without limitation, surfactants, including nonionic surfactants, cationic surfactants, and anionic surfactants; spermicides, such as nonoxynol-9 (α-(4-Nonylphenyl)-ω-hydroxynona(oxyethylene); other sperm-inactivators such as sulfated or sulfonated polymers such as polystyrene sulfonate, mandelic acid condensation polymers, cyclodextrins; antimicrobial peptides such as gramicidins, magainins, indolicidin, and melittin; and acid-buffering compositions, such as BufferGel and Acid-Form. Nonionic surfactants include, for example, sorbitan monolaurate, nonylphenoxypolyethoxy ethanol, p-diisobutyphenoxypolyethoxy ethanol, polyoxyethylene (10) oleyl ether and onyx-ol. Suitable anionic surfactants include, without limitation, sodium alkyl sulfonates and the sodium alkylbenzene sulfonates. Cationic surfactants include, for example, the quaternary ammonium surfactants, such as cetyl pyrimidinium chloride and benzalkonium chlorides. Zwitterionic surfactants such as acylcarnitine analogs and C31G are especially suitable for their mild skin and mucosal irritation properties.

The presently-disclosed subject matter further includes a kit, including the crosslinker or composition comprising the crosslinker as described herein; and optionally a device for administering the crosslinker or composition. In some embodiments, the kit can include multiple crosslinkers and/or compositions containing such crosslinkers. In some embodiments, each of multiple crosslinkers provided in such a kit can specifically bind to a different portion (e.g., epitope) of the target pathogen or sperm. In other embodiments, each of multiple crosslinkers provided in such a kit can specifically bind to a portion (e.g., epitope) of a different target pathogen or to and epitope of sperm. In some embodiments, the kit can further include an additional active agent, e.g., antimicrobial, such as an antibiotic, an antiviral, or other antimicrobial, or a sperm-function inhibitor as would be known to one of skill in the art. For in vitro uses, the kit may further comprise buffers, reagents, and/or other components for manipulating the target of interest.

IV. Prevention and Treatment of Infection

The presently-disclosed subject matter further includes methods of inhibiting or treating an infection by a target pathogen in a subject, including administering to a subject, e.g., to a mucosa of the subject, a crosslinker and/or composition as disclosed herein. The mucosa can be selected from, for example, a respiratory tract mucosa (e.g., a nasal mucosa, a lung mucosa), a reproductive tract mucosa (e.g., a genital mucosa, an uterine mucosa, a vaginal mucosa), an ocular mucosa, and a gastrointestinal mucosa (e.g., an oral mucosa, an anal mucosa), and any combination thereof. The surface may be a non-mucosal surface, e.g., skin, blood vessels, central nervous system, extracellular matrix, etc. In certain embodiments, the methods comprise additional steps such as one or more of isolating/preparing the crosslinkers, preparing a composition of the crosslinkers, determining the level of antibodies in the mucus of the subject before administering the crosslinkers, and determining the level of crosslinkers in the mucus of the subject after administering the crosslinkers.

The crosslinkers and compositions of the present invention according to the methods described herein are administered or otherwise applied by delivering the composition, typically to a site of infection. The site of infection may be one where an infection is already present (an actual site of infection) or where an infection is likely to occur (a potential site of site of infection in or on an uninfected individual). In some embodiments, the crosslinkers and compositions may be topically delivered. In other embodiments, the crosslinkers and compositions may be systemically delivered such that the crosslinkers are secreted into the mucus of the subject. Accordingly, the compositions as described above may be delivered to a mucosal surface, e.g., to the reproductive tract, e.g., to the vulva, including the vaginal cavity, and/or to the gastrointestinal tract, e.g., the ano-rectal and buccal cavities and/or to the respiratory tract, e.g., the nasal cavity and the lungs. In the vaginal cavity, the compositions may be applied to any portion of the uterus, including inside the uterus and on the cervix, including the mucosa and/or lining of the endo- and ecto-cervix. The ano-rectal cavity includes the perianal surface and the lining of the anus. Topical delivery to the gastrointestinal tract includes oral administration such that the crosslinkers reach, e.g., the small and/or large intestines. For example, oral administration of an enteric-coated solid oral dosage form (e.g., tablet or capsule) can effectively carry the crosslinkers through the stomach unharmed with release occurring in the intestines.

An effective amount of the crosslinker can be administered. As used herein, an "effective amount" of the crosslinker for inhibition of infection refers to a dosage sufficient to inhibit infection by the target pathogen. As used herein, an "effective amount" of the crosslinker for treatment of infection refers to a dosage sufficient to inhibit spread of the target pathogen from infected cells to non-infected cells in the subject and/or to inhibit spread of the target pathogen from the infected subject to another subject, e.g., an infected or non-infected subject. The effective amount can be an amount sufficient to trap an amount of the target pathogen in mucus or another substrate. As will be recognized by one of skill in the art, the amount can vary depending on the patient and the target pathogen. The exact amount that is required will vary from subject to subject, depending on the species, age, and general condition of the subject, the particular carrier or adjuvant being used, mode of administration, and the like. As such, the effective amount will vary based on the particular circumstances, and an appropriate effective amount can be determined in a particular case by one of skill in the art using only routine experimentation. In some instances, an effective amount of the crosslinker that specifically binds the target pathogen or sperm can be an amount that achieves a concentration of the crosslinker in the mucus of about 0.1 µg/mL to about 1000 µg/mL, e.g., about 0.5 µg/mL to about 100 µg/mL, e.g., about 1 µg/mL to about 50 µg/mL or any range therein. In some embodiments, the crosslinker may be administered in two or more stages with different doses in each stage. For example, higher doses can be administered initially in order to clear target pathogens that are present in the mucus of exposed or infected subjects and ensure that sufficient amounts of crosslinker remain in the mucus to provide protection, e.g., for about 24 hours. In later stages, lower doses can be administered to maintain protective levels of the crosslinker. In other embodiments, protective doses can be administered to subjects that are likely to be exposed to a pathogen and higher doses can be administered if infection occurs.

As will be recognized by one of skill in the art, the term "inhibiting" or "inhibition" does not refer to the ability to completely eliminate the possibility of infection in all cases. Rather, the skilled artisan will understand that the term "inhibiting" refers to reducing the chances of pathogens moving through mucus beyond the mucus membrane such that infection of a subject can occur, such as reducing chances of infection by a pathogen when such pathogen is bound to trapping crosslinkers in mucus. Such decrease in infection potential can be determined relative to a control that has not been administered the crosslinkers of the invention. In some embodiments, the decrease of inhibition relative to a control can be about a 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% decrease.

In some embodiments inhibiting or treating an infection in a subject can comprise trapping a pathogen in mucus or another substrate. As such, in some embodiments a method of trapping a target pathogen in mucus is provided, which method includes administering to a mucosa of the subject a crosslinker or composition as described herein.

In some embodiments, a method of inhibiting or treating an infection in a subject, and/or trapping a pathogen in the mucus of a subject, involves administering to a mucosa of the subject a composition comprising an isolated antibody that specifically binds a non-neutralizing epitope of a target pathogen. The antibody can be a non-neutralizing antibody. In some embodiments, the non-neutralizing antibody is provided at a concentration above a predetermined amount.

In some embodiments, a method of inhibiting or treating an infection in a subject, and/or trapping a pathogen in the mucus of a subject, involves administering to a mucosa of the subject a composition comprising an isolated antibody that specifically binds a neutralizing epitope of a target pathogen, wherein the antibody is provided at a sub-neutralization dose.

As used herein, the term "subject" refers to humans and other animals. Thus, veterinary treatment is provided in accordance with the presently-disclosed subject matter. As such, the presently-disclosed subject matter provides for the treatment of mammals such as humans, as well as those mammals of importance due to being endangered, such as Siberian tigers; of economic importance, such as animals raised on farms; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Thus, also provided is the treatment of livestock, including, but not limited to, domesticated swine, ruminants, ungulates, horses (including race horses), poultry, and the like.

A subject in need of inhibiting an infection or a disease or disorder caused by an infection is a subject that has been identified as being at risk of infection. In some embodiments, the subject is identified as having been exposed to the target pathogen. In other embodiments, the subject is in contact with other subjects that are infected or are likely to become infected, e.g., a subject that is living with, working with, and/or attending school with infected subjects.

A subject in need of treating an infection or a disease or disorder caused by an infection is a subject that has been diagnosed as infected with a pathogen or is suspected of being infected with a pathogen, e.g., exhibiting symptoms of infection.

In some embodiments, the subject is one that does not have antibodies targeted to the pathogen or has antibodies targeted to the pathogen that are not effective to inhibit or treat infection by the pathogen.

In particular embodiments of the invention, more than one administration (e.g., two, three, four, or more administrations) of the crosslinker, composition, or device comprising the composition can be employed over a variety of time intervals (e.g., hourly, daily, weekly, monthly, etc.) to achieve prophylactic and/or therapeutic effects.

In some embodiments, the method include administering a crosslinker, and further administering an additional active agent, e.g., prophylactic or therapeutic agent, e.g., an antimicrobial, such as an antibiotic, an antiviral, or other antimicrobial as would be known to one of skill in the art. The additional active agents can be delivered concurrently with the crosslinkers and compositions of the invention. The additional active agents can be delivered in the same composition as the crosslinker or in separate compositions. As used herein, the word "concurrently" means sufficiently close in time to produce a combined effect (that is, concurrently can be simultaneously, or it can be two or more events occurring within a short time period before or after each other).

As used herein, the term foreign substance means any substance that can cause an infection. The foreign substance includes, but is not limited to, a pathogen, a bacterium, a virus, a foreign particle or particulate, a cell, e.g., a sperm cell, a microorganism, a germ, a protozoa, an infective agent or an infectious agent.

In some embodiments, the disclosure provides a method for improving or enhancing the barrier property of hydrogels such as biological hydrogels against a foreign substance (e.g., a pathogen). The method includes/comprises contacting the foreign substance (e.g., the pathogen) with an antibody in an amount effective to immobilize the foreign substance (e.g., the pathogen), wherein the antibody has a binding affinity $K_D$ less than about $10^{-2}$ M with a constituent of the hydrogels. For example, the antibody's binding affinity with a constituent of the hydrogels can be less than about $5\times10^{-3}$ M, less than about $10^{-3}$ M, less than about $5\times10^{-4}$ M, less than about $10^{-4}$ M, less than about $5\times10^{-5}$ M, less than about $10^{-5}$ M, less than about $5\times10^{-6}$ M, less than about $10^{-6}$ M, less than about $5\times10^{-7}$ M, less than about $10^{-7}$ M, less than about $10^{-8}$ M, less than about $5\times10^{-9}$ M, or less than about $10^{-9}$ M, or any range therein. In some embodiments, the antibody's binding affinity with a constituent of the hydrogels can be between about $10^{-9}$ [M] and about $10^{-7}$ [M], between about $10^{-9}$ [M] and about $10^{-8}$ [M], between about $10^{-8}$ [M] and about $10^{-7}$ [M], between about $7\times10^{-9}$ [M] and about $2\times10^{-7}$ [M], between about $3\times10^{-9}$ [M] and about $2\times10^{-8}$ [M], between about $2\times10^{-8}$ [M] and about $2\times10^{-7}$ [M], between about $3\times10^{-9}$ [M] and about $7\times10^{-9}$ [M], or between about $10^{-9}$ M and $10^{-2}$ M. The antibody can be a monoclonal or polyclonal antibody. Examples of the antibodies can be used include, but are not limited to, IgG, IgA, IgM, or a fragment or derivative thereof. In some instances, antibody can be IgG or IgM. When an IgG or IgM antibody is used, it can have a binding affinity $K_D$ of less than about $2\times10^{-7}$ [M], e.g., less than about $10^{-7}$ [M], $9\times10^{-8}$ [M], $8\times10^{-8}$ [M], $7\times10^{-8}$, $6\times10^{-8}$ [M], $5\times10^{-8}$ [M], $4\times10^{-8}$ [M], $3\times10^{-8}$ [M], $2\times10^{-8}$ [M], $10^{-8}$ [M], $9\times10^{-9}$ [M], $8\times10^{-9}$ [M], $7\times10^{-9}$ [M], $6\times10^{-9}$ [M], $5\times10^{-9}$ [M], $4\times10^{-9}$ [M], $3\times10^{-9}$ [M], $2\times10^{-9}$ [M], or $10^{-9}$ [M], or any range therein.

In some embodiments, the antibody has a rate of binding to pathogen greater than about $10^4$ $M^{-1}$ $s^{-1}$, e.g., greater than about $2.5\times10^4$ $M^{-1}$ $s^{-1}$, $5\times10^4$ $M^{-1}$ $s^{-1}$, $1\times10^5$ $M^{-1}$ $s^{-1}$, $2.5\times10^5$ $M^{-1}s^{-1}$, $5\times10^5$ $M^{-1}$ $s^{-1}$, $1\times10^6$ $M^{-1}$ $s^{-1}$, $2.5\times10^6$ $M^{-1}$ $s^{-1}$, $5\times10^6$ $M^{-1}$ $s^{-1}$, or $1\times10^7$ $M^{-1}$ $s^{-1}$. The pathogen can be a virus, a bacterium or a microorganism.

The constituents of the biological hydrogels can include collagen, laminin, actin, fibronectin, entactin and a combination thereof.

In some embodiments, the antibody binds to a non-neutralizing epitope on the pathogen. In other embodiments, the antibody binds to a neutralizing epitope on the pathogen.

In some embodiments, the disclosure provides a method for improving or enhancing the barrier property of extracellular matrices, such as biological hydrogels against a foreign substance (e.g., a pathogen) in a subject. The method includes/comprises administering to the subject an effective amount of an IgG or IgM antibody to immobilize the foreign substance such as the pathogen, wherein the antibody has a binding affinity less than about $10^{-2}$ M (e.g., from about $10^{-9}$ M to about $10^{-7}$ M) with a constituent of the biological hydrogels.

In some embodiments, the disclosure provides a method for tuning the barrier property of biological hydrogels against a foreign substance (e.g., a pathogen) in a subject. The method includes/comprises administering to the subject an effective amount of an IgG or IgM antibody to immobilize the foreign substance such as the pathogen, wherein the antibody has a binding affinity less than about $10^{-2}$ M (e.g., from about $10^{-9}$ M to about $10^{-7}$ M) with a constituent of the biological hydrogels.

In some embodiments, the disclosure provides a method for trapping a foreign substance (e.g., a pathogen) in biological hydrogels. The method includes contacting the pathogen with an IgG or IgM antibody in an amount effective to trap the pathogen, wherein the antibody has a binding affinity less than about $10^{-2}$ M (e.g., between about $10^{-9}$ M and about $10^{-7}$ M) with a constituent of the biological hydrogels.

In some embodiments, the disclosure provides a method for preventing or treating an infection in a subject, wherein the infection is caused by a foreign substance (e.g., a pathogen) in an extracellular matrix of a basement membrane. The method includes/comprises administering to the subject in need thereof an effective amount of an IgG or IgM antibody, wherein the antibody has a binding affinity less than about $10^{-2}$ M (e.g., from about $10^{-9}$ M to about $10^{-7}$ M) with a constituent of the extracellular matrix. The extracellular matrix can be a biological hydrogel. The basement membrane can be an epithelium, such as respiratory tract or gastrointestinal tract.

In some embodiments, the Fc region of the antibodies described herein can bind to one or more constituents of the biological hydrogel and the Fab region of the antibodies described herein can bind to the surface of the pathogens.

In some embodiments, the disclosure provides an extracellular matrix complex or mixture, which includes/comprises a biological hydrogel, a plurality of IgG antibodies or IgM antibodies, a plurality of immobilized pathogens, wherein the Fc region of the plurality of IgG antibodies or IgM antibodies binds to a constituent of the biological hydrogel and the Fab region of the plurality of IgG antibodies or IgM antibodies binds to the surface of the plurality of pathogens to immobilize the plurality of pathogens, and wherein the plurality of IgG antibodies or IgM antibodies has a rate of binding to the plurality of pathogen greater than $10^4$ $M^{-1}$ $s^{-1}$ and a binding affinity less than about $10^{-2}$ M (e.g., from about $10^{-9}$ M to about $10^{-7}$ M) with the constituent of the biological hydrogel.

In some embodiments, the antibody can be formulated into a pharmaceutical composition suitable for intranasal, oral, intravaginal, by inhalation, or topical administration. The composition can be administered or delivered to a mucosal surface, a respiratory tract, a gastrointestinal tract or a skin surface.

In some embodiments, the disclosure provides a method for preventing or treating an infection in a subject, wherein the infection is caused by a foreign substance. The method includes applying a hydrogel to the subject and administering to the subject an effective amount of an IgG or IgM antibody, wherein the antibody has a binding affinity of less than about $10^{-2}$ M with a constituent of the hydrogel.

V. Contraception

One aspect of the invention relates to methods of contraception. One embodiment relates to a method of providing contraception, e.g., inhibiting fertilization, in a female subject, comprising administering to the mucosa of the reproductive tract, e.g., the vaginal and/or cervical mucosa, of the subject a crosslinker or composition of the invention in an amount effective to inhibit sperm-egg fertilization, and thus prevent pregnancy. In an additional embodiment, the method can be practiced on a male subject to trap sperm in the epydidimal mucus. In certain embodiments, the methods comprise additional steps such as one or more of isolating/preparing the crosslinkers, preparing a composition of the crosslinkers, determining the level of antibodies in the mucus of the subject before administering the crosslinkers, and determining the level of crosslinkers in the mucus of the subject after administering the crosslinkers.

The crosslinkers and compositions of the present invention according to the methods described herein are administered or otherwise applied by delivering the composition, typically to the reproductive tract. In some embodiments, the crosslinkers and compositions may be topically delivered. In other embodiments, the crosslinkers and compositions may be systemically delivered such that the crosslinkers are secreted into the mucus of the subject. Accordingly, the compositions as described above may be delivered to a mucosal surface of the reproductive tract, e.g., to the vulva, including the vaginal cavity. In the vaginal cavity, the compositions may be applied to any portion of the uterus, including inside the uterus and on the cervix, including the mucosa and/or lining of the endo- and ecto-cervix.

An effective amount of the crosslinker can be administered. As used herein, an "effective amount" of the crosslinker for contraception refers to a dosage sufficient to inhibit sperm from contacting an egg and fertilizing it. The effective amount can be an amount sufficient to trap an amount of the sperm in mucus. As will be recognized by one of skill in the art, the amount can vary depending on the subject. The exact amount that is required will vary from subject to subject, depending on the species, age, and general condition of the subject, the particular carrier or adjuvant being used, mode of administration, and the like. As such, the effective amount will vary based on the particular circumstances, and an appropriate effective amount can be determined in a particular case by one of skill in the art using only routine experimentation. In some instances, an effective amount of crosslinker can be an amount that achieves a concentration of crosslinker in the mucus of about 0.1 µg/mL to about 1000 µg/mL, e.g., about 0.5 µg/mL to about 100 µg/mL, e.g., about 1 µg/mL to about 50 µg/mL or any range therein.

As will be recognized by one of skill in the art, the term "inhibiting" or "inhibition" does not refer to the ability to completely eliminate the possibility of fertilization in all cases. Rather, the skilled artisan will understand that the term "inhibiting" refers to reducing the chances of sperm moving through mucus beyond the mucus membrane such that fertilization of a subject can occur, such as reducing chances of fertilization by a sperm when such sperm is bound to trapping crosslinkers in mucus. Such decrease in fertilization potential can be determined relative to a control that has not been administered the crosslinkers of the invention. In some embodiments, the decrease of fertilization relative to a control can be about a 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% decrease.

In some embodiments providing contraception in a subject can comprise trapping sperm in mucus. As such, in some embodiments a method of trapping sperm in mucus is provided, which method includes administering to a mucosa in the reproductive tract of the subject a crosslinker or composition as described herein.

As used herein, the term "subject" refers to humans and other animals. Thus, veterinary treatment is provided in accordance with the presently-disclosed subject matter. As such, the presently-disclosed subject matter provides for the treatment of mammals such as humans, as well as those mammals of importance due to being endangered, such as Siberian tigers; of economic importance, such as animals raised on farms; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Thus, also provided is the treatment of livestock, including, but not limited to, domesticated swine, ruminants, ungulates, horses (including race horses), poultry, and the like.

In particular embodiments of the invention, more than one administration (e.g., two, three, four, or more administrations) of the crosslinker, composition, or device comprising the composition can be employed over a variety of time intervals (e.g., hourly, daily, weekly, monthly, etc.) to achieve prophylactic/contraceptive effects. In some embodiments, the crosslinker, composition, or device is administered regularly or constantly. In other embodiments, the crosslinker, composition, or device is administered on an as needed basis, e.g., prior to sexual activity and/or following sexual activity.

In some embodiments, the method include administering an crosslinker, and further administering an additional active agent, e.g., prophylactic or therapeutic agent, e.g., a sperm-function inhibitor and/or an antimicrobial, such as an antibiotic, an antiviral, or other antimicrobial as would be known to one of skill in the art. The additional active agents can be delivered concurrently with the crosslinkers and compositions of the invention. The additional active agents can be delivered in the same composition as the crosslinker or in separate compositions. As used herein, the word "concurrently" means sufficiently close in time to produce a combined effect (that is, concurrently can be simultaneously, or it can be two or more events occurring within a short time period before or after each other).

VI. In Vitro Uses

Having demonstrated the usefulness of the crosslinkers of the invention in trapping a target of interest on a substrate of interest, another aspect of the invention relates to in vitro uses of the crosslinkers to manipulate a target of interest. The crosslinkers may be used in any method or technique where noncovalent binding of a target to a substrate is desired. Examples include, without limitation, methods of separating, purifying, washing, filtering, or otherwise manipulating a target by using a crosslinker to trap the target on a substrate, which may be, e.g., part of a chromatography, dialysis, or filtration medium. In some embodiments, the substrate of interest may be contacted with the crosslinker and then a composition comprising the target of interest may be added to the substrate, e.g., as part of column chromatography or patch chromatography.

In some embodiments, the crosslinker of the invention may be used in a method or assay in which it is desirable to trap a target of interest on a substrate of interest. Examples include, without limitation, purification methods, filtration methods, separation methods, immunoassays and other detection assays.

VII. Computer Programs and Systems

The present invention also provides a computer program product comprising: a computer readable storage medium having computer readable code embodied in the medium, the computer code comprising: computer readable code to perform operations to carry out the methods of this invention.

Further provided herein is a computer system, comprising: a processor; and a memory coupled to the processor, the memory comprising computer readable program code embodied therein that, when executed by the processor, causes the processor to perform operations to carry out the methods of this invention.

As noted above, a kit of this invention can comprise electronic hardware components. In some embodiments of this invention, the electronic hardware may perform and/or support functionality that corresponding to various operations described herein. For example, functions described and/or illustrated in diagrams and/or flowchart illustrations of methods, apparatus (systems) and/or computer program products according to some embodiments may be performed by the electronic hardware. It is understood that each block of the block diagrams and/or flowchart illustrations, and combinations of blocks in the block diagrams and/or flowchart illustrations, can be implemented by computer program instructions. These computer program instructions may be provided to a processor of a general purpose computer, special purpose computer, and/or other programmable data processing apparatus to produce a machine, such that the instructions, which execute via the processor of the computer and/or other programmable data processing apparatus, create means for implementing the functions/acts specified in the block diagrams and/or flowchart block or blocks.

These computer program instructions may also be stored in a computer-readable memory that can direct a computer or other programmable data processing apparatus to function in a particular manner, such that the instructions stored in the computer-readable memory produce an article of manufacture including instructions which implement the function/act specified in the block diagrams and/or flowchart block or blocks.

The computer program instructions may also be loaded onto a computer or other programmable data processing apparatus to cause a series of operational steps to be performed on the computer or other programmable apparatus to produce a computer-implemented process such that the instructions which execute on the computer or other programmable apparatus provide steps for implementing the functions/acts specified in the block diagrams and/or flowchart block or blocks.

Accordingly, the present invention may be embodied in hardware and/or in software (including firmware, resident software, micro-code, etc.). Furthermore, embodiments of the present invention may take the form of a computer program product on a computer-usable or computer-readable non-transient storage medium having computer-usable or computer-readable program code embodied in the medium for use by or in connection with an instruction execution system.

The computer-usable or computer-readable medium may be, for example but not limited to, an electronic, optical, electromagnetic, infrared, or semiconductor system, apparatus, or device. More specific examples (a non-exhaustive list) of the computer-readable medium would include the following: an electrical connection having one or more wires, a portable computer diskette, a random access memory (RAM), a read-only memory (ROM), an erasable programmable read-only memory (EPROM or Flash memory), an optical fiber, and a portable compact disc read-only memory (CD-ROM).

Computer program code for carrying out operations for aspects of the present disclosure may be written in any combination of one or more programming languages, including an object oriented programming language such as Java, Scala, Smalltalk, Eiffel, JADE, Emerald, C++, C#, VB.NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computer environment or offered as a service such as a Software as a Service (SaaS).

Having described the present invention, the same will be explained in greater detail in the following examples, which are included herein for illustration purposes only, and which are not intended to be limiting to the invention.

EXAMPLE 1

Mathematical Modeling

Materials and Methods

Similar to previous studies (McKinley et al., *PLoS One* 9:e100598 (2014); Chen et al., *Biophys. J.* 106:2028 (2014); Geonnotti et al., *Biophys. J.* 91:2121 (2006); Lai et al., *Biophys. J.* 97:2379 (2009)), we modeled the diffusion of HIV from a virion-rich ($8.4 \times 10^5$ virions, the average viremia in semen of acutely infected males (McKinley et al., *PLoS One* 9:e100598 (2014); Gupta et al., *J. Virol.* 71:6271 (1997))) semen layer (volume ~3.0 mL (Rehan et al., *Fertil. Steril.* 26:492 (1975))) uniformly deposited on top of a cervicovaginal mucus layer (CVM) that evenly covers the entire vaginal epithelial cell layer. This results in a thickness of d=200 µm and L=50 µm for the semen and CVM layers, respectively. Broadly neutralizing Ab accumulate on HIV virions at rates depending on Ab-antigen affinity, the number of available antigen sites on the virus surface, and the local Ab concentration. For a model monoclonal broadly neutralizing Ab against HIV, we focused on NIH45-46, which binds to the CD4 binding site of gp120 and whose binding affinities were previously described (Scheid et al., *Science* 333:1633 (2011)). The number of Env spikes $N^*$ on individual HIV virions is variable, and was estimated to follow a negative binomial distribution with $N^*=14\pm7$ (range 4-35) based on cryo electron microscopy of HIV virions (Zhu et al., *Nature* 441:847 (2006). We assume each Env spike can bind up to 3 Ab without significant steric hindrance; thus, individual Ab at concentration u(z,t) can bind and unbind independently with rates $k_{on}$ and $k_{off}$, and overall binding/unbinding rates dependent on the number of unoccupied binding sites $3N^*-n$. However, since the diffusivity for a mucin-bound Ab $u_b(z,t)$ is reduced compared to free individual Ab, the Smoluchowski encounter rate implies that the binding rate for a mucin-bound Ab ($k'_{on}$) to its antigen should be reduced proportional to the difference in diffusivities of the Ab ($D_{Ab}$) and the virus ($D_v$); hence, $$k'_{on} = \frac{D_v}{D_{Ab} + D_v} k_{on} \approx \frac{1}{25} k_{on}.$$

The Ab-virion binding rate equations can be summarized as.

$$(Ab) + (Ab)^n Z(t) \underset{(n+1)k_{off}}{\overset{(3N_* - n)(k^f_{on} u_f(Z(t),t) + k^b_{on} u_b(Z(t),t))}{\rightleftharpoons}} (Ab)^{n+1} Z(t) \quad (1)$$

where (Ab) is an unbound Ab and $(Ab)^n Z(t)$ denotes a virion at $Z(t)$ with n bound Ab. Individual Ab also bind and unbind to mucins at rates $m_{on}[M]$ and $m_{off}$, where [M] is the effective concentration of Ab binding sites in the mucin network. In addition, virion-bound Ab may also associate with mucins, effectively immobilizing the entire Ab-virion complex for the duration of the interaction.

We developed two different methods to simulate HIV penetration across the vaginal mucosa. In the first method, a stochastic particle simulation was used for virion diffusion, virion-Ab binding, and Ab-mucin interactions. Virion diffusion for a particle Z is given by the stochastic differential equation (SDE)

$$dZ = \sqrt{2D} dW$$

where W is Brownian motion and $$D = \begin{cases} D_{HIV}, & \text{free} \\ 0, & \text{bound} \end{cases},$$

where "free" indicates that all virion-bound Ab are free from mucin, and "bound" indicates that at least 1 virion-bound Ab is associated to mucin. Ab binding and unbinding to virus is simulated with a Poisson random variable with rates given by (1). Lastly, Ab-mucin interactions were simulated with Poisson random variables and rates dependent on the total number of virion-bound Ab and those Ab currently interacting with mucins. Due to the great computational expense involved in simulating Ab-mucin interactions particularly when $m_{on}[M] > m_{off}$, we precomputed lookup tables giving the distributions for the time that a virion spends freely diffusing and the time that a virion spends interacting with mucins. The (random) time that a virion spends freely diffusing is given by the first time that at least one of its associated Ab binds to mucin. Similarly, the time that a virion spends interacting with mucins is given by the time that at least one of the virion-bound Ab associates with mucin until the first time that none of the surface bound Ab associates with mucin. We then sample from these lookup tables whenever a virion's state changes (freely diffusing or bound to mucin, binding or unbinding an Ab, crossing the semen/CVM interface).

The second simulation method consists of a reaction-diffusion partial differential equation (PDE) to capture the average behavior of the virus population. The virus population is represented by a vector $$\overset{1}{V}(z, t),$$

where the component $V_n(z,t)$ represents the concentration of virus with n bound Ab. We previously introduced a parameter $$\alpha = \frac{m_{off}}{m_{off} + [M]m_{on}}$$

to represent the fraction of time that Ab in CVM spend freely diffusing [21]. Since Ab-mucin interactions likely occur at fast time-scales, $$u_f(z, t) = \begin{cases} \alpha u(z, t), & 0 < d < 50 \\ u(z, t), & 200 < d < 250 \end{cases}, \text{ and } u_b(z, t) = u(z, t) - u_f(z, t).$$

In the limit $m_{on}$, $$m_{off} \to \infty \ (\text{keeping} = \frac{m_{off}}{m_{off} + [M]m_{on}}$$

fixed), the stochastic model can thus be approximated by the reaction-diffusion system:

$$\frac{\partial \overset{r}{V}}{\partial t} = D \frac{\partial^2 \overset{r}{V}}{\partial z^2} - \overset{r}{f}(\overset{r}{V}(z, t)) + \overset{r}{g}(\overset{r}{V}(z, t)),$$

$$\frac{\partial u}{\partial t} = D_{Ab0} \frac{\partial^2 u}{\partial z^2},$$

where the diffusion tensor D, is a diagonal tensor with entries $D_{v_0}$, $\beta_1 D_{v_0}$, . . . , $\beta_{3N*} D_{v_0}$ along the diagonal (the diffusion factors $\alpha_i$ are determined below) for 0<d<50 and diagonal entries all $D_{v_0}$ for 50<d<250; and $$D_{Ab} = \begin{cases} \alpha D_{Ab0}, & 0 < d < 50 \\ D_{Ab0}, & 50 < d < 250 \end{cases}.$$

We use a FTCS algorithm to model diffusion for both the virus and Ab populations, with reflecting boundary conditions at the semen/lumen interface; reflecting conditions for Ab and absorbing conditions for virus at the CVM/cell interface; and Fick's law for the discontinuous diffusion coefficients at the semen/CVM interface. We assume that the number of Ab binding to virions is negligible compared to the overall Ab population, so there are no local depletion effects.

If each virion-bound IgG binds and unbinds to the mucin mesh independently, then the virion spends approximately a fraction $\alpha^n$ of time with all its bound Ab simultaneously free from mucin. This yields a time-averaged diffusivity $D_{vn} = \alpha^n D_{vO}$ in the CVM. One adjustment is made, however, to account for the lower diffusivity of a virion-Ab complex compared with an individual Ab. Similar to the adjustments on $k_{on}$, we define $$m^{first} = \frac{1}{30},$$

so that initial Ab-mucin encounters occur at rate $m^{first}m_{on}$ [M]. For subsequent interactions of virion-bound Ab with mucin, the rate may increase because the Ab-virus complex is already located in close proximity to a mucin molecule, or may be decreased due to the reduced diffusivity of the Ab-virus complex associated to mucins relative to a non-associated Ab-virus complex. Due to the lack of empirical data in the literature, we assumed other Ab-bound to the same virion with at least one Ab already associating with mucins will associate with mucins with the same mucin-binding kinetics as a free Ab molecule. In order to calculate the diffusion factors $\beta_1, \beta_2, \ldots \beta_{3N}$, first neglect the factor $m^{first}$ and consider the total time free$_i$ that a virion with i bound Ab spends freely diffusing and the total time bound, that it spends bound to mucins up to a time T. Since the Ab are assumed to bind and unbind to mucin independently, $$\lim_{T \to \infty} \frac{\text{free}_i}{\text{free}_i + \text{bound}_i} = \alpha^i.$$

Now $$\beta_i = \frac{m^{first}\text{free}_i}{m^{first}\text{free}_i + \text{bound}_i} =$$

$$\frac{m^{first}\text{free}_i/(\text{free}_i + \text{bound}_i)}{(m^{first} - 1)\text{free}_i/(\text{free}_i + \text{bound}_i) + 1} = \frac{m^{first}\alpha^i}{(m^{first} - 1)\alpha^i + 1}.$$

The stochastic simulations and the reaction-diffusion simulations show excellent agreement, particularly at rapid $m_{on}$[M] and $m_{off}$ (FIG. 7). Hence we utilized the deterministic simulations except where noted.

Determining the number of Ab required to neutralize a given HIV remains an active area of research, due to the difficulty in simultaneously distinguishing the number of Ab necessary to neutralize a particular Env spike and the minimum number of Ab-free Env spike necessary for HIV to successfully infect (Magnus et al., *PLoS Comput Biol* 6:e1000713 (2010)). It was previously proposed that the binding of a single Ab molecule to an Env spike appear to be sufficient to inactivate the infectivity associated with that spike (Yang et al., *J. Virol.* 79:3500 (2005)). The minimum number of Ab-free Env spikes, and consequently the number of Env spikes that must be inactivated to neutralize a virion, remain more controversial. Estimates for minimum infectivity ranged from a single Ab-free Env spike (Yang et al., *J. Virol.* 79:3500 (2005)) to many (Schonning et al., *J. Virol.* 73:8364 (1999); McLain et al., *J. Gen. Virol.* 75 (Pt 6):1457 (1994)). For our current model, we assume that each additional Ab binding to a previously unoccupied Env incrementally reduces the likelihood of infection, and we measure the overall reduction in infectivity by the reduction in number of unoccupied Env arriving at the vaginal epithelium over the first two hours post ejaculation.

Results

Incorporating Mucin-Binding Kinetics into Previous Models for HIV Penetration of Ab-Laden CVM:

We have previously modeled the diffusion of HIV through CVM by combining a stochastic/deterministic hybrid model for the one dimensional Brownian movement of individual HIV virions together with a continuum model that describes the average local concentration of broadly neutralizing monoclonal IgG in CVM (Chen et al., *Biophys. J.* 106:2028 (2014)). That model allowed us to show that a multitude of weak bonds between virion-bound IgG and mucins alone, defined by the ratios of IgG diffusion in mucus vs. buffer ($\alpha$) in the range of 0.8-0.9, is sufficient to immobilize the vast majority of HIV near the semen/CVM interface. Nevertheless, to further explore the IgG trapping potency across the full range of IgG-mucin affinity, it was necessary to incorporate additional complexity into the model. First, when modeling IgG that binds more tightly to mucins, we made the assumption that the probability of a successful bond between an IgG and the corresponding viral antigen is directly proportional to the overall collision frequencies between the two bodies, which can be described by the classical Smoluchowski principle (Lai et al., *Proc. Natl. Acad. Sci. USA* 107:598 (2010)). Since an IgG bound to mucins will process far reduced range of motion than a free, unbound IgG molecule, the bound IgG should process a reduced $k_{on}$ rate, denoted as $k_{on}'$, proportional to the reduction in collision frequency with viral antigen, which in turn can be approximated by the ratios of the diffusivity of IgG vs. mucins in CVM. While the diffusivity of individual mucins in CVM remains unknown, we have previously shown that CVM is composed of heavily bundled mucins that likely reflect exceedingly limited range of motion for individual mucins (Lai et al., *Proc. Natl. Acad. Sci. USA* 107:598 (2010)). We thus made a very conservative estimate that an IgG bound to mucin will possess a 25-fold reduced $k_{on}$ rate compared to individual free IgG (i.e. $k_{on}' = k_{on}/25$), which roughly equates to assuming the range of motion of mucins to match that for individual HIV virions. While obviously an over-conservative assumption, further reduction in $k_{on}'$ does not meaningfully impact estimates generated by our model.

A second important detail we incorporated into our model is the kinetics of IgG binding to and unbinding from mucins, which we termed $m_{on}$ and $m_{off}$, respectively. Experimentally, $m_{on}$ and $m_{off}$ appears to be extremely transient and difficult to measure individually (Saltzman et al., *Biophys. J.* 66:508 (1994); Olmsted et al., *Biophys. J.* 81:1930 (2001)). Instead, IgG-mucin affinity is inherently reflected by the diffusion coefficients of IgG in CVM vs. in buffer, which we denote as $\alpha$. $\alpha$ reflects the fraction of bound vs. unbound IgG at any moment in time, and is equivalent to the ratio $m_{off}/(m_{off} + m_{on})$ at steady state. Assuming IgG binding to its antigen does not increases its affinity to mucins, the rates with which individual IgG can bind to mucins must be far faster than the rate of virion-associated IgG binding to mucins. We thus introduced a correction factor of ~30 for the mucin-association kinetics for virion-bound IgG, which is equivalent to the difference in diffusivities of HIV vs. IgG in CVM. This correction was necessary to ensure we do not overestimate the trapping potency of viruses.

Figure 2:
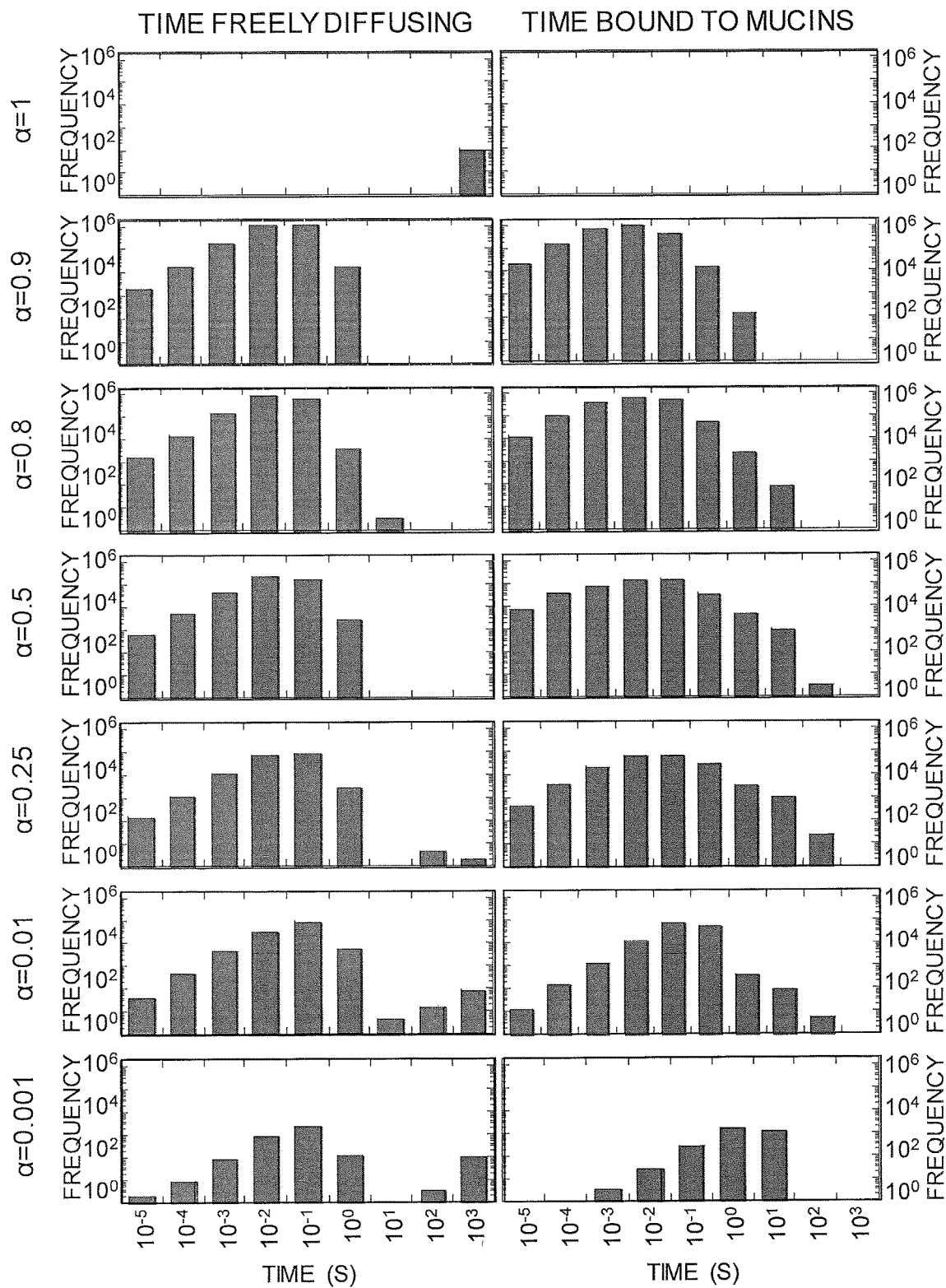
FIG. 2 shows the distribution of time viruses spend freely diffusing or associated with mucins in CVM containing 10 μg/mL of NIH45-46 with different affinity to mucins, ranging from no affinity at α=1 to very strong affinity at α=0.001. In this simulation, Ab are allowed to accumulate on HIV for 30 mins first prior to measuring the time of free diffusion or association with mucins for the subsequent 90 mins.
Figure 3A:
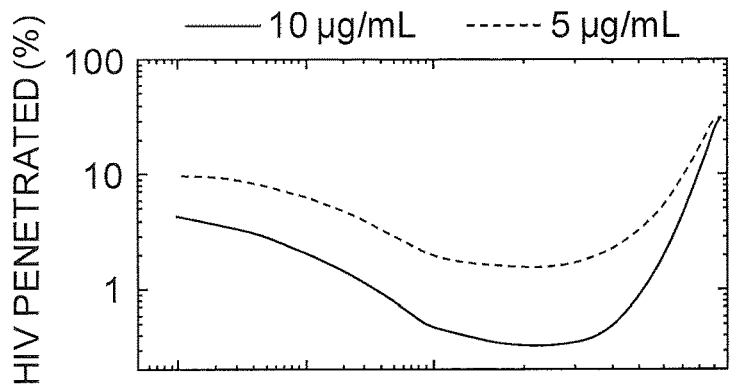
FIGS. 3A-3D show the predicted trapping potency and protection by 5 μg/mL and 10 μg/mL of NIH45-46 with varying affinity to mucins as characterized by a, which reflects the ratio of the diffusion coefficients of the monoclonal IgG in mucus vs. water. (A) Predicted fraction of HIV load initially in semen that can diffuse across CVM containing NIH45-46 over the first two hours post-deposition. (B) Average number of NIH45-46 bound to HIV arriving at the vaginal epithelium. Values below 1 represent HIV that arrive at the vaginal epithelium without any bound NIH45-46. (C-D) Extent of NIH45-46-mediated protection, as quantified by infectivity relative to (C) no NIH45-46 present in CVM, or (D) the same amount of N1H45-46 present but without any affinity to mucins.
Figure 3B:
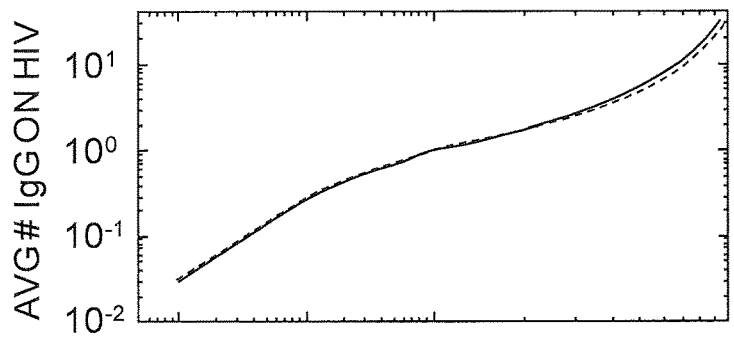
Figure 3C:
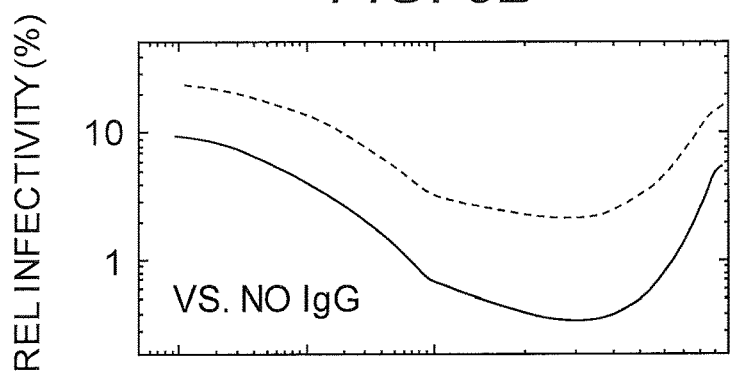
Figure 3D:
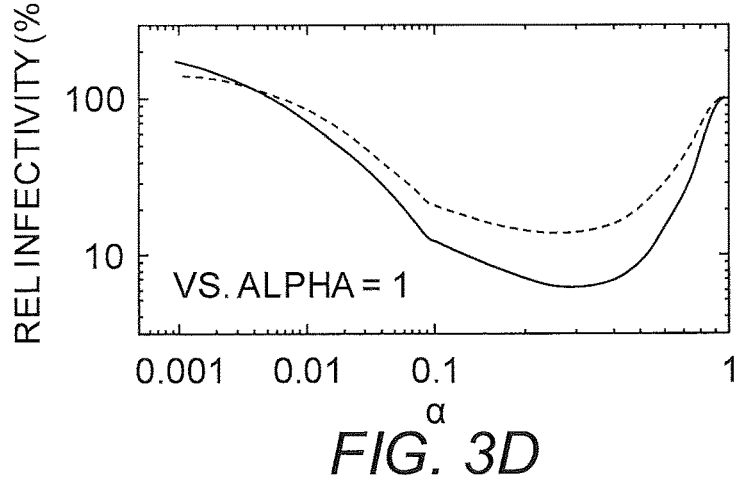

As a first step towards understanding how IgG-mucin affinity can impact trapping potency, we modeled the probability and duration of HIV-IgG complex associating to mucins in CVM containing 10 µg/mL NIH45-46 with varying IgG-mucin affinity. Naturally, HIV with surface IgG possessing no affinity to mucins, defined by $\alpha=1$, never binds to mucins, and the HIV-IgG complex undergoes free diffusion the entire duration (FIG. 2A). When IgG-mucin affinity is slightly increased such that individual IgG would associate with mucins ~5 and 10% of the time (i.e. $\alpha=0.95$ and 0.9, respectively), the fraction of time an HIV-IgG complex spends freely diffusing in mucus begins to decrease, with a corresponding increase in the fraction of time spent associated with mucins (FIGS. 2B-2C). Interestingly, the fraction of time the HIV-IgG complex associates with mucins appears to peak between $\alpha=0.1$ and 0.25 (FIGS.

Figure 6:
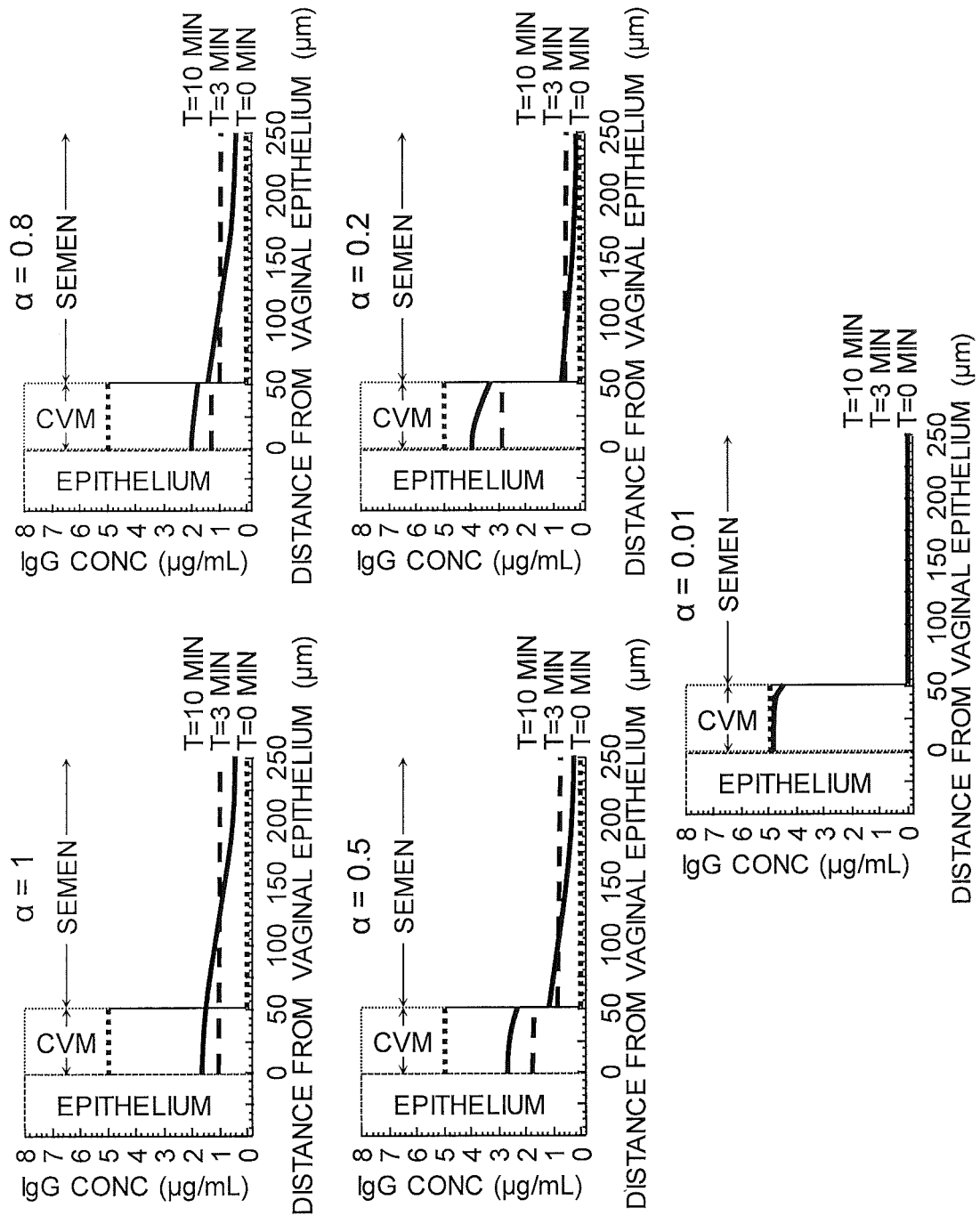
FIG. 6 shows IgG profiles in genital secretions overlaying the vaginal epithelium over time for IgG with distinct affinity to mucins.

2D-2F). This is attributed to the fact that increased IgG-mucin affinity (i) markedly reduces the fraction of NIH45-46 that can freely diffuse and readily bind to HIV, especially in the semen layer far away from the vaginal epithelium (FIG. 6), and (ii) that mucin-associated IgG captures HIV with far lower efficiency (i.e., reduced $k_{on}$' vs. $k_{on}$). These two factors together increases number of HIV with no bound IgG. With further increases of mucin affinity to $\alpha=0.01$, the amount of HIV free of bound IgG dominates relative to HIV-IgG complexes, and most HIV again undergo Brownian motion in CVM (FIG. 2G).

Influence of IgG-Mucin Affinity on Maximizing Trapping Potency and Vaginal Protection:

We next quantified how the probability of HIV-mucin association impacts the fraction of HIV that can penetrate CVM and reach the underlying vaginal epithelium, and the corresponding reduction in infectivity based on the decrease in HIV-Env free of bound IgG on those virions (McKinley et al., *PLoS One* 9:e100598 (2014)). In good agreement with the estimate of the fraction of time spent associated with mucins, the maximum reduction in HIV flux reaching the vaginal epithelium peaks at IgG-mucin affinities corresponding to α=0.25 (FIG. 3A). At 5 and 10 μg/mL of NIH45-46 initially present in CVM and an IgG-mucin affinity equivalent to α=0.25, only ~3% and ~0.3% of the HIV viral load in semen is predicted to reach the vaginal epithelium over the first 2 hrs post-ejaculation, equating to 10 to 100-fold reduced flux compared to the estimated ~30% of HIV load over the same duration in the absence of IgG-mucin affinity (FIG. 3A). Under this scenario, each HIV virion on average possesses ~2 bound IgG (FIG. 3B), and the overall infectivity is reduced by 86-94% (i.e. ~7-16 fold) compared to IgG without affinity to mucins (FIGS. 3C-3D). Note that the reduction in infectivity is less than the reduction in flux of HIV viruses since NIH45-46 without affinity to mucins can still neutralize the virus.

When IgG-mucin affinity is further increased (i.e. lower α), the fraction of HIV reaching the vaginal epithelium began to increase. Furthermore, there is also substantially less number of IgG bound to HIV-Env on virions that reach the vaginal epithelium. Indeed, when a drops below 0.1, on average less than one IgG molecule is bound on each virion over the entire population of HIV, which implies that there must be HIV virions without any bound IgG (FIG. 3B). As a result, infectivity of HIV may actually be greater for hypothetical NIH45-46 that can bind tightly to mucins than if NIH45-46 possessed no mucin-affinity at all (FIGS. 3C-3D).

To begin to understand how to engineer more potent HIV-trapping IgG, we evaluated the relative impact of the rate of IgG binding to the virus surface compared to IgG-mucin affinity. The rate of IgG binding to HIV is the product of both the local IgG concentration and $k_{on}$, the binding kinetic constant: a doubling of IgG $k_{on}$ has the same impact on IgG binding to HIV as doubling the IgG concentration. The reduction of HIV flux arriving at the vaginal epithelium, and the reduction in mean number of NIH45-46-free Env proteins on HIV that reached the vaginal epithelium, were sensitive to both IgG-antigen binding rate and IgG-mucin affinity (FIGS. 4A-4D). When IgG-mucin affinity is increased, the amount of initial NIH45-46 in CVM needed to reduce the flux of viruses arriving the vaginal epithelium by 50% was reduced from 5-35+ μg/mL for α=0.8-0.9 (in the range to what was previously measured for IgG) to <1 μg/mL when α=0.25 (FIG. 4A). Similarly, the amount of NIH45-46 needed to reduce the mean number of NIH45-46-free Env proteins on HIV by 80% was reduced from 22-35+ μg/mL for α=0.8-0.9 to 3 μg/mL for α=0.25 22-35+ μg/mL to 3 μg/mL (FIGS. 4C-4D). Overall, the amount of NIH45-46 needed to reduce infectivity by 90% was reduced from ~5-6 μg/mL when α=1 to 2 μg/mL when α=0.25 5-6 μg/mL to 2 μg/mL.

Influence of IgG-Antigen Binding Affinity on Maximizing Trapping Potency and Vaginal Protection:

A longstanding assumption for neutralizing IgG against HIV and other viruses is that higher binding affinity between IgG and viral antigen would facilitate more potent protection. However, it is important to note that high affinity IgGs are typically identified and selected based on neutralization assays, typically in the absence of mucus coatings and with some incubation time between virus and IgG prior to exposure of the virus to target cells. Thus, we sought to quantitatively evaluate whether high antigen-IgG affinity that typically maximizes neutralization potency in vitro would also be maximally protective against mucosal HIV transmission in our model.

Interestingly, we found that the antigen-unbinding rate $k_{off}$ generally possessed only a very minor effect on increasing the fraction of HIV load that is trapped in mucus or facilitate more effective protection, especially when the IgG concentration or the $k_{on}$ rate is low (FIG. 5A). For example, at 1 μg/mL of IgG with $k_{on}$ of $1.5\times10^4$ $M^{-1}$ $s^{-1}$ ($k_{on}[Ab]=10^{-4}$ $s^{-1}$), improvements of $k_{off}$ from $10^{-3}$ $s^{-1}$ to $10^{-4}$ $s^{-1}$ only reduced the HIV flux arriving the vaginal epithelium by 1.6%, and a further improvement from $10^{-4}$ $s^{-1}$ to $10^{-5}$ $s^{-1}$ essentially resulted in no appreciable difference in reduction of flux (FIG. 5A). This is similarly reflected by the change in the infectivity of the viruses relative to IgG with no mucin-affinity from 100% with $k_{off}=10^{-3}$ $s^{-1}$ to 96% with $k_{off}=10^{-4}$ $s^{-1}$ to finally 92% with $k_{off}=10^{-5}$ $s^{-1}$ (FIGS. 5C-5D). The lack of impact by $k_{off}$ is directly attributed to the exceedingly limited number of IgG that can accumulate on the surface of HIV when IgG is present either at low to modest concentrations, or when IgG possesses inadequate binding kinetics (FIG. 5B); slower unbinding kinetics simply cannot enhance HIV trapping in mucus or neutralization when few or no IgG is bound to HIV in the first place.

A hallmark of HIV is its exceptionally high mutation rates, which enables the virus to readily escape antibodies generated by the immune system and prevent the host from mounting a protective immune response. Comprehensive studies of elite controllers—the rare individuals who can maintain undetectable viral load without antiretroviral therapy—led to the discovery and cloning of monoclonal antibodies that can broadly neutralize the vast majority of HIV strains. These broadly neutralizing antibodies (bnAbs) were thought to provide a template for the development of an HIV vaccine. Unfortunately, HIV vaccine, including those that could block vaginal transmission of HIV, remains elusive to date, likely because of at least two reasons. First, bnAbs are typically highly somatically mutated, and vaccines may not be able to elicit the extent of somatic hypermutation needed in most individuals to generate the desirable bnAbs. Second, many HIV vaccine candidates are based on DNA or subunit proteins rather than attenuated virus; the durability of antibody response from subunit vaccines are generally shorter than vaccines based on attenuated virus, and the level of antibody titers induced in the vagina may be inadequate to block vaginal HIV transmission.

To overcome the challenges with HIV vaccines, a recently emerged strategy is to enable passive immunization of the vagina via sustained delivery of bnAbs locally (Whaley et al., *J. Infect. Dis.* 210 Suppl 3:S674 (2014); Sherwood et al., Nat. Biotechnol. 14:468 (1996)). By dosing the bnAbs directly into the vagina, this strategy not only bypasses the limitations of somatic hypermutation, but also ensures protective levels of bnAbs are present in the vagina to block HIV transmission. Despite these important advantages, a critical shortcoming for passive immunization is the relatively high costs of maintaining protective levels of antibody in the body compared to vaccination. Much effort has been spent on reducing the costs of antibody production, such as the production of antibodies in plants (Ramessar et al., *Proc. Natl. Acad. Sci. USA* 105:3727 (2008); Whaley et al., Hiatt A, Zeitlin L (2011) Emerging antibody products and *Nicotiana* manufacturing. Hum. Vaccin. 7:349 (2011)) as well as cheaper and more efficient methods of purifying antibodies (Liu et al., MAbs 2:480 (2010); Zydney, *Biotechnol. Bioeng.* 113:465 (2016)). Here, we introduce a novel and completely distinct approach—based on tuning IgG-mucin interactions—that could markedly reduce the dose of bnAbs needed to block vaginal HIV transmission. The majority of bnAbs against HIV appear to possess $k_{on}$ in the range of $10^4$ $M^{s-1}$ that we previously estimated may require concentrations in excess of 5-10 µg/mL to facilitate effective protection. Although we predict enhanced vaginal protection can be accomplished with both increasing $k_{on}$ and optimizing IgG-mucin affinity, the bnAbs generally bind to a very unique epitope on HIV-Env that makes it unlikely to substantially improve the bnAbs $k_{on}$ without compromising binding affinity (i.e. higher $k_{off}$). In contrast, simply by tuning the interactions between IgG-Fc and mucins, we can potentially reduce dose of bnAb for effective protection by 10-fold or more without jeopardizing the broad antigen coverage of bnAb. Optimizing IgG-Fc interactions with mucins thus offers a promising strategy to markedly reduce the costs for effective passive immunization of the vagina. The convergence of these various approaches may synergistically drive down the costs and make passive immune protection against HIV cost effective even in resource-poor settings.

Surprisingly, high affinity IgG-mucin interactions did not appear to enhance protection. Instead, the ideal IgG-mucin affinity that maximizes protection in our model ($\alpha$~0.25) is comparable to the mucin-affinity previously measured for IgM molecules (Saltzman et al., *Biophys. J.* 66:508 (1994); Olmsted et al., *Biophys. J.* 81:1930 (2001)). It is also worth noting that IgM, due to its pentameric structure, has 10 Fab arms compared to 2 Fab arms for each IgG, and hence can bind to its antigenic target and accumulate on the surface of virions with exceptional speed even if each Fab possess relatively poor affinity compared to a fully affinity-matured IgG. Thus, an IgM molecule appears to simultaneously satisfy both design requirements we have identified in this study—rapid $k_{on}$ and modest mucin affinity. IgM is the first antibody isotype produced by our immune system and appears early in the course of an infection. Virus-specific IgM also usually reappear upon re-infection. While speculative, our study raises the hypothesis that an evolved effector function of IgM is to quickly begin purging a new pathogen from mucosal surfaces that likely represents its first site of infection early in the course of infection, and minimizing the viral titers that can enter the systemic circulation.

As discussed above, it is unlikely that we can markedly improve the $k_{on}$ for bnAbs without potentially compromising their broad antigenic coverage. An alternative method to enhance the overall rate of IgG accumulating on the viral surface at mucosal secretions is to include IgGs targeting other viral epitopes, including potentially non-neutralizing epitopes, since trapping virions in mucus require only binding and not necessarily neutralizing IgG. It is important to note that the immune system typically generates a polyclonal Ab response against diverse epitopes, rather than solely a neutralizing Ab response against a single viral epitope. Indeed, many of the naturally produced IgG against HIV found in HIV patients associate with either the lipid membrane of HIV virions, or other parts of the gp120 site on the Env spike not directly involved in HIV infection of immune cells (Santra et al., *PLoS Pathog.* 11:e1005042 (2015)). Likewise, virtually all of the IgGs detected in the moderately successful RV144 trial were non-neutralizing (Rerks-Ngarm et al., *N. Engl. J. Med.* 361:2209 (2009)). Such polyclonal response would likely result in substantially faster rate of Ab accumulation than an individual monoclonal IgG. Thus, co-delivery of multiple IgGs to enhance passive immune protection of the vagina, or inclusion of multiple immunogens (including non-neutralizing epitopes) in vaccine formulations, would both be harnessing the same strategy our immune system has evolved to fend off foreign pathogens.

Although often under-appreciated, CVM represents the first line of defense against sexually transmitted infections in the female reproductive tract. In addition to minimizing trauma to the vaginal epithelium upon coital stirring, the presence of the CVM layer also prevents virions in semen from immediately contacting the vaginal epithelium upon ejaculation, and directly reduces the virion flux and total viral load in semen that can reach target cells over time. Reinforcing the CVM barrier against sexually transmitted viral infections using virus-specific Ab that trap viruses in mucus is likely an important mechanism of the vaginal mucosal defense, but which is largely underappreciated and continues to be underexplored. We expect the combination of quantitative, predictive models with experimental validation will enable development of improved passive immunization as well as vaccination methods that harness the mucus barrier to reinforce the mucosal defense against HIV and other sexually transmitted infections.

EXAMPLE 2

Anti-PEG Antibodies Alter the Mobility and Biodistribution of Densely PEGylated Nanoparticles in Mucus An emerging mechanism of mucosal immune protection, pioneered by our group, is the immobilization of individual viruses due to antibody-mucin interactions, which in turn prevents viral translocation across mucus (Wang et al., *Mucosal Immunol.* 7:1036 (2014)). Previous work has shown that the interactions between antibodies and mucus are low-affinity and transient; for example, the diffusion of IgG and IgA molecules (diameter ~10 nm) in human mucus (pores ~340±50 nm (Lai et al., *Proc. Natl. Acad. Sci. USA* 107:598 (2010))) is slowed only ~5%-20% compared to in buffer (Olmsted et al., *Biophys. J.* 81:1930 (2001); Wang et al., *Mucosal Immunol.* 7:1036 (2014)). We found that this seemingly negligible affinity is sufficient to trap HSV-1 virions in human cervicovaginal mucus (CVM) with sub-neutralizing potency, presumably because the array of virion-bound IgG ensures a sufficient number of transient low-affinity bonds between the virus/IgG complex and mucins at any given time (Wang et al., *Mucosal Immunol.* 7:1036 (2014)). Furthermore, a non-neutralizing IgG facilitated effective protection against vaginal Herpes infection in mice, but that protection was abolished when vaginal mucus was removed. These results indicate that virus-binding antibodies in mucus can directly alter the mobility of virions in mucus, leading to a markedly reduced flux arriving at the epithelium (Chen et al., *Biophys. J.* 106:2028 (2014)). We thus sought to evaluate here whether anti-PEG antibodies in mucus would similarly trap PEGylated nanoparticles in mucus and impede therapeutics delivery to mucosal surfaces.

Methods

Mouse Cervicovaginal Mucus Collection:

Mouse cervicovaginal mucus (mCVM) was obtained from 6-8 week old CF-1 mice (Harlan, Frederick, Md.), injected subcutaneously with 2.5 mg of Depo-Provera® (DP; medroxyprogesterone acetate) (Pharmacia & Upjohn Company, Kalamazoo, Mich.) seven days prior to experiments. mCVM was collected by lavage with 20 µL of normal saline, and mCVM from 10-15 mice was pooled to collect sufficient quantities for multiple particle tracking studies. The collection procedure yields highly viscoelastic mucus, as observed visually and through particle tracking experiments. Mucus was stored at 4° C. until used for microscopy within 48 hrs. Mice were anesthetized prior to experimental procedures. All experimental protocols were approved by the University of North Carolina at Chapel Hill Institutional Animal Care and Use Committee.

Nanoparticle Preparation and Characterization:

To produce PEGylated nanoparticles (PS-PEG), we covalently modified 100 nm fluorescent, carboxyl-modified polystyrene beads (PS; Molecular Probes, Eugene, Oreg.) with 2 kDa methoxy poly(ethylene glycol) amine (PEG; Rapp Polymere, Tuebingen, Germany) via a carboxyl-amine reaction, as published previously (Lai et al., *Proc. Natl. Acad. Sci. USA* 104:1482 (2007); Yang et al., *Mol. Pharm.* 11:1250 (2014)). Particle size and ζ-potential were determined by dynamic light scattering and laser Doppler anemometry, respectively, using a Zetasizer Nano ZS (Malvern Instruments, Southborough, Mass.). Size measurements were performed at 25° C. at a scattering angle of 90°. Samples were diluted in 10 mM NaCl solution, and measurements were performed according to instrument instructions. High density PEGylation was verified using the fluorogenic compound 1-pyrenyldiazomethane (PDAM) to quantify residual unmodified carboxyl groups on the polystyrene beads (Yang et al., *Mol. Pharm.* 11:1250 (2014)). PEG conjugation was also confirmed by a near-neutral ζ-potential (Table 1) (Lai et al., *Proc. Natl. Acad. Sci. USA* 104:1482 (2007)).

Antibody Binding to Nanoparticles:

Mouse anti-PEG IgG (3.3) and IgM (AGP-4) antibodies have been previously described (Su et al., *Bioconjug. Chem.* 21:1264 (2010)). Anti-PEG IgG and IgM binding to PS-PEG nanoparticles was confirmed by dot blot assay. Two microliters of PS or PS-PEG beads were blotted onto nitrocellulose membranes. The membranes were incubated with 1:2000 dilutions of anti-PEG IgM, control IgM (anti-vancomycin; Santa Cruz Biotechnology, Dallas, Tex.), anti-PEG IgG, or control IgG (anti-HIV-1 gp120; Santa Cruz Biotechnology, Dallas, Tex.), followed by incubation with a 1:10000 dilution of HRP-labeled goat anti-mouse IgM (Life Technologies, Carlsbad, Calif.) or a 1:7000 dilution of HRP-labeled goat anti-mouse IgG (Santa Cruz Biotechnology, Dallas, Tex.). Bound secondary antibody was detected using an ECL kit (BioRad, Hercules, Calif.), and imaged using a FluorChem E system (ProteinSimple, San Jose, Calif.). The binding avidity for anti-PEG IgG (3.3) has been reported to be $1.3 \times 10^{-7}$ M at room temperature (Su et al., *MAbs* 6:1069 (2014)), while that for anti-PEG IgM (AGP.4) is at least $1.4 \times 10^{-10}$ M (Ehrlich et al., *J. Mol. Recognit.* 22:99 (2009)).

Multiple Particle Tracking:

Dilute particle solutions (~$10^8$-$10^9$ particles/mL, 5% v/v) were added to 20 µL of mCVM in custom-made chambers, and samples were incubated 1 hr at 37° C. before microscopy. The trajectories of the fluorescent particles in mCVM were recorded using an EMCCD camera (Evolve 512; Photometrics, Tucson, Ariz.) mounted on an inverted epifluorescence microscope (AxioObserver D1; Zeiss, Thornwood, N.Y.), equipped with an Alpha Plan-Apo 100×/1.46 NA objective, environmental (temperature and $CO_2$) control chamber and an LED light source (Lumencor Light Engine DAPI/GFP/543/623/690). Videos (512×512, 16-bit image depth) were captured with MetaMorph imaging software (Molecular Devices, Sunnyvale, Calif.) at a temporal resolution of 66.7 ms and spatial resolution of 10 nm (nominal pixel resolution 0.156 µm/pixel). The tracking resolution was determined by tracking the displacements of particles immobilized with a strong adhesive, following a previously described method (Apgar et al., *Biophys. J.* 79:1095 (2000)). Particle trajectories were analyzed using MATLAB software as described previously (Wang et al., *J. Control. Release* 220(Pt A):37 (2015)). Sub-pixel tracking resolution was achieved by determining the precise location of the particle centroid by light-intensity-weighted averaging of neighboring pixels. Trajectories of n≥40 particles per frame on average (corresponding to n≥100 total traces) were analyzed for each experiment, and four independent experiments were performed in mCVM collected from different mice. The coordinates of particle centroids were transformed into time-averaged mean squared displacements (MSD), calculated as $<\Delta r^2(\tau)>=[x(t+\tau)-x(t)]^2+[y(t+\tau)-y(t)]^2$ (where τ=time scale or time lag), from which distributions of MSDs and effective diffusivities ($D_{eff}$) were calculated, as previously demonstrated (Lai et al., *Proc. Natl. Acad. Sci. USA* 104:1482 (2007); Dawson et al., *J Biol. Chem.* 278:50393 (2003); Suh et al., *Adv. Drug Deliv. Rev.* 57:63 (2005)). MSD may also be expressed as MSD=$4D_0\tau^\alpha$, where α, the slope of the curve on a log-log scale, is a measure of the extent of impediment to particle diffusion (α=1 for pure unobstructed Brownian diffusion; α<1 indicates increasing impediment to particle movement as a decreases). Mobile particles were defined as those with $D_{eff} \geq 10^{-1.5}$ µm²/s at τ=0.2667 s (this τ corresponds to a minimum trajectory length of 5 frames), based on multiple datasets of mobile and immobile nanoparticles (e.g., PS and PS-PEG nanoparticles) in human mucus (Lai et al., *Proc. Natl. Acad. Sci. USA* 107:598 (2010); Lai et al., *Proc. Natl. Acad. Sci. USA* 104:1482 (2007)). For particles ~100 nm in size, a $D_{eff} \geq 10^{-1.5}$ µm²/s effectively means that the particles move a distance greater than their diameters within 0.2667 s.

Distribution of Nanoparticles in the Mouse Vagina:

To evaluate PEGylated nanoparticle trapping in vivo, we used female 6-8 week old CF-1 mice (Harlan, Frederick, Md.) pretreated with 100 mg of 17β-estradiol benzoate (Sigma, St. Louis, Mo.) injected subcutaneously two days before the experiments (Ensign et al., *Sci. Transl. Med.* 4:138ra79 (2012)). Anti-PEG or control (anti-vancomycin) IgM was first administered to the mouse vagina in two doses: 10 µL of 150 µg/mL antibody in 0.5× normal saline, and after a 10 min interval, another 10 µL dose in normal saline. The mildly hypotonic medium in the first dose resulted in advective transport of antibody close to the epithelium (Ensign et al., *Biomaterials* 34:6922 (2013)), which, combined with the second dose in isotonic medium, ensured antibody was well distributed throughout the luminal layer. After another 10 min interval, 20 µL of either PS-PEG or control PS (0.025% w/v) was administered in a slightly hypotonic medium (0.75× normal saline). Mice were sacrificed after 10 min, and the entire vagina was then gently removed and frozen in Tissue-Tek® O.C.T.™ Compound (Sakura Finetek U.S.A., Inc., Torrance, Calif.). Transverse sections were obtained at various points along the length of the tissue (between the introitus and the cervix) with a Microm HM 500 M Cryostat (Microm International). The thickness of the sections was set to 6 µm to achieve single-cell layer thickness. The sections were then stained with ProLong Gold antifade reagent (Invitrogen, Grand Island, N.Y.) with 4',6-diamidino-2-phenylindole (DAPI) to visualize cell nuclei and retain particle fluorescence. Fluorescence images of the sections were obtained with an inverted fluorescence microscope at 10× magnification. The same procedures were performed for at least n=4 mice per condition. Mice were anesthetized for the duration of experiments. All experimental protocols were approved by the Johns Hopkins Institutional Animal Care and Use Committee.

Statistical Analysis:

Data averages are presented as means with standard error of the mean (SEM) indicated. Statistical significance was determined by a one-tailed, Student's t-test ($\alpha$=0.05).

Results

Due to both passive transudation and active transport by the MHC class I-related neonatal Fc receptor (Li et al., *Proc. Natl. Acad. Sci. USA* 108:4388 (2011)), IgG, rather than IgA, is the predominant immunoglobulin in human CVM secretions (>10-fold more IgG than IgA) (Usala et al., *J. Reprod. Med.* 34:292 (1989)). However, the routes of PEG exposure that may lead to gradual induction of anti-PEG IgG in humans are not yet known and would be difficult to produce in mice. Therefore, we first tested whether exogenous murine anti-PEG IgG added to ex vivo mouse CVM (mCVM) at concentrations typical of pathogen-specific antibodies in humans (Wang et al., *Mucosal Immunol.* 7:1036 (2014)) could alter the mobility of polystyrene (PS) nanoparticles with PEG grafting at densities well into the dense brush regime (PS-PEG; diameter ~100 nm) (Table 1). Both anti-PEG IgG and IgM (previously shown to bind the PEG backbone) bound specifically to PS-PEG but not uncoated PS nanoparticles (FIGS. 12A-12D), presumably because the degree of curvature on the nanoparticles would cause PEG chains to increasingly assume a more diffuse mushroom conformation that exposes the polymer backbone at distances far from the particle core.

TABLE 1

Characterization of PEG-modified nanoparticles, and ratios of the ensemble average diffusion coefficients in water ($D_w$) compared to in mCVM ($D_m$). Size and ζ-potential values for carboxyl-modified beads are provided for comparison.

| Size (nm)* | Surface Chemistry | Diameter (nm) | ζ-potential (mV) | PEG Density (PEG/nm²)† | $D_w/D_m$‡ |
|---|---|---|---|---|---|
| 100 | COOH | 109 ± 4 | −55 ± 5 | N/A | N/A |
| 100 | PEG | 132 ± 3 | −7 ± 3 | 2.3 ± 0.1 | 4.9 |

*Provided by the manufacturer.
†Calculated from % COOH substitution measured by PDAM assay.
‡Effective diffusivity values are calculated at a time scale of 0.2667 s. $D_w$ is calculated from the Stokes-Einstein equation.

Figure 8A:
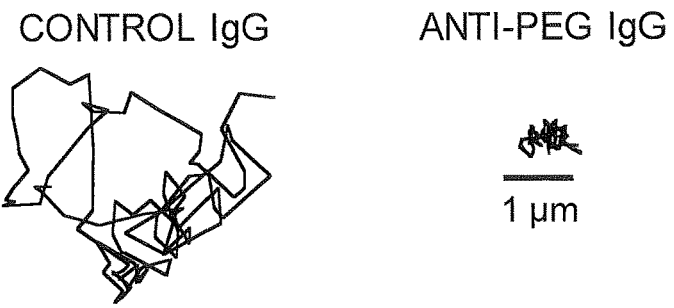
FIGS. 8A-8C show diffusion rates of PEG-coated nanoparticles in mCVM treated with different IgG antibodies. (A) Representative trajectories for particles exhibiting effective diffusivities within one SEM of the ensemble average at a time scale of 0.2667 s. (B) Ensemble-averaged geometric mean square displacements (<MSD>) as a function of time scale. * indicates a statistically significant difference (p<0.05). (C) Distributions of the logarithms of individual particle effective diffusivities ($D_{eff}$) at a time scale of 0.2667 s. Log $D_{eff}$ values to the left of the dashed line correspond to particles with displacements of less than 100 nm (i.e., less than the particle diameter) within 0.2667 s. These small motions are consistent with particles permanently stuck to the mucus gel, and most likely reflect thermal motions of the gel itself. Data represent the ensemble average of four independent experiments, with n≥40 particles per frame (n≥130 particle traces per experiment) on average for each experiment.
Figure 8B:
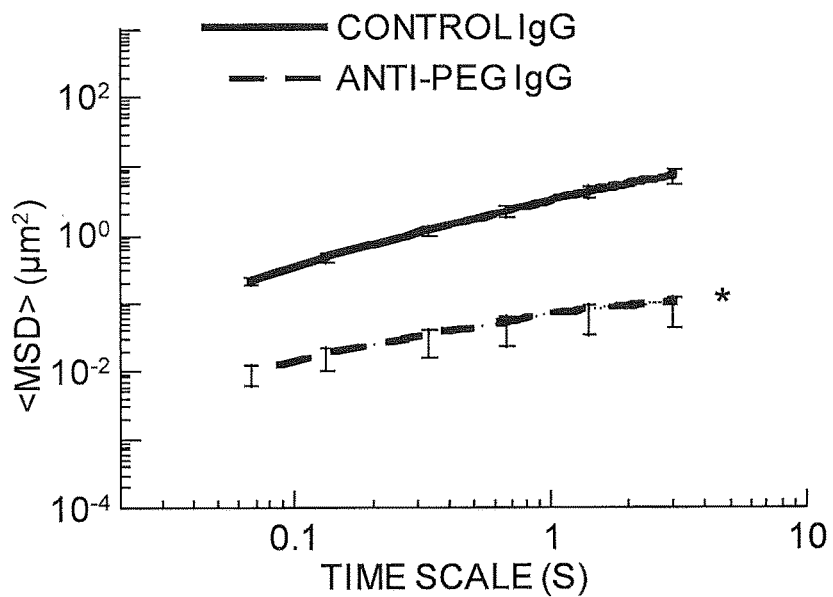
Figure 8C:
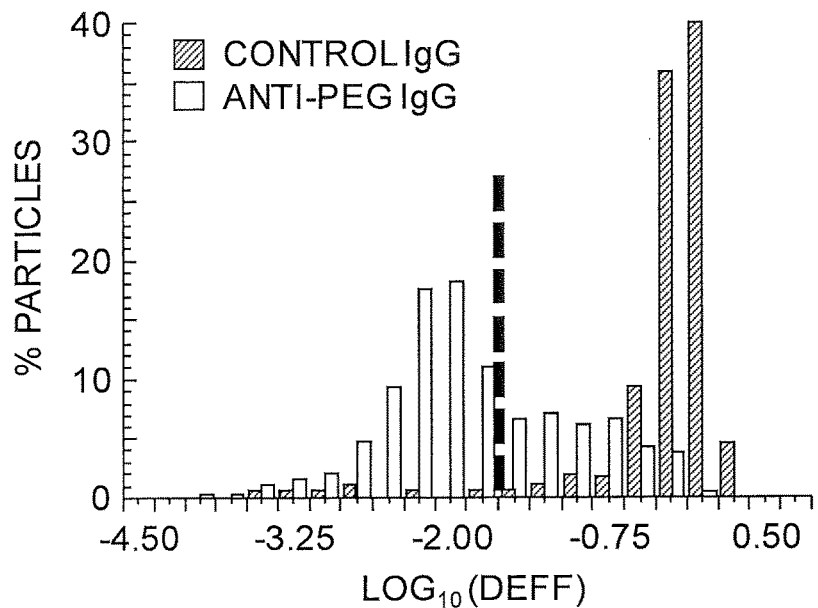

In mCVM without exogenously added anti-PEG IgG or treated with control mouse IgG, PS-PEG exhibited largely unhindered Brownian motion, with particles capable of diffusing many microns on the order of seconds (FIG. 8A). However, in mCVM first treated with anti-PEG IgG to a final concentration of 10 µg/mL prior to the addition of nanoparticles, a large fraction of PS-PEG became immobilized. We quantified the speeds of PS-PEG in mucus treated with different antibodies using multiple particle tracking, a technique that allows quantitative measurements of hundreds of individual particles. PS-PEG particles in control mCVM were only slowed ~5-fold compared to their theoretical speeds in water (Table 1), in good agreement with previous reports (Lai et al., *Proc. Natl. Acad. Sci. USA* 107:598 (2010); Ensign et al., *Mol. Pharm.* 10:2176 (2013)). The addition of anti-PEG IgG reduced the geometrically averaged ensemble mean squared displacement (<MSD>) by ~30-fold compared to control IgG (FIG. 8B; at a time scale of 0.2667 s). The impediment to free Brownian diffusion caused by anti-PEG IgG was also reflected by the slope $\alpha$ from the log-log <MSD> vs. time scale plots ($\alpha$=1 for pure unobstructed Brownian diffusion, e.g., particles in water, and a becomes smaller and approaches zero as obstruction to Brownian diffusion increases): the average a value was 0.86 for PS-PEG in control CVM, but 0.52 for PS-PEG in mCVM treated with anti-PEG IgG (p<0.05 vs. control). Importantly, the mobile PS-PEG fraction (see Methods) was reduced from 96% in control mCVM to only 34% in anti-PEG treated mCVM. These results demonstrate the ability for anti-PEG IgG to alter the mobility of PEGylated nanoparticles in mucus secretions.

Figure 9A:
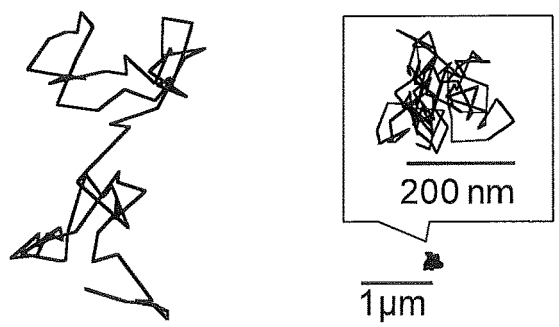
Figure 9B:
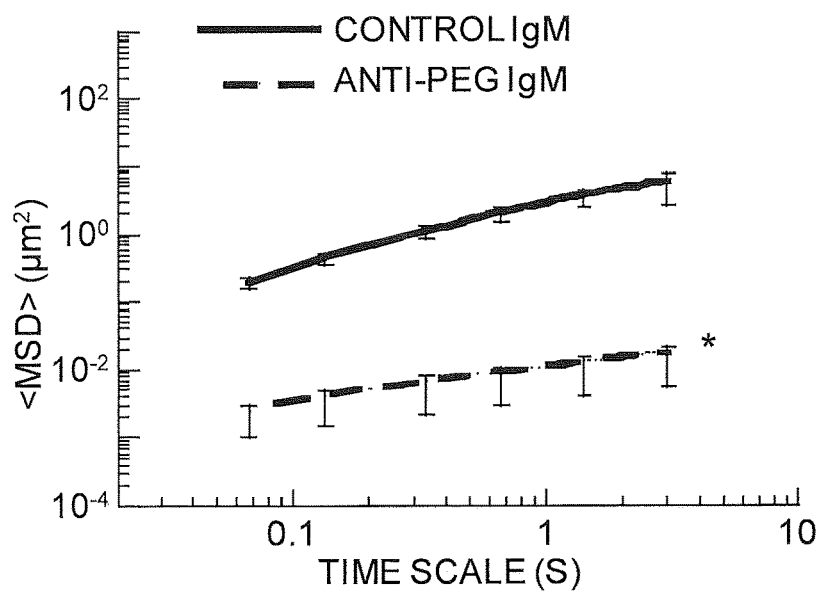
Figure 9C:
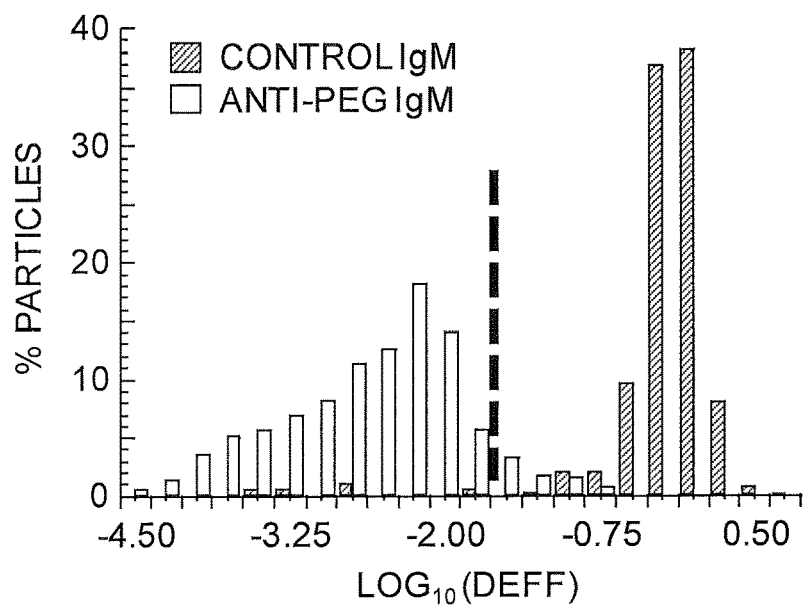
Figure 11:
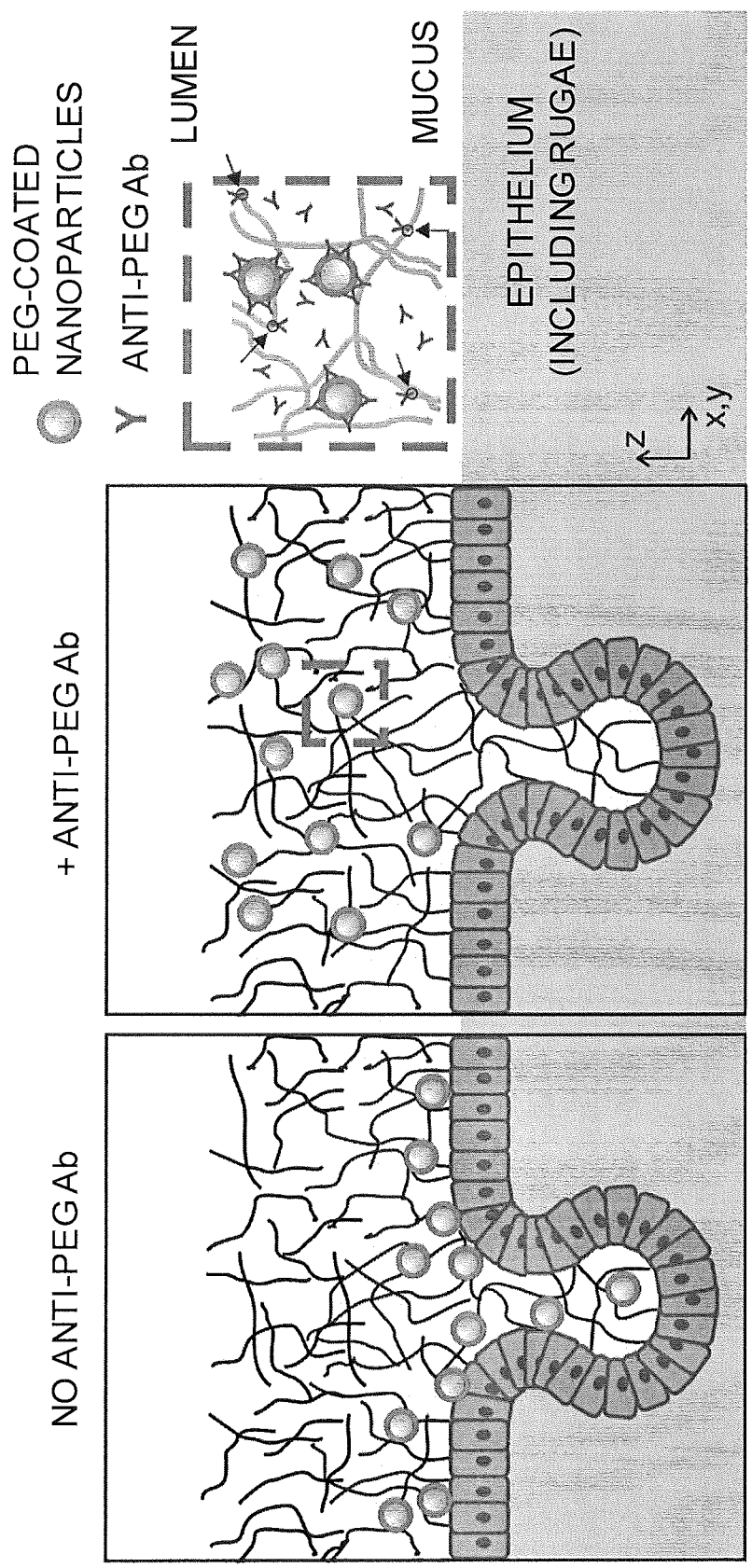
FIG. 11 shows a schematic illustrating the effects of anti-PEG antibodies in mucus on PEG-coated nanoparticles administered to the vaginal mucosal surface. In the absence of specific antibodies, PEG-coated nanoparticles can diffuse quickly through the mucus layer and reach the vaginal epithelium as well as enter into the rugae (folds in the vaginal epithelium), thereby achieving more uniform coverage of the entire epithelial surface. In contrast, when anti-PEG antibodies are present in mucus, PEG-coated nanoparticles become immobilized in mucus, and are largely localized within the mucus layer rather than in close proximity to the vaginal epithelium.

We next sought to test whether an agglutinating antibody may trap PEGylated particles even more extensively. Secretory IgA (sIgA) is another common immunoglobulin found in mucus. The polymeric nature of sIgA, as well as IgM, has long been suggested to facilitate "immune exclusion", the agglutination of microorganisms by polymeric immunoglobulins into clusters too large to diffuse through mucus (Roche et al., *Mucosal Immunol.* 8:176 (2015)). The relevance of sIgA- and IgM-mediated immune exclusion in the female reproductive tract is vividly illustrated by agglutination of otherwise vigorously motile sperm, which make little to no forward progress after agglutination and cannot 'swim' through mucus (Cone, Mucus, in *Handbook of Mucosal Immunology*, P. L. Ogra, et al., Editors. 1999, Academic Press: San Diego. p. 43-64). Unfortunately, anti-PEG sIgA is not commercially available and cannot be readily generated in the lab. Therefore, we evaluated the effects of anti-PEG IgM on the diffusion behavior of PEGylated nanoparticles in mucus. Addition of anti-PEG IgM immobilized an even greater fraction of PS-PEG than did anti-PEG IgG and at a lower antibody concentration (5 µg/mL vs. 10 µg/mL; FIG. 9A). In contrast, addition of control IgM did not alter the diffusion of PS-PEG. The <MSD> of PS-PEG in mCVM with anti-PEG IgM was 150-fold lower than for the same particles in mCVM treated with control IgM (FIG. 9B), and reflects a drop in the mobile fraction from 97% to 7% (FIG. 9C). Anti-PEG IgM also reduced the average a value of PS-PEG from 0.79 to 0.45 (p<0.05 vs. control), underscoring the extent of antibody-mediated immobilization. Interestingly, we did not observe any nanoparticle agglutination in mCVM with anti-PEG IgM; agglutination was only observed when nanoparticles were pre-mixed with anti-PEG IgM prior to addition to mucus (FIGS. 13A-13C).

Lastly, we wanted to evaluate whether the observed changes to the diffusion of PEGylated nanoparticles in physiological mucus specimens ex vivo would also alter nanoparticle distribution at mucosal surfaces in vivo. We therefore topically administered anti-PEG or control IgM to the mouse vagina, followed by addition of PS-PEG in hypotonic medium. We observed that a substantial fraction of PS-PEG was drawn advectively through luminal mucus and accumulate immediately adjacent to the epithelium in mice dosed with control IgM, with a significant fraction penetrating deep into the rugae (FIG. 10A). In contrast, PS-PEG nanoparticles were largely trapped in luminal mucus in mice that received anti-PEG IgM; far fewer particles reached the vaginal epithelium or penetrated into the rugae (FIG. 10B), similar to mucoadhesive carboxylated latex beads (Ensign et al., Sci. Transl. Med. 4:138ra79 (2012)). These results are consistent with previous observations that nanoparticles that interact with and bind to the mucin mesh fibers overlaying the epithelium are unable to penetrate the mucus layer and reach the epithelium (Ensign et al., Sci. Transl. Med. 4:138ra79 (2012)).

The emergence of anti-PEG antibodies represents a potential Achilles' heel to the increasingly common use of PEG in nanomedicine. Rodent studies have clearly and unequivocally illustrated that anti-PEG immunity directly abrogates the extended circulation times that PEGylation generally affords to therapeutics. Anti-PEG immunity may also result in serious complications beyond poor pharmacokinetics. Indeed, anti-PEG response as a result of repeated weekly injections of PEGylated liposomes containing synthetic oligodeoxynucleotides led to significant morbidity and mortality in mice (Semple et al., J. Pharmacol. Exp. Ther. 312: 1020 (2005)). In human clinical studies of PEG-uricase for the treatment of gout, the presence of anti-PEG antibodies was associated with early elimination and poor outcomes (Ganson et al., Arthritis Res. Ther. 8:R12 (2006); Sundy et al., Arthritis Rheum. 56:1021 (2007)). While these studies all highlight the systemic effects associated with anti-PEG response, potential mucosal anti-PEG response has not been evaluated to date. Our finding that anti-PEG IgG or IgM can directly impede the mobility and consequently alter the biodistribution of PEGylated nanoparticles at mucosal surfaces adds yet another pitfall of anti-PEG immunity in vivo (FIG. 11).

More antibodies are secreted into mucus than into blood or lymph; thus, a major part of the physiological immune response is likely intended to occur in the mucus secretions coating exposed surfaces of the respiratory, gastrointestinal and urogenital tracts. However, the notion that secreted antibodies can work together with mucus to impede the mobility of pathogens and foreign particulates and reduce the flux arriving at the epithelium remains largely unrecognized. This is in part a consequence of the exceedingly weak affinity between antibodies and mucus, which would suggest that individual antibodies are incapable of crosslinking a pathogen or particle to mucus. It was not until very recently that virus-binding antibodies were shown to be capable of immobilizing viruses in human mucus secretions (Wang et al., *Mucosal Immunol.* 7:1036 (2014)). Our finding that anti-PEG antibodies can immobilize PEGylated nanoparticles in mCVM offers further evidence that trapping by antibody-mucin crosslinking may be a universal mechanism of mucosal immunity across different animal species.

We found that anti-PEG IgM was substantially more potent in trapping individual PEGylated nanoparticles in mucus than anti-PEG IgG. This may be due to a number of reasons. First, anti-PEG IgM has a higher binding avidity to PEG than anti-PEG IgG (see Methods), which likely translates to greater antibody accumulation on the surface of PEGylated nanoparticles. Second, IgM likely possesses greater affinity to mucins than IgG. This can be inferred from the diffusivity of individual IgM molecules in mucus, which is slowed nearly 50% compared to in buffer, whereas individual IgG molecules are slowed only ~5-20% in mucus compared to in buffer (Olmsted et al., *Biophys. J.* 81:1930 (2001)). Because both IgG and IgM are far too small relative to the mucin mesh spacing (Lai et al., *Proc. Natl. Acad. Sci. USA* 107:598 (2010)) to be slowed substantially by steric hindrance, IgM must be slowed to a greater extent than IgG due to more or stronger adhesive interactions with mucus constituents. The greater mucin-of IgM implies fewer particle-bound IgM would be needed to immobilize a PEGylated nanoparticle compared to IgG; indeed, greater trapping of PS-PEG was achieved with IgM than IgG even at a lower concentration.

Interestingly, we observed negligible levels of agglutination in all of our microscopy studies. This is likely because even a single particle-bound IgM can substantially impede the Brownian motion of the particle (assuming the binding of IgM to PEG does not alter IgM affinity to mucins, a single IgM bound to the nanoparticle may slow it down by ~50%), and lower particle mobility directly reduces the frequency of colliding with other particles, a necessary first-step to agglutination. Thus, IgM-induced agglutination is unlikely to be prevalent when the kinetics of IgM accumulating onto the nanoparticle surface is substantially faster than the rate of collision between nanoparticles. This directly challenges the general dogma that antibody-mediated agglutination—often supported by micrographs showing the formation of large immune complexes upon incubation of antibodies and pathogens in buffer in the absence of mucus—is a dominant mechanism of mucosal immunity by polymeric immunoglobulins.

The vast majority of the literature on anti-PEG immunity focuses on the acute induction of anti-PEG immune response by specific PEGylated liposomes or nanoparticle therapeutics. The possibility of pre-existing anti-PEG response is rarely addressed. Because most of the population has yet to receive PEGylated therapeutics, the presence of PEG-specific antibodies in bodily secretions such as mucus most likely results from induction by alternative routes of exposure. Since PEG and other PEG-containing polymers are often found in soaps and other detergents, a hypothetical route of exposure could be via open cuts and wounds cleaned with PEG-containing soaps, or bleeding gums at the oral mucosa exposed to PEG-containing toothpaste. The combination of PEG and soap surfactants that are toxic to cells may provide a danger signal that inadvertently induces immune cells to generate antibodies against PEG. Alternatively, PEG is also frequently found in numerous foods as well as oral and topical products. Repeated exposure to PEG at the oral, gastrointestinal and vaginal mucosa, including exposure accompanied by surfactants, could potentially induce systemic and/or mucosal anti-PEG immunity over time, with significant implications for the delivery of PEGylated therapeutics via relevant routes of administration.

PEG is widely used in nanomedicine as a stealth coating polymer to improve circulation time and therapeutic efficacy. However, a growing body of evidence generated over the past two decades shows that systemic exposure to PEG can induce anti-PEG antibodies that not only significantly alter the systemic circulation kinetics of PEG-modified nanotherapeutics, but may also directly result in adverse outcomes. Our finding that anti-PEG antibodies can also trap PEG-coated nanoparticles in mucus secretions ex vivo and alter particle biodistribution at mucosal surfaces in vivo further suggests that mucosal anti-PEG immunity may be an under-recognized challenge. Mucosal exposure to PEG and the prevalence of anti-PEG antibodies in human mucus is not yet well understood. In light of the large arsenal of PEGylated therapeutics that are FDA-approved or in clinical development for both systemic and mucosal applications, we believe further investigations into the origin and characteristics of pre-existing anti-PEG immunity are of critical importance to support ongoing efforts in translational nanomedicine development.

EXAMPLE 3

A Blueprint for Robust Crosslinking of Mobile Species in Biogels Using Third Party Crosslinking Anchors with Short-Lived Anchor-Matrix Bonds Biopolymeric matrices are ubiquitous in living systems, generically composed of a highly entangled and cross-linked mesh of macromolecules in buffer. Within cells, cytoskeletal networks of actin and microtubules control cell migration, maintain cell shape and polarity, and facilitate proper routing and sorting of intracellular cargo (Huber et al., *Adv. Phys.* 62:1 (2013)). At the extracellular scale, networks of fibronectin and collagen not only provide scaffolds for mechanical support and tissue organization, but also regulate the dynamic behavior of cells through variations in local microstructure and stiffness (Theocharis et al., *Adv. Drug Deliv. Rev.* 97:4 (2016)). At the tissue scale, secreted mucins create a viscoelastic gel that serves both as a lubricant and as a transport barrier to prevent pathogens and particulates from reaching the underlying epithelium (Lai et al., *Adv. Drug Deliv. Rev.* 61:86 (2009)).

A major function of biogels is to regulate transport. Gels can impede the passive diffusion of particulates and active motion of bacteria and cells by steric obstruction from as well as adhesive interactions to the matrix constituents. Given that the majority of nanoparticles and viruses are smaller than the mesh spacings, their diffusion across a gel can only be hindered by adhesive interactions. However, due to evolutionary pressure, it is exceedingly unlikely that direct adhesive interactions with matrices comprised of relatively homogeneous constituents, such as mucins or laminins, can alone effectively block the transport of the full diversity of nanoparticulates typically encountered in nature. For example, viruses must penetrate the dense mucin mesh to infect underlying cells; thus, it is hardly surprising that the vast majority of viruses that transmit at mucosal surfaces (HIV, Herpes, HPV, Norwalk, etc.) are able to evade binding to mucins and diffuse rapidly through the low viscosity interstitial fluids within pores of mucus gels (Olmsted et al., *Biophys. J.* 81:1930 (2001)).

An alternative strategy is to utilize "third party" molecular anchors to crosslink nano-scale species (henceforth referred to as nanoparticles) to the matrix, such as antibodies (Ab) that can specifically recognize and bind invading pathogens. The diffusion coefficients of IgG and IgA Ab in human mucus are ~5-10% lower compared to buffer, whereas 10-fold larger viruses can diffuse in mucus unhindered. The slightly retarded diffusion of both Ab implies they must be slowed by weak and transient interactions with the mucus matrix. Surprisingly, despite this seemingly negligible affinity, herpes-binding IgG can specifically and effectively immobilize Herpes Simplex Viruses (HSV-1) in human cervicovaginal mucus even at sub-neutralizing IgG concentrations, and trapping HSV-1 in mucus directly prevented vaginal herpes transmission in mice (Wang et al., IgG in cervicovaginal mucus traps HSV and prevents vaginal Herpes infections. *Mucosal Immunol.* 7:1 (2014)). It remains unclear whether the trapping potency of IgG can be further enhanced by tuning its affinity with matrix constituents. To potentially develop more potent anchors, we sought to examine the characteristics of IgG that could maximize net adhesive interactions between nanoparticles and biopolymer matrices. The widely held and intuitively reasonable assumption is that anchors with long-lived, high-affinity bonds to both the nanoparticle and matrix would confer superior trapping efficiency. Surprisingly, we herein show theoretically and experimentally that anchor-matrix bonds that are rapid and short-lived relative to anchor-nanoparticle bonds greatly enhances trapping potency of molecular anchors.

Methods

Preparation of PEG-Coated Nanoparticles:

To produce PEGylated nanoparticles (PS-PEG), we covalently modified 200 nm fluorescent, carboxyl-modified polystyrene beads (PS-COOH; Invitrogen) with 2 kDa methoxy poly(ethylene glycol) amine (PEG; Sigma) via a carboxyl-amine reaction, as published previously (Lai et al., *Proc. Natl. Acad. Sci. USA* 104:1482 (2007); Yang et al., *Mol. Pharm.* 11:1250 (2014)). Particle size and $\zeta$-potential were determined by dynamic light scattering and laser Doppler anemometry, respectively, using a Zetasizer Nano ZS (Malvern Instruments, Southborough, Mass.). Size measurements were performed at 25° C. at a scattering angle of 90°. Samples were diluted in 10 mM NaCl solution, and measurements were performed according to instrument instructions. High density PEGylation (>1 PEG/nm$^2$) was verified using the fluorogenic compound 1-pyrenyldiazomethane (PDAM) to quantify residual unmodified carboxyl groups on the polystyrene beads (Yang et al., *Mol. Pharm.* 11:1250 (2014)). PEG conjugation was also confirmed by a near-neutral $\zeta$-potential (Lai et al., *Proc. Natl. Acad. Sci. USA* 104:1482 (2007)).

Preparation of BM, Laminin/Entactin, and Collagen Gels:

Growth-factor reduced Matrigel (Corning) was dialyzed against PBS for a minimum of 24 hours, then biotinylated with 20-fold molar concentration NHS-PEG4-biotin (ThermoFisher). This biotinylated Matrigel (final concentration 2.2 mg/mL) was mixed with neutravidin (ThermoFisher; final concentration 0 or 4 µg/mL), BSA (Sigma, final concentration 1 mg/mL), Eagle's Minimum Essential Medium (EMEM, Lonza BioWhittacker), on ice for 15 minutes. Fluorescent PS-COOH (Ex: 505 nm, Em515 nm; final concentration 4.5*10$^8$ beads/mL) and PS-PEG (Ex: 625 nm, Em645 nm; final concentration 0.3*10$^8$ beads/mL) nanoparticles and anti-PEG IgG$_1$ (CH2076 or CH2076B, Silver Lake Research, final concentration 10 µg/mL) was combined on ice. The mixture was added to a custom-made micro-volume glass chamber slide, incubated at 37° C. for 45 minutes in a custom hydration chamber, then sealed and incubated for another 30 minutes prior to microscopy. Trapping of PS-COOH beads in BM was used as an internal control in all microscopy experiments as a measure of complete polymerization of BM constituents.

High Resolution Multiple Particle Tracking:

The trajectories of the fluorescent particles were recorded using an EMCCD camera (Evolve 512; Photometrics, Tucson, Ariz.) mounted on an inverted epifluorescence microscope (AxioObserver D1; Zeiss, Thornwood, N.Y.), equipped with an Alpha Plan-Apo 100×/1.46 NA objective, environmental (temperature and $CO_2$) control chamber and an LED light source (Lumencor Light Engine DAPI/GFP/543/623/690). 20 s videos (512×512, 16-bit image depth) were captured with MetaMorph imaging software (Molecular Devices, Sunnyvale, Calif.) at a temporal resolution of 66.7 ms and spatial resolution of 10 nm (nominal pixel resolution 0.156 µm/pixel). The tracking resolution was determined by tracking the displacements of particles immobilized with a strong adhesive, following a previously described method (Apgar et al., *Biophys. J.* 79:1095 (2000)).

Particle trajectories were analyzed using MATLAB software as described previously (Wang et al., *J. Control. Release* 220:37 (2015)). Sub-pixel tracking resolution was achieved by determining the precise location of the particle centroid by light-intensity-weighted averaging of neighboring pixels. Trajectories of n≥40 particles per frame on average (corresponding to n≥100 total traces per specimen/condition) were analyzed for each experiment, and 3-4 independent experiments were performed for each condition. The coordinates of particle centroids were transformed into time-averaged mean squared displacements (MSD), calculated as $\langle\Delta r^2(\tau)\rangle = [x(t+\tau)-x(t)]^2 + [y(t+\tau)-y(t)]^2$ (where $\tau$=time scale or time lag), from which distributions of MSDs and effective diffusivities ($D_{eff}$) were calculated, as previously demonstrated (Lai et al., *Proc. Natl. Acad. Sci. USA* 104:1482 (2007); Dawson et al., *J. Biol. Chem.* 278:50393 (2003); Suh et al., *Adv. Drug Deliv. Rev.* 57:63 (2005)). MSD may also be expressed as MSD=$4D_0\tau^\alpha$, where $\alpha$, the slope of the curve on a log-log scale, is a measure of the extent of impediment to particle diffusion ($\alpha$=1 for pure unobstructed Brownian diffusion; $\alpha$<1 indicates sub-diffusive motion due to interactions with the elastic as well as viscous properties of the polymeric gel). Mobile particles were defined as those with $D_{eff} \geq 10^{-1.5}$ μm²/s at $\tau$=0.2667 s (this $\tau$ corresponds to a minimum trajectory length of 5 frames), based on multiple datasets of mobile and immobile nanoparticles (e.g., PS and PS-PEG nanoparticles) in human mucus Lai et al., *Proc. Natl. Acad. Sci. USA* 104:1482 (2007); Lai et al., *Proc. Natl. Acad. Sci. USA* 107:598 (2010)).

Biolayer Interferometry Experiments:

On an Octet QK instrument (ForteBio), streptavidin biosensors (ForteBio) were loaded with biotinylated Matrigel and blocked with free biotin. Antibody (biotinylated and native) at different concentrations was associated with these customized biosensors and dissociated into running buffer. Data were adjusted for reference sensors and baseline values and aligned to dissociation, then processed with Savitzky-Golay filtering. Analysis was performed with ForteBio software using a 1:1 global curve fit model to obtain values for $k_{on}$, $k_{off}$, and $K_D$.

Mathematical Model:

Instead of developing a reaction-diffusion model for a concentration of nanoparticle species P, we take a stochastic approach and focus on the motion of a single nanoparticle P. The main goal is to maximize the fraction of time that P spends bound to the polymer network.

Let N be the total number of anchor binding sites on the nanoparticle P. The crosslink enhancement effect requires the cooperative action of multiple anchors; it requires N>1 anchor binding sites (e.g., antigenic epitopes) on the nanoparticle. The reactions [eq:1] and [eq:2] describe the case of a single binding site (i.e., N=1). The first crosslink bond forms at a diffusion limited reaction rate according to [eq:2]. If N>1, additional anchors might be bound to the nanoparticle. Once the first crosslink forms many additional binding sites M are very close by, allowing additional anchor-matrix bonds to form. The intra-complex reaction is given by

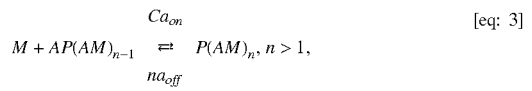

$$M + AP(AM)_{n-1} \underset{na_{off}}{\overset{Ca_{on}}{\rightleftharpoons}} P(AM)_n, n > 1, \quad [\text{eq: 3}]$$

where C is a nondimensional parameter that scales the intra-complex binding rate and assumed to be 1 in the current work. Molecules within a large complex may not react with each other at the same rate as they do when they are freely diffusing. When nanoparticles, anchors, and matrix elements are bound within the same complex, they are mechanically linked. Mechanical forces imposed by surrounding elements of the complex confine random molecular motion. Similar biomechanical reactions are common in biology (e.g., molecular motor transport (Goychuk et al., *PLoS One* 9:1 (2014)) and DNA transcription (Matsuda et al., *Biophys. J.* 106:1801 (2014))). For our present situation, it is a reasonable first approximation to assume that the intra-complex dissociation rates remain the same as the bimolecular dissociation rates (i.e., $a_{off}$ and $k_{off}$). However, intra-complex binding rates are different from the Smoluchowski bimolecular reaction rates for diffusing molecules. The binding rate between two molecules within the complex depends on their relative distance and effective random mobility. Molecules within a single nanocomplex are quite close so that they do not have to move far in order to bind. On the other hand, they have lower relative mobility when mechanically confined within the complex.

Let n be the number of occupied binding sites, and let s be the number of anchors crosslinking the nanoparticle to the polymer network. The chemical system can be modeled as a Markov process with state transitions given by

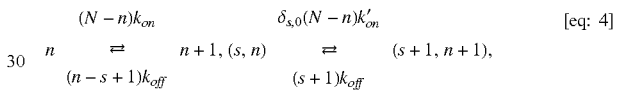

$$n \underset{(n-s+1)k_{off}}{\overset{(N-n)k_{on}}{\rightleftharpoons}} n+1, (s,n) \underset{(s+1)k_{off}}{\overset{\delta_{s,0}(N-n)k'_{on}}{\rightleftharpoons}} (s+1, n+1), \quad [\text{eq: 4}]$$

$$s \underset{(s+1)a_{off}}{\overset{g(s)(n-s)a_{on}}{\rightleftharpoons}} s+1, \quad [\text{eq: 5}]$$

where $$g(s) = \begin{cases} D_P/D_A, & s=0 \\ C, & s \geq 1 \end{cases}.$$

The process is described by its probability density p(n, s, x, t). The probability that at time t, the nanoparticle is bound to n anchors, s of which are bound to elements of the polymer matrix, and located within a small distance dx of position x is $$\text{Prob}[n(t)=n, s(t)=s, x<x(t)<x+dx] = p(n,s,x,t)dx + o(dx).$$

Since the model is a continuous time Markov process, the probability density function satisfies the differential Chapman-Kolmogorov equation, $$\frac{\partial}{\partial t} p(n, s, x, t) = \delta_{s,0} D_P \nabla^2 p + [\mathbb{M}_s + \mathbb{V}_{n,s}]p, \quad [\text{eq: 6}]$$

where $\mathbb{M}_s$ is the N×N transition rate matrix for [eq:5] and $\mathbb{V}_{n,s}$ is the N×N transition rate matrix for [eq:4].

Multiple Timescale Analysis:

Consider the case where $\tau_M \ll \tau_P$. Notice that the fast reaction [eq:5] conserves n. While n changes slowly, transitions in s are at quasi-steady-state. Since we are primarily concerned with the motion of the nanoparticle, and not necessarily the state of any bound anchors, our goal is to obtain a good approximation to the marginal probability $$u(x, t) = \sum_{n=0}^{N} \sum_{s=0}^{N} p(n, s, x, t).$$

Using the rule of conditional probability, we can rewrite the full probability density for the process as $$p(n,s,x,t) = \rho_t(s,t|n,x)\rho_t(n,t|x)u(x,t).$$

Since s changes rapidly compared to n, which changes rapidly compared to x, the conditional probabilities $\rho_t$ rapidly equilibrate, which means that $\rho_t \approx \rho_\infty = \rho$. Since the transition rates are independent of position x, it follows that $\rho(s|n,x) = \rho(s|n)$ and $\rho(n|x) = \rho(n)$. The two probability distributions $\rho(s|n)$ and $\rho(n)$ are called quasi steady state distributions, and they satisfy $$\sum_{s=0}^{N} \mathbb{M}_s \, \rho(s|n) = 0, \qquad [\text{eq: 7}]$$

$$\sum_{s=0}^{N} \sum_{n=0}^{N} \mathbb{V}_{n,s} \, \rho(s|n)\rho(n) = 0.$$

We can take advantage of the separation of time scales with an asymptotic approximation, namely $$p(n,s,x,t) \sim p(s|N)\rho(n)u(x,t). \qquad [\text{eq:8}]$$

First we average out the fastest reaction, the transition in s. Let $\bar{p}(n, x, t) = \rho(n)u(x,t)$. Substituting [eq:8] into [eq:6], summing over s, and using [eq:7] yields $$\frac{\partial}{\partial t}\bar{p}(n, x, t) = D_P \rho(0|n)\nabla^2 \bar{p} + \overline{\mathbb{V}}_n \bar{p}, \qquad [\text{eq: 9}]$$

where $\overline{\mathbb{V}}_n$ is the transition rate matrix for the averaged slow reaction:

$$n \underset{(n+1)k_{off}}{\overset{(N-n)\kappa(n)}{\rightleftarrows}} n+1,$$

where $\kappa(n) = \rho(0|n)k_{on} + k_{on}'$. Given n, the stationary distribution for the number of anchors $s \leq n$ on the nanoparticle that are bound to the matrix is $$\rho(s|n) = \begin{cases} \dfrac{D_A C \alpha^n}{(D_A C - D_P)\alpha^n + D_P}, & s = 0 \\[2mm] \dfrac{D_P \binom{n}{s}(1-\alpha)^s \alpha^{n-s}}{(D_A C - D_P)\alpha^n + D_P}, & s > 0, \end{cases}$$

where $\alpha = a_{off}/(Ca_{on} + a_{off})$.

We can apply the same procedure to average out n as follows. The quasi-steady-state distribution for n is given by $$\rho(n) = \frac{\mathcal{N}}{k_{off}^n}\binom{N}{n}\prod_{j=0}^{n-1}(\rho(0|j)k_{on} + k_{on}'),$$

where $\mathcal{N}$ is a normalization factor. Substituting $\bar{p}(n, x, t) = \rho(n)u(x,t)$ into [eq:9], summing over n, and using [eq:7] yields $$\frac{\partial}{\partial t}u(x, t) = D_{eff}\nabla^2 u, \; D_{eff} = D_P \sum_{n=0}^{N} \rho(0|n)\rho(n). \qquad [\text{eq: 10}]$$

Monte-Carlo Simulations:

To determine the accuracy of the above approximation, we use Monte-Carlo simulations. Using the Gillespie algorithm, we simulate the Markov chain [eq:4] and [eq:5], (which is independent of x). A single realization is generated through m state transitions. The total elapsed time $t_m$ and the total time spend with s=0 (the free diffusing state) $t_m^{(0)}$ are updated with each transition. It is easy to show that $$P[s = 0] = \lim_{m \to \infty} \frac{t_m^{(0)}}{t_m}.$$

Because all increments from free diffusion are independent, an estimator for the effective diffusivity is $$D_m^{eff} \equiv D_P \frac{t_m^{(0)}}{t_m}.$$

Saturated Regime:

The reaction rate for any individual free anchor is substantially reduced by the saturation of matrix binding sites. Because $[A_T] \gg [M]$, the fraction of unoccupied matrix binding sites is equivalent to the fraction of time an individual matrix binding site is unoccupied. Hence, $$\xi = \frac{a_{off}}{\frac{[A_T]}{[M]}a_{on} + a_{off}} \approx \frac{a_{off}[M]}{a_{on}[A_T]}.$$

It follows that the binding rate for an individual freely-diffusing anchor is $$a_{on}' = \xi a_{on} \approx \frac{a_{off}[M]}{[A_T]}. \qquad [\text{eq: 11}]$$

Similarly, the intra-complex binding rate (see Eqn. [eq:3]) is $a''_{on} = Ca_{off}[M]/[A_T]$. Based on the modified binding rate [eq:11], the anchor-matrix kinetic timescale becomes $$\tau_{AM} = \frac{1}{\left(1 + \frac{[M]}{[A_T]}\right)a_{off}} \approx 1/a_{off}.$$

The effective diffusivity in the saturated regime is obtained by substituting $$[A] = [A_*], \, \varphi \approx 1 - \frac{[M]}{[A_T]}, \text{ and } \alpha \approx 1 - C\frac{[M]}{[A_T]} \text{ into [eq: 10]}$$

Results and Discussion

Anchor-Mediated Trapping of Nanoparticles is Far More Efficient with Rapid, Short-Lived Anchor-Matrix Bonds:

The highly viscoelastic nature of physiological mucus gels makes it exceedingly difficult to chemically modify and subsequently remove crosslinkers without irreversibly perturbing its rheological properties. Instead, we took advantage of the thermo-gelling properties of Matrigel®, which enables us to biotinylate the matrix as a low viscosity fluid at 4° C. yet study its diffusional barrier properties as a viscoelastic gel at 37° C. Similar to with mucins, IgG possess exceedingly weak affinity with Matrigel®, as reflected by the high recovery rate of IgG from Matrigel® by simple centrifugation. This allowed us to investigate, using anti-PEG IgG as molecular anchors, whether the mobility of polyethylene glycol-modified polystyrene nanoparticles (PS-PEG; diameter ~200 nm) that exhibits rapid diffusion in the biotinylated Matrigel® can be altered by tuning the affinity of anchor-matrix bonds.

Figure 14C:
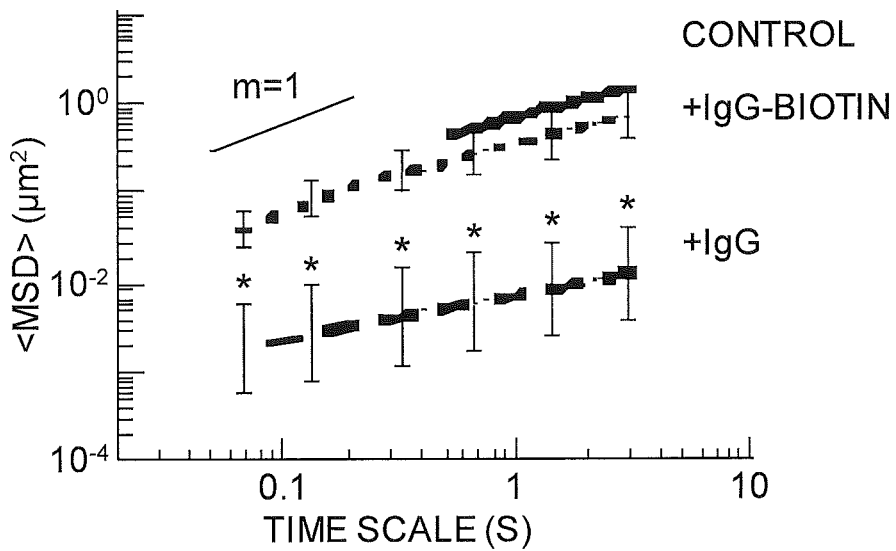
Figure 14D:
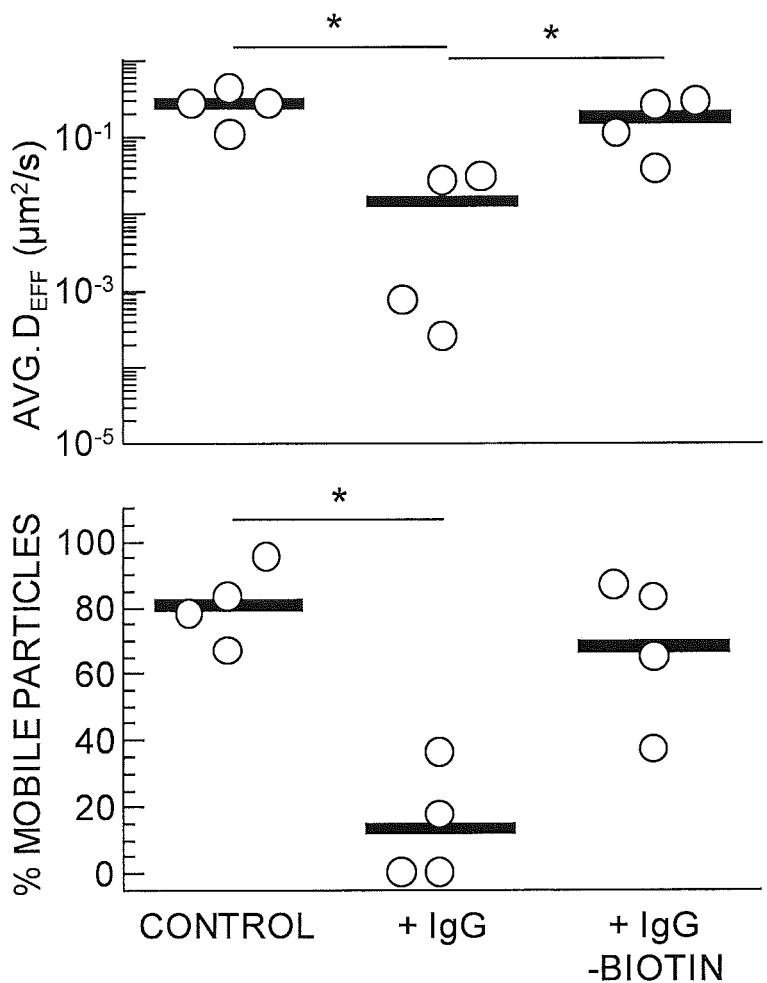
Figure 15A:
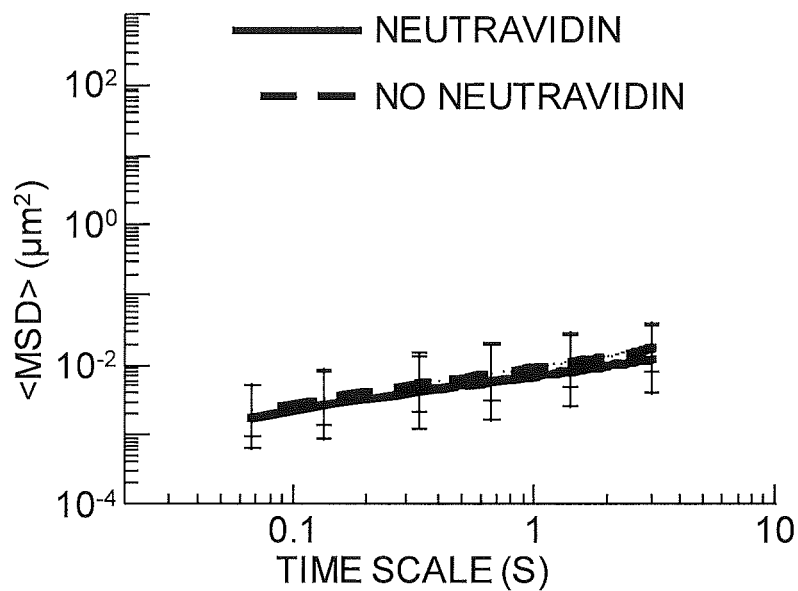
FIGS. 15A-15B show diffusion of PEG-modified nanoparticles in biotinylated basement membrane with anti-PEG IgG, with or without neutravidin. (A) Ensemble-averaged geometric mean square displacements (<MSD>) as a function of time scale. (B) Distributions of the logarithms of individual particle effective diffusivities ($D_{eff}$) at a time scale of 0.2667 s. Log $D_{eff}$ values to the left of the dashed line correspond to particles with displacements of less than 100 nm (i.e., roughly the particle diameter) within 0.2667 s. Data represent the ensemble average of 4 independent experiments per condition, with n≥77 particles per frame on average (n≥92 particle traces per experiment) for each experiment. Error bars represent standard error of the mean (SEM).
Figure 15B:
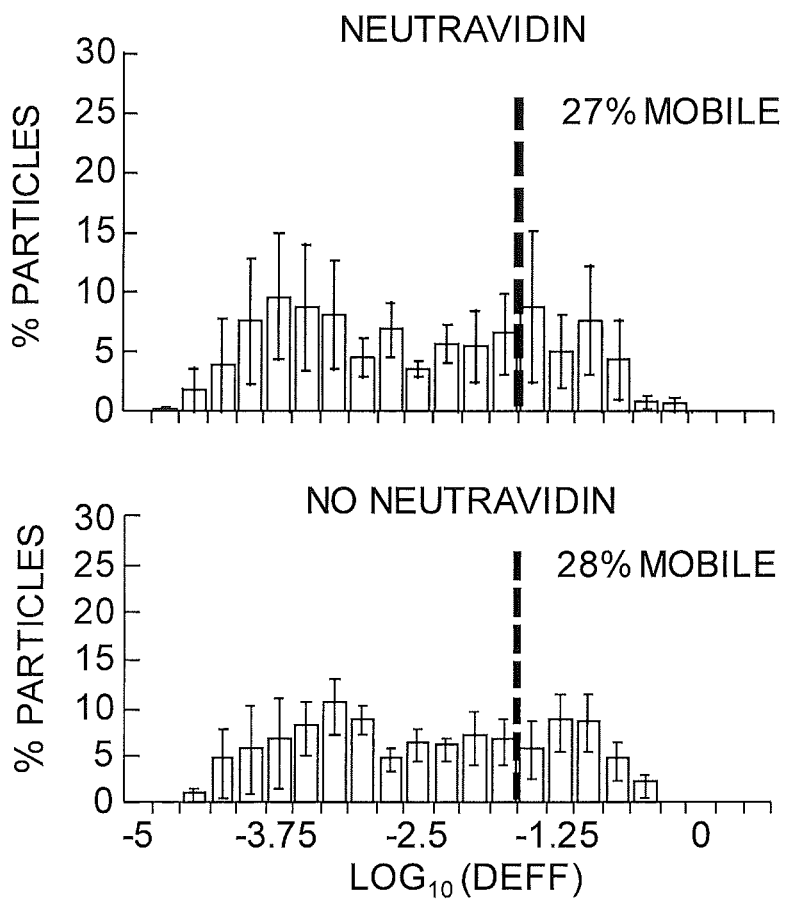
Figure 17A:
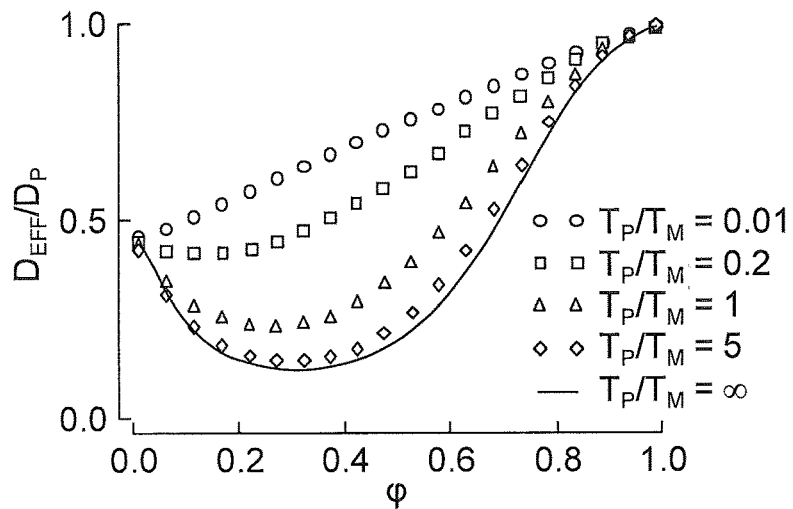
FIGS. 17A-17C show model prediction of the effect of the timescale separation, $\tau_{AP}/\tau_{AM}$, on trapping. Symbols show averages from $10^5$ Monte Carlo simulations. Solid lines show the $\tau_P/\tau_M \to \infty$ approximation. (A) The effective diffusivity obtains a minimum for $0<\varphi<1$ when $\tau_P/\tau_M$ increases above 0.01. (B) Using the effective diffusivity shown in (A), the probability of penetration across a layer of thickness L=50 µm within two hours. (C) A heat map of the effective diffusivity vs. the anchor concentration (for 170 KD anchors) and timescale separation. Parameter values used were $D_A/D_P$=20, N=15.
Figure 17B:
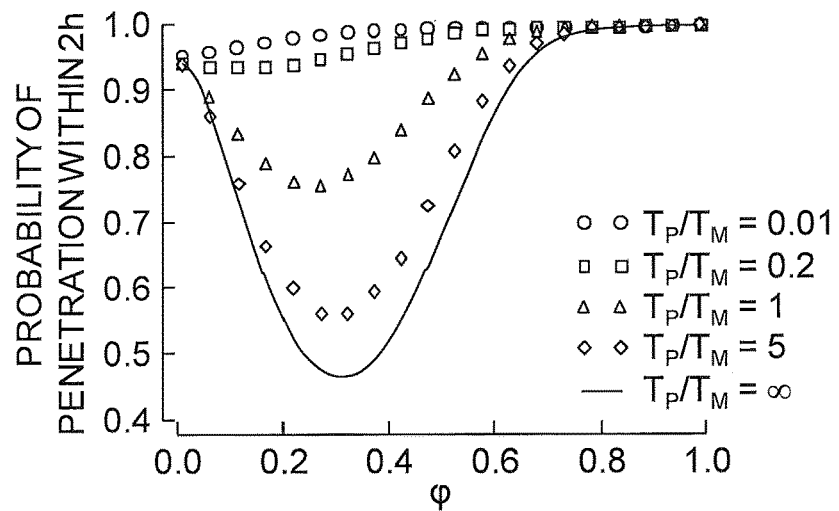
Figure 17C:
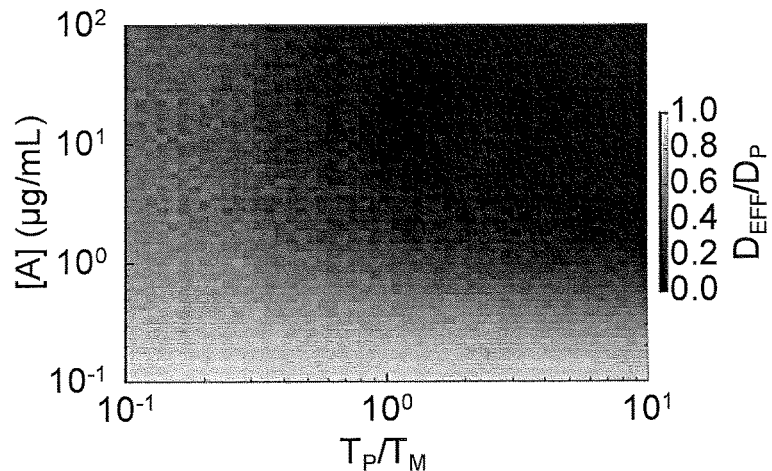

We mixed neutravidin and biotinylated IgG that specifically bind PEG into biotinylated Matrigel® to create high affinity IgG-matrix bonds prior to temperature-induced gelation of the matrix; we verified that both molecules were able to bind with high affinity to biotinylated Matrigel® using biolayer interferometry. In biotinylated Matrigel® mixed with neutravidin, either lacking exogenous IgG altogether or treated with control IgG, PS-PEG exhibited rapid diffusion, with a geometrically averaged ensemble effective diffusivity ($<D_{\it eff}>$; 0.27 μm$^2$/s) only ~8.7-fold reduced compared to their theoretical diffusivity in buffer (FIGS. 14A-14B). The conjugation of biotinylated IgG to Matrigel® did not reduce gel formation or the barrier properties of Matrigel® against ~200 nm uncoated carboxyl-modified nanoparticles, which were immobilized to a similar extent as unmodified Matrigel® (FIGS. 15A-15B). Surprisingly, despite anchoring 10 μg/mL anti-PEG IgG to Matrigel® with long-lived, high affinity biotin-neutravidin bonds, the matrix largely failed to immobilize PS-PEG. Indeed, the $<D_{\it eff}>$ (0.14 μm$^2$/s) of PS-PEG at $\tau$=0.2667 s was not statistically significantly different than in the same Matrigel without anti-PEG IgG, and over 80% of particles remained mobile (defined as nanoparticles with $<D_{\it eff}>\geq 10^{-1}$ μm$^2$/s at $\tau$=0.2667 s; FIGS. 14A-14C). Modest trapping of PS-PEG by matrix-bound anti-PEG IgG was observed only with prolonged incubation, e.g., 24 hrs (FIGS. 16A-16B).

In contrast, despite the seemingly negligible affinity between native unmodified IgG and biotinylated Matrigel®, the addition of 10 μg/mL of anti-PEG IgG in biotinylated Matrigel® reduced the $<D_{\it eff}>$ of PS-PEG by nearly 40-fold, with nanoparticles slowed on average almost 600-fold compared to their mobility in water. The fraction of mobile PS-PEG was reduced from 81% to 14% with the addition of anti-PEG IgG. The immobilization was not due to agglutination of PS-PEG, since trapped nanoparticles appeared identical to non-agglutinated nanoparticles in Matrigel® treated with control IgG. PS-PEG were also unlikely to be immobilized due to marked increase in the nanoparticle hydrodynamic diameter; a complete coating of IgG on ~200 nm nanoparticles would add no more than ~10 nm to the hydrodynamic diameter, and larger nanoparticles remained largely diffusive in Matrigel®. These results directly demonstrate that short-lived anchor-matrix bonds is far more efficient in facilitating immobilization of nanoparticles than long-lived anchor-matrix bonds.

Proposed Theoretical Framework and Assumptions:

Our observations motivated us to develop a model to recapitulate the observations and examine the features of molecular anchors and matrix that could maximize trapping potency of nanoparticles by the matrix. The model assumes three reactive species: molecular anchors A, nanoparticles P, and matrix constituents M. Assuming that anchors must simultaneously possess some affinity to both the matrix and the nanoparticle, our model reveals that the most robust crosslinking of nanoparticles to the matrix, as reflected by a minimum particle diffusivity $D_{\it eff}$, is achieved when the following six conditions are met:

1. Markedly faster anchor-matrix binding-unbinding kinetics than anchor-nanoparticle kinetics. In other words, lifetime of anchor-matrix bonds ($\tau_{AM}$) is short relative to the lifetime of anchor-particle bonds ($\tau_{AP}$) i.e. $\tau_{AM}<<\tau_{AP}$
2. Nanoparticles possess multiple, i.e., N>1 independent binding sites such that multiple anchors can simultaneously crosslink the same nanoparticle to the matrix
3. Anchors are much smaller than the nanoparticle, and consequently, the anchor diffusivity $D_A$ is much larger than the free nanoparticle diffusivity $D_P$; i.e., $D_A>>D_P$
4. The anchor-nanoparticle binding is fast enough that many anchors are likely to bind to the nanoparticle before it diffuses out of the polymer matrix of thickness L; i.e., $\tau_{AP}<\tau_L$
5. $\tau_{AM}$ is sufficiently short such that anchors do not saturate the binding sites in the matrix
6. Anchor concentration [A] is modest, such that on average a single nanoparticle will not be simultaneously bound by two anchors that are immobilized to the matrix. In other words, average [A] does not exceed one anchor per volume of the nanoparticle (i.e. [A]<<1/V$_P$).

In general, with the proposed components M, A and P, there are two reaction sequences that form the desired complex (MAP), corresponding to a trapped nanoparticle. In particular, the MAP complex is formed either by a matrix-bound anchor capturing a free nanoparticle:

$$M + A \underset{a_{\it off}}{\overset{a_{\it on}}{\rightleftarrows}} MA, MA + P \underset{k_{\it off}}{\overset{k'_{\it on}}{\rightleftarrows}} MAP, \quad [\text{eq: 1}]$$

or by a nanoparticle-anchor complex (formed when free anchors accumulate on a diffusing nanoparticle) interacting with and binding to the matrix:

$$A + P \underset{k_{\it off}}{\overset{k_{\it on}}{\rightleftarrows}} AP, M + AP \underset{a_{\it off}}{\overset{\frac{D_P}{D_A}a_{\it on}}{\rightleftarrows}} MAP, \quad [\text{eq: 2}]$$

The anchor-nanoparticle binding rates for free anchors ($k_{on}$) and matrix-bound anchors ($k_{on}'$) are given by the Smoluchowski encounter relation, namely $$k_{on}=(D_P+D_A)\varphi[A]R_0, k_{on}'=(D_P+D_M)(1-\varphi)[A]R_0,$$

respectively, where $R_0$ is the effective binding distance at which two molecules react. Note that the diffusivity of the polymer matrix is effectively zero, i.e., $D_M \approx 0$. The fraction of free A at steady state is related to the binding ($a_{on}$) and unbinding ($a_{off}$) rates of anchors to the matrix, given by $$\varphi = \frac{a_{\it off}}{a_{on} + a_{\it off}}.$$

Note that φ=0 and φ=1 represent extremes where all anchors and no anchors are bound to the matrix, respectively.

Why Short-Lived Anchor-Matrix Bonds Maximize Trapping Potency:

Instinctively, one may expect that φ=0 maximizes the fraction of trapped nanoparticles and that trapping potency is reduced as φ rises until it is eliminated altogether when φ=1. Nevertheless, this was not supported by our experiments where IgG, anchored to the matrix with long-lived biotin-avidin bonds, failed to trap nanoparticles with the same potency as IgG that exhibit only weak and short-lived interactions with the matrix. To begin to understand why long-lived anchor-matrix bonds may compromise nanoparticle trapping, it is important to note that a nanoparticle is unlikely to simultaneously encounter multiple matrix-bound (immobilized) anchors unless the anchor concentration is very high (i.e., anchors are generically spaced at distances much greater than the dimensions of the nanoparticles). For example, we have previously observed trapping of ~100-200 nm nanoparticles and viruses at IgG concentrations of 1-3 μg/mL; the average distance between each IgG at these concentrations is roughly 440-630 nm. At these concentrations, if anchors are permanently bound to the matrix, the average number of anchors on each 100-200 nm nanoparticle that has been cross-linked to the matrix must be at most one. Conversely, to achieve an average distance of ≤100 nm between each IgG would require IgG concentrations in excess of 250 μg/mL, an exceedingly high concentration for a single anchor species.

Recall from the Smoluchowski encounter relation that when anchors are immobilized, the rate of a nanoparticle binding to an anchor is proportional to particle diffusivity $D_P$, whereas the binding rate of free anchors to the nanoparticle is proportional to $D_P+D_A$. Since we postulated that $D_A \gg D_P$, nanoparticles must encounter freely diffusing anchors much more frequently and quickly than matrix-bound anchors. Consequently, when φ>0, multiple anchors will begin to accumulate on the surface of the nanoparticle, and multiple bonds can form (i.e., $PA_n \rightarrow P(AM)_n$) when a freely diffusing nanoparticle-anchor complex encounters matrix constituents. While a single anchor might rapidly unbind from the matrix, resulting in a very short association lifetime of the complex, a nanoparticle-anchor complex with multiple nanoparticle-bound anchors, i.e., $PA_n$, can increase the collective crosslink lifetime because only one MAP bond is necessary to keep the nanoparticle immobilized at any given time. So long as the anchors stay bound to the nanoparticle, they do not diffuse away as quickly after the nanoparticle-anchor complex unbinds from the matrix as would individual free anchors, and thus can more rapidly rebind to the matrix. Assuming each anchor-matrix bond is independent, the $PA_n$ complex crosslink lifetime increases exponentially with the number of anchors n bound to the same nanoparticle, and it becomes exceedingly rare for all anchors to simultaneously unbind from the matrix. We therefore reach the seemingly counterintuitive conclusion that short-lived anchor-matrix bonds can actually facilitate more complete crosslinking of nanoparticles to the matrix.

Figure 18A:
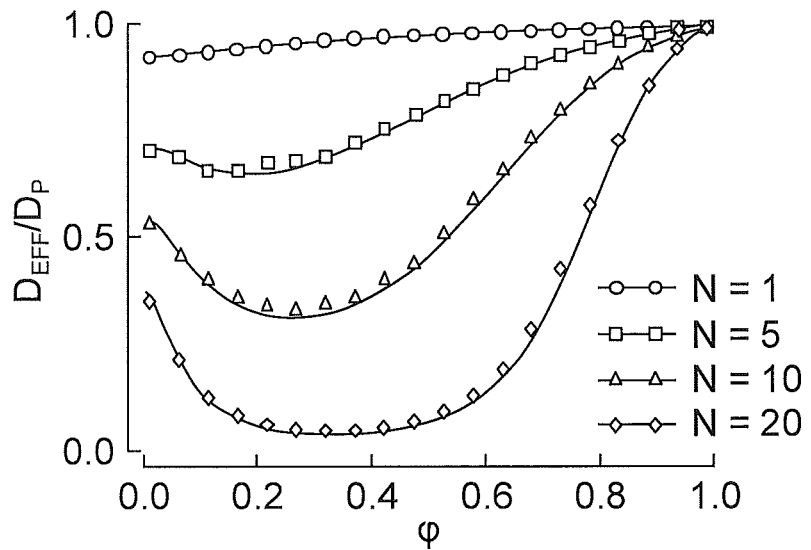
FIGS. 18A-18B show effective diffusivity vs. free fraction of anchors. The approximation [eq:Deff] is shown as solid curves and symbols show the Monte-Carlo simulation estimator [eq:4] with $10^6$ time steps. Different curves are shown for different values of (A) N, the maximum number of binding sites on the nanoparticle, and (B) $D_A/D_P$, the ratio of the anchor diffusivity to the nanoparticle diffusivity. Parameter values used were $\tau_{AP}/\tau_{AM}$=20, N=15, and $D_A/D_P$=20.

Of course, some fraction of A must bind to the polymer network with some probability or frequency; if φ=1, then anchors never bind to the matrix. It follows that the crosslink lifetime of a nanoparticle-anchor complex to the matrix must eventually begin to decrease as the anchor-matrix binding affinity is reduced below some optimal fraction of free anchors, $0<\varphi<1$, corresponding to the most robust cross-linking of nanoparticles to matrix.

We seek to precisely identify the optimal affinity $\varphi$ and timescale of anchor-matrix interactions for minimizing nanoparticle flux through a gel layer. To do so, we first define a characteristic length scale L of interest in the system (e.g., the height of a mucus layer lining the surface of the lung or GI tract). There are three timescales to consider: diffusion ($\tau_L=g/(2D_P)$), anchor-matrix interactions ($\tau_{AM}=1/(a_{on}+a_{off})$), and anchor-nanoparticle interactions ($\tau_{AP}=1/(D_A[A]R_0\ k_{off})$). The diffusion time scale determines the average amount of time needed to diffuse through a matrix layer. The two kinetic timescales characterize the average duration of consecutive bind-unbind events. We assume that L is large enough that many anchor-matrix and anchor-nanoparticle interactions can occur before the nanoparticles diffuse out of the system, i.e., $\tau_{AP}$, $\tau_{AM}<<\tau_L$, which allows us to derive an effective diffusivity for the nanoparticle $D_{eff}\leq D_P$ (see Methods section for the derivation) that characterizes the effective trapping potency of the anchors. Naturally, the smaller $D_{eff}$ is, the more immobilized the nanoparticle is: $D_{eff}D_P$ indicates anchors that have no effect on the native diffusivity of the nanoparticle, whereas $D_{eff}<D_P$ reflects anchors that can at least transiently immobilize the nanoparticle to the matrix. We now seek to explore how anchor-matrix affinity influences nanoparticle trapping under two important regimes: rapid yet short-lived anchor-matrix kinetics, where $\tau_{AM}<<\tau_{AP}$, and slow long-lived anchor-matrix kinetics, where $\tau_{AM}>>\tau_{AP}$.

If $\tau_{AM}>>\tau_{AP}$, then on the timescale of A/P kinetics, anchors do not bind to or unbind from the matrix. Because we assume that [A] is not unrealistically high (see above and Assumption 6), nanoparticles can effectively only bind to a single matrix-bound anchor at a time. In this regime, $D_{eff}$ is minimized when $\varphi=0$, i.e., very high anchor-matrix affinity (FIG. 2A, $\tau_{AP}/\tau_{AM}\sim 0.01$). Assuming $D_A/D_P=20$ and only 15 antigens on each 100 nm nanoparticle, this results in a $D_{eff}/D_P$ that is reduced ~55% on average compared to if anchors have no affinity to matrix (FIG. 17A), which translates to only a ~5% reduction in the fraction of nanoparticles that can penetrate a 50 μm thick layer over 2 hours (FIG. 17B).

A much different result is obtained with rapid and short-lived anchor-matrix bonds relative to anchor-nanoparticle bonds, i.e., $\tau_{AM}<<\tau_{AP}$. $D_{eff}/D_P$ for the same nanoparticle drops significantly as $\tau_{AP}/\tau_{AM}$ increases, with a nontrivial optimal $\varphi$ that minimizes $D_{eff}$ (FIG. 17A). Indeed, when $\tau_{AP}/\tau_{AM}$ approaches 20 and with the steady state free fraction of anchors in the ~20-40% range (i.e., $\varphi\sim 0.2$-$0.4$), $D_{eff}/D_P$ is reduced by over 90%, effectively restricting transport of the nanoparticles. This drop in $D_{eff}$ directly correlates to >50% reduction in the fraction of nanoparticles that can penetrate across a 50 μm thick matrix layer over 2 hrs, a greater than 10-fold increase in trapping potency compared to the long-lived anchor-matrix bonds scenario (FIG. 17B). Increases in $\tau_{AP}/\tau_{AM}$ also directly reduces the amount of anchors needed to reduce the flux of nanoparticles penetrating and exiting the matrix layer (FIG. 17C). These results confirm Condition 1 of our proposed model, namely that short-lived anchor-matrix bonds ($\tau_{AM}<<\tau_{AP}$) maximizes trapping potency.

Efficient Crosslinking of Nanoparticles to Matrix Also Requires Multiple Antigens and Rapid Anchor Diffusivity:

Hypothetically, if there is only one epitope available per nanoparticle, then at most only one anchor can bind to the nanoparticle (i.e., N=1). Naturally, in this scenario, $D_{eff}/D_P$ would decrease monotonically as $\varphi\rightarrow 0$, since maximum trapping is achieved when the nanoparticle-bound anchor never dissociates from the matrix, as shown in FIG. 18A. In contrast, for N>1, $D_{eff}/D_P$ is an exponentially decreasing function of N: the more antigen sites available on a nanoparticle, the more likely and quickly the nanoparticle will accumulate anchors on its surface and become trapped in the matrix (FIG. 18A). With even a modest number of anchor binding sites on each nanoparticle (N~20), nanoparticle $D_{eff}$ can be reduced by over 90% when combined with rapid (i.e. $\tau_P/\tau_M=20$) and weak (i.e. $\varphi$~0.2-0.4) anchor-matrix interactions. To place this in perspective, Influenza and Herpes Simplex Virus have hundreds of hemaglutinin and gD glycoprotein epitopes per viral particle, respectively. These results confirm Condition 2 of our proposed model.

Figure 18B:
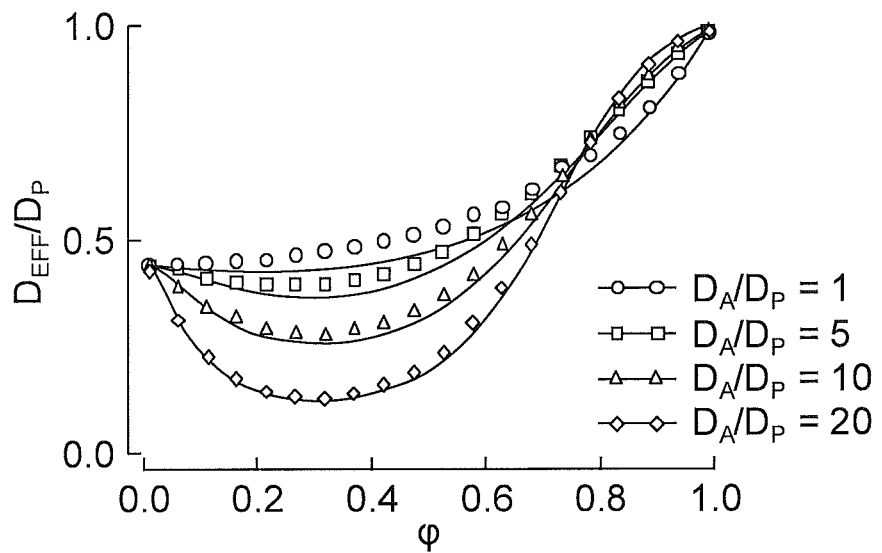

In addition to the number of binding sites, the rate of anchor accumulation depends on the frequency with which anchors can collide with the nanoparticle. The latter is in turn proportional to the diffusivity of the anchor as predicted by the Smoluchowski encounter relation. Although greater nanoparticle diffusivity $D_P$ can theoretically increase the encounter and anchor accumulation rate on the nanoparticle, this also reduces the time $\tau_L$ available for sufficient quantities of anchor to accumulate on the nanoparticle before the nanoparticle diffuses through the barrier fluid. As shown in FIG. 18B, nanoparticle $D_{eff}/D_P$ drops as $D_A$ increases; thus, anchors that are smaller and more mobile than the nanoparticle are preferred for nanoparticle trapping. These results confirm Condition 3 of our proposed model.

Figure 19A:
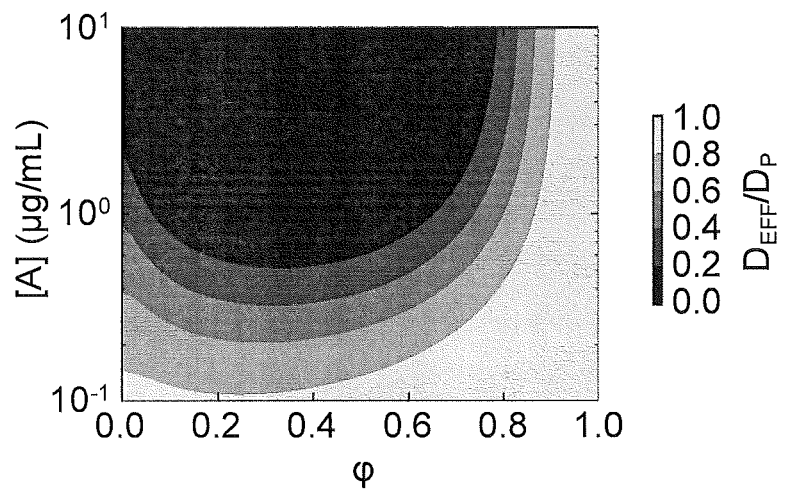
FIGS. 19A-19C show heat maps of the (A) effective diffusivity and (B-C) Probability of penetration of a gel layer within two hours. The y axis is the anchor concentration for 170 KD anchors. The x axis is (A-B) the fraction of free anchors and (C) the thickness of matrix layer. Parameter values used were: (A) $D_A/D_P$=20 and N=20; (B) $D_A/D_P$=20, N=20, and L=50 µm; and (C) $D_A/D_P$=10, N=20, and $\varphi$=0.72.
Figure 19B:
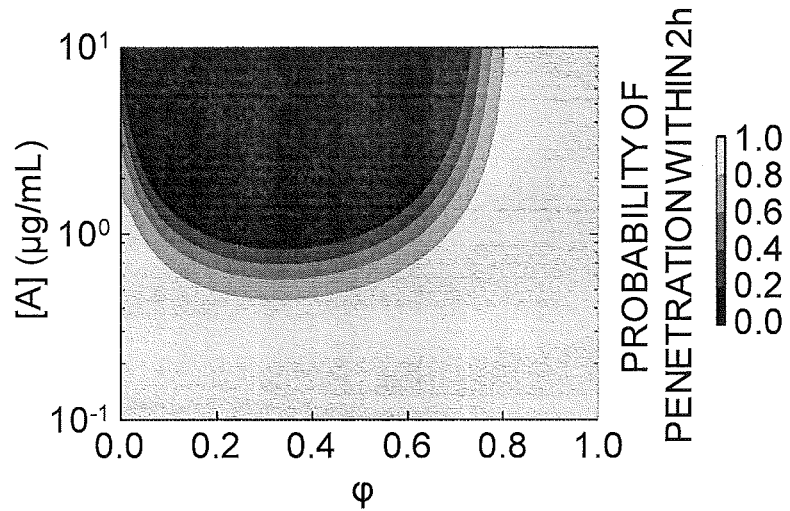
Figure 19C:
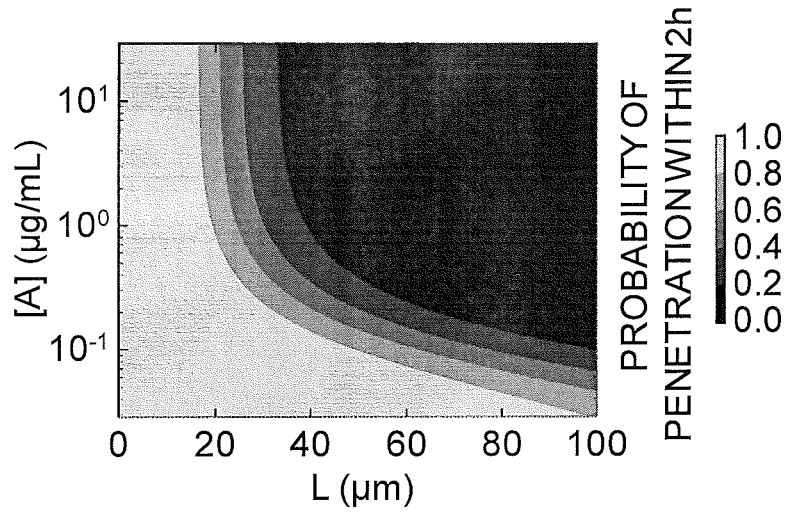

Balancing Thickness of Polymeric Matrices and Anchor Concentrations to Maximize Trapping Potency:

The barrier properties of biogels are naturally dependent on both the thickness of the gel layer as well as the concentration of the molecular anchors. This is particularly relevant for diffusional barriers such as mucus and basement membranes, where minimizing the fraction of viruses that can penetrate through the gel layer can directly reduce the probability of transmission or spread of the infection systemically. To address the balance between these two parameters, we assert that the most effective balance of timescales to immobilize nanoparticles is $\tau_{AM} \ll \tau_{AP} \ll \tau_L$ (i.e., imposing Conditions 1 and 4 of our model). We have already shown above that maximal trapping occurs with rapid anchor-matrix binding kinetics i.e. $\tau_{AM} \ll \tau_{AP}$. In addition, as explained above, in order for nanoparticles to become trapped in the matrix, the nanoparticle must be captured by at least one anchor before it diffuses through the matrix. Recall that the average time the nanoparticle, unhindered by anchors, needs to diffuse through a matrix layer is $\tau_L = L^2/(2D_P)$. Hence, the matrix layer thickness must be $L \gg \sqrt{2D_P \tau_P}$ for anchors to have sufficient time to accumulate on the nanoparticle. To illustrate the effect of the timescale $\tau_D$, we use a numerical approximation of the solution to equation [eq:9] (see Methods Section), and compute the probability that a nanoparticle can diffuse across a polymer matrix layer of thickness L. We term this the absorption probability; a low absorption probability indicates effective trapping by anchors. Not surprisingly, $D_{eff}/D_P$ (FIG. 19A) and the absorption probability (FIG. 19B) both decrease with increasing anchor concentration (FIG. 19A), in both cases approaching a minimum $D_{eff}/D_P$ when $\varphi$~0.35. Interestingly, when we compare the relative importance of L vs. anchor concentrations, we found that exponentially higher anchor concentrations are required when L is smaller than ~40-50 μm thick in order to maintain a comparably effective diffusional barrier (FIG. 19C), implying that effective diffusional barriers in vivo should be at least 40-50 μm thick. These estimates agree remarkably well with both (i) the thickness of mucus coatings lining the respiratory, gastrointestinal and cervicovaginal tracts (typically ~50-100+ μm), as well as (ii) the Ab concentrations present in mucus (typically ~0.1-10 μg/mL) (Wang et al., *Mucosal Immunol.* 7:1 (2014)). This analysis confirms Condition 4 of our proposed model.

Short-Lived Anchor-Matrix Bonds Enable Robust Trapping of Multiple Nanoparticle Species by Minimizing Potential Saturation of Anchor-Binding Sites within the Matrix:

To selectively control transport against multiple species of nanoparticles in the same polymeric matrix, such as trapping a diverse array of pathogens that impinge on mucus coating the airways and gastrointestinal epithelium, many corresponding anchor species must coexist without impeding each other's trapping potency. In other words, even when anchors that bind any given species represent only a tiny fraction of all anchors present, the specific anchor-matrix affinity must remain unaltered in order to maintain comparable trapping potency. We introduce the term trapping robustness to describe the ability to immobilize multiple nanoparticle species.

Figure 20:
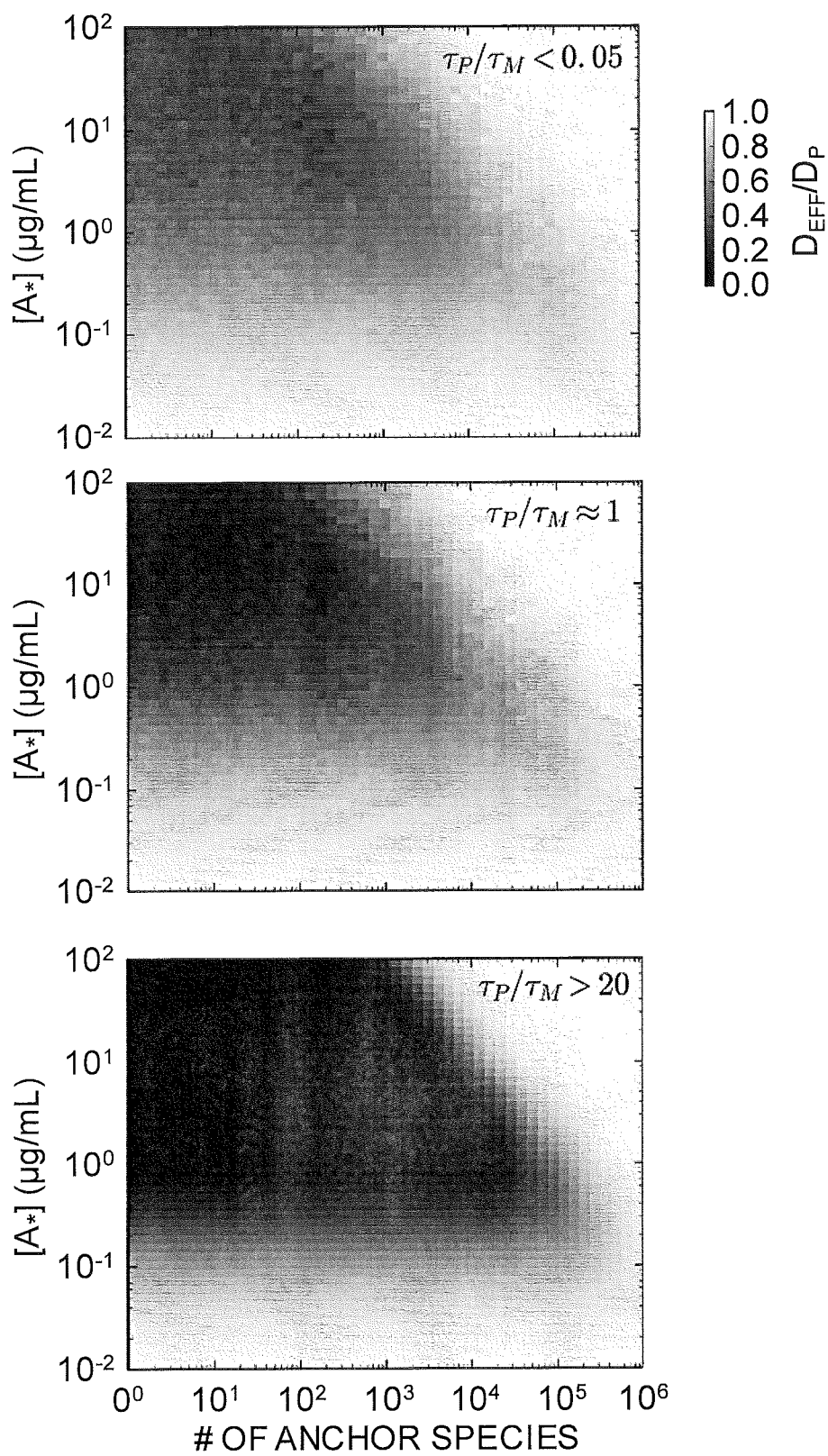
FIG. 20 shows the effective diffusivity for the case of saturation of binding sites by anchor species. Each pane shows a heat map for a different values of the timescale separation $\tau_{AP}/\tau_{AM}$. Parameter values used were $D_A/D_P$=20, N=20, and [M]=$10^5$/µm$^3$ (this concentration is relevant for a 2% gel with 10 anchor binding sites per matrix).

Since the concentration of matrix constituents are finite, the number of anchor binding sites in a polymeric gel must by definition be finite. Thus, if anchor-matrix bonds are long lived, a matrix-bound anchor prevents other anchors from binding to the same binding site on the matrix. Thus, at concentrations sufficient for trapping (e.g., ~1-5 μg/ml IgG), the system could accommodate only a relatively limited number of anchor species ($<10^3$ for a 2% w/v gel, assuming 10 anchor binding sites per matrix molecule and an average MW of ZZ MDa) before additional anchors become unable to effectively reduce $D_{eff}/D_P$ (FIG. 20). However, when $\tau_{AM} \ll \tau_{AP}$, the short duration of anchor-matrix bonds would greatly increase the number of unoccupied anchor binding sites available on the matrix at any moment in time. This in turn enables the anchor-matrix system to both immobilize a far greater number of particle species simultaneously as well as reduce the minimum $D_{eff}/D_P$ that could be achieved with each anchor (FIG. 20). Indeed, when $\tau_{AP}/\tau_{AM} \geq 20$, a biogel reinforced with appropriate molecular anchors can effectively immobilize at least 30-fold more (i.e. ~$3 \times 10^4$) distinct nanoparticle species without appreciable loss in trapping potency (i.e., similar minimum $D_{eff}/D_P$ for all species), underscoring the potential trapping robustness of the system. Altogether, these results confirm Condition 5 of our proposed model.

Figure 21:
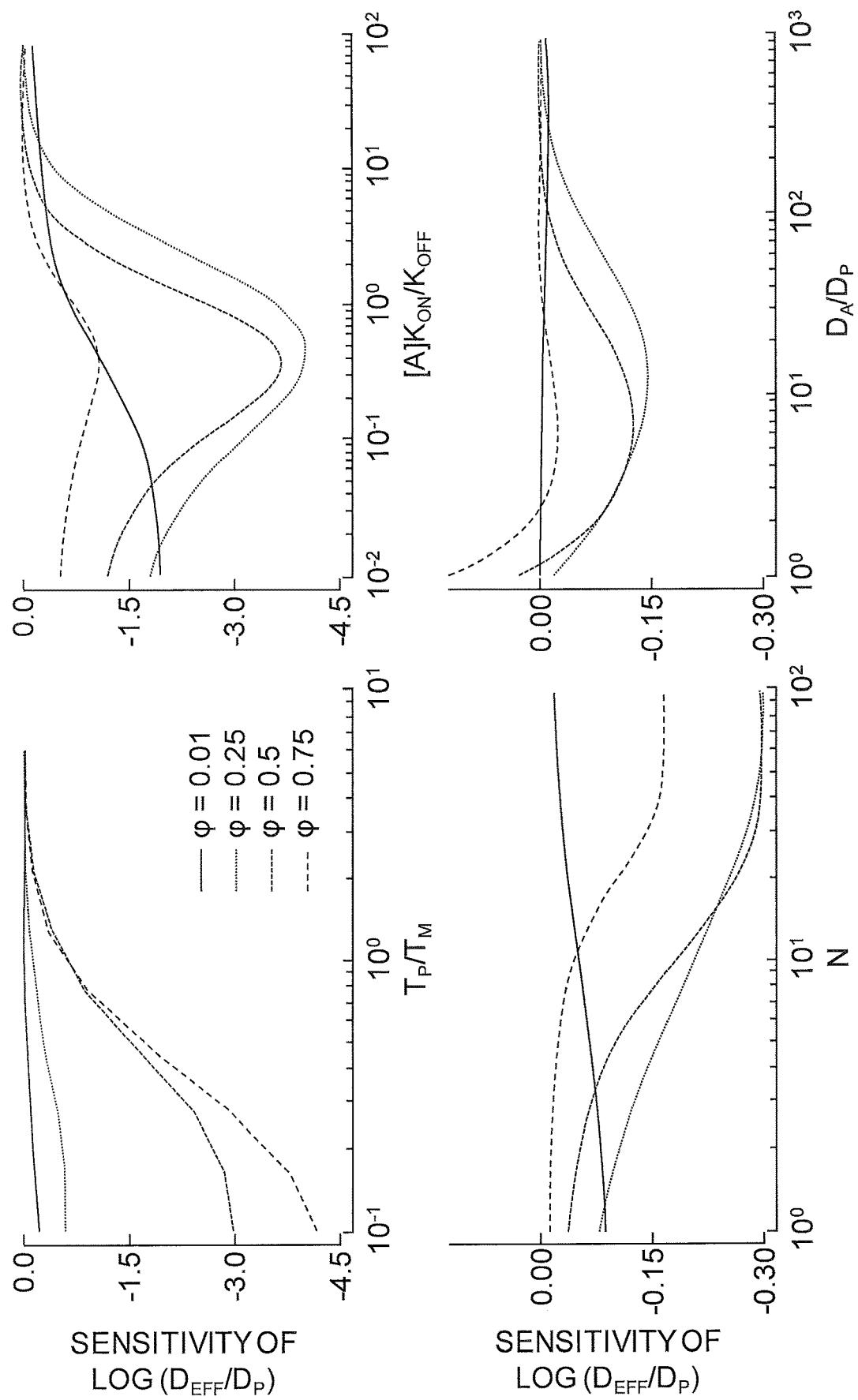
FIG. 21 shows sensitivity analysis for $\tau_P/\tau_M$, N, and $D_A/D_P$. The sensitivity was defined as $$\frac{\partial}{\partial p} \log\left(\frac{D_{eff}}{D_P}\right) \approx \frac{\Delta D_{eff}}{D_{eff} \Delta p},$$

Finally, we examined the relative importance for each of the parameters described above by evaluating the partial derivatives of $\log(D_{eff}/D_P)$ under a range of parameter values. We observed the greatest impact with $\tau_{AP}/\tau_{AM}$ (in particular at low $\tau_{AP}/\tau_{AM}$ values) and the rates of anchor accumulation $k_{on}[A]$, with more modest impact with changes in antigenic epitope density (i.e., maximum number of bound anchor) N and the diffusivity of anchors relative to the nanoparticle species $D_A/D_P$ (FIG. 21). These results underscore short-lived anchor-matrix bonds relative to anchor-nanoparticle bonds as a crucial separation of timescales for enabling molecular anchors that can substantially enhance the barrier properties of either biological or synthetic polymeric matrices to multiple nanoparticle species.

SUMMARY

A critical function of polymeric matrices in biological systems is to exert selective control over the transport of thousands of nanoparticulate species. By eliminating the need for matrix constituents to recognize diverse antigenic species, an anchor-matrix system can enable an effective diffusional barrier against many nanoparticle species while maintaining relatively static biochemistry and microstructure of the matrix. This suggests that anchors, such as IgG and other antibodies produced by the immune system that can adapt and bind diverse molecular entities, represent an ideal platform to control nanoparticle transport. Here, we demonstrate both experimentally and theoretically that short-lived anchor-matrix interactions represents the critical attribute enabling potent and robust control over nanoparticle transport in biogels. Given the weak and short-lived interactions between individual IgG antibodies and Matrigel constituents, it was reasonable to conclude that IgG exerts only limited selective control over nanoparticle transport in Matrigel®. In contrast, the observed trapping potency against pathogens and particulates is a cooperative effect of multiple IgG. Combined with our earlier observations that IgG can potently immobilize viruses and nanoparticles in different mucus secretions, it is likely that the proposed strategy, whereby the barrier properties are tuned by modest concentration of highly mobile molecular anchors with exceedingly short anchor-matrix bond times relative to anchor-nanoparticle bond times, is a universal feature of biogels in living systems. Our findings provide a blueprint for engineering of molecular anchors with optimal short-lived anchor-matrix bonds to selectively tune the barrier properties of polymeric gels.

EXAMPLE 4

Selective Tuning of the Barrier Properties of Hydrogels Using IgG and IgM Antibodies Biopolymeric matrices are ubiquitously present in living systems, and provide structural support and mechanical function essential to health (Kruegel et al., Cell. Mol. Life Sci 67:2879 (2010)). For example, extracellular matrices known as basement membranes (BM) provide a scaffold for epithelial cells to anchor to underlying loose connective tissue (Kruegel et al., Cell. Mol. Life Sci 67:2879 (2010)). Similarly, mucus gels lubricate mucosal surfaces such as the gastrointestinal and female reproductive tracts to allow for passage of food or copulation (Lai et al., Adv. Drug Deliv. Rev. 61:86 (2009)), and the vitreous humor maintains the spherical shape of the eye critical for proper vision (Kokavec et al., Clin. Exp. Ophthalmol. 44:597 (2016)).

To attain the necessary viscous and elastic modulus for suitable biological functions, these biopolymers typically undergo extensive crosslinking or entanglement to create a viscoelastic gel. Such supramolecular structure of network matrices in turn enables a second important function: selectively permeable membranes that determine which substances will be able to enter the epithelium. Naturally, the matrices can restrict diffusion by steric obstruction when objects are larger than the pores present, such as preventing malignant cells from invading the deeper tissues (Arends et al., PLoS One 10:1 (2015)) or aerosolized particles from reaching the epithelium along conducting airways (Cheng et al., AAPS PharmSciTech 15:630 (2014)). In order to restrict diffusion of entities not adequately trapped by steric obstruction, biopolymeric matrices must rely on adhesive interactions (Lieleg et al., Biophys. J. 97:1569 (2009)). It is highly unlikely that matrices with relatively static biochemical structures can adhesively immobilize, on their own, the full diversity of pathogens and macromolecules present in any living system. Indeed, the vast majority of viruses that transmit at mucosal surfaces (HIV, HSV, HPV, Norwalk, etc.) evade adhesion to mucins and diffuse rapidly through the low viscosity interstitial fluids that fill the pores of mucus gels (Olmsted et al., Biophys. J. 81:1930 (2001))[7]. Thus, to selectively immobilize a diverse array of entities smaller than the pores of the matrices, it is necessary to utilize highly adaptive third-party crosslinkers that can evolve and cross-link viruses and nanoparticles to matrix constituents.

Antibodies (Ab) represent a potential platform of cross-linkers that can be readily generated by living systems. Specifically, due to the process of somatic hypermutation and affinity maturation, antibodies possessing high specificity against a diverse array of pathogens can be readily induced and secreted. Here, we investigated whether Ab can facilitate trapping of pathogens in extracellular matrices of the basement membrane (BM). Our results demonstrate that Ab-matrix interaction is likely a long overlooked molecular mechanism enabling selective permeability of BM and presumptively other biopolymeric matrices.

Materials and Methods

Preparation of PEG-Coated Nanoparticles:

To produce PEGylated nanoparticles (PS-PEG), we covalently modified 200 nm fluorescent, carboxyl-modified polystyrene beads (PS-COOH; Invitrogen) with 2 kDa methoxy polyethylene glycol amine (PEG; Sigma) via a carboxyl-amine reaction, as published previously (Lai et al., Proc. Natl. Acad. Sci. USA 104:1482 (2007); Yang et al., Mol. Pharm. 11:1250 (2014)). Particle size and $\zeta$-potential were determined by dynamic light scattering and laser Doppler anemometry, respectively, using a Zetasizer Nano ZS (Malvern Instruments, Southborough, Mass.). Size measurements were performed at 25° C. at a scattering angle of 90°. Samples were diluted in 10 mM NaCl solution, and measurements were performed according to instrument instructions. PEG conjugation was also confirmed by a near-neutral $\zeta$-potential (Table 2) (Lai et al., Proc. Natl. Acad. Sci. USA 104:1482 (2007)). Dense PEG grafting (>1 PEG/nm$^2$) was further verified using the fluorogenic compound 1-pyrenyl-diazomethane (PDAM) to quantify residual unmodified carboxyl groups on the polystyrene beads (Yang et al., Mol. Pharm. 11:1250 (2014)).

Preparation of BM, LAM, and Collagen Gels:

A mixture of the following was added to a custom-made micro-volume (~20 µL) glass chamber slide: (i) growth-factor reduced Matrigel (Corning), high-concentration laminin/entactin (Corning), or collagen; (ii) BSA (Sigma); (iii) Eagle's Minimum Essential Medium (EMEM, Lonza Bio-Whittacker); (iv) fluorescent PS-COOH (Ex: 505 nm, Em515 nm) and PS-PEG (Ex: 625 nm, Em645 nm) nanoparticles; and (v) different Ab. The mixture was incubated at 37° C. for 45 minutes in a custom hydration chamber, then sealed and incubated for another 30 minutes prior to microscopy. Final concentrations of reagents in slides were as follows: 2.2 mg/mL Matrigel, 1 mg/mL BSA, ~4.3*10$^8$ beads/mL for both PEG- and COOH-modified nanoparticles, antibody as listed, EMEM, q.s. In LAM experiments, the final concentration of LAM complex (Corning) was 1.5 mg/mL (comparable to the concentration of laminin in 2.2 mg/mL Matrigel). In COL experiments, the final concentration of COL was as high as 3 mg/mL. Trapping of PS-COOH beads in BM was used as an internal control in all microscopy experiments as a measure of complete polymerization of BM constituents.

Native Anti-PEG IgG and IgM and Deglycosylation:

Anti-PEG IgG$_1$ (CH2074, Silver Lake Research) and anti-PEG IgM (AGP4, IBMS) were used as test Ab and anti-Biotin IgG (33, Santa Cruz) and anti-Vancomycin IgM (2F10, Santa Cruz) were used as control Ab. All native Ab were used as is provided by the manufacturer. To prepare deglycosylated Ab, N-glycans on anti-PEG IgG and IgM were removed with rapid non-reducing PNGase F enzyme (New England Biolabs) according to manufacturer's protocol. The deglycosylation reaction was confirmed with two NuPAGE 4-12% Bis-Tris gels (Novex) in MOPS buffer. The first gel was transferred to a nitrocellulose membrane (Novex) with a Semi-Dry Blotter (Novex), blocked with carbo-free buffer (Vector Labs), labeled overnight at 4° C. in 2 µg/mL biotinylated concavalin A (Vector), and probed with anti-biotin peroxidase (Vector) before imaging with Clarity Western Blot ECL Substrate (BioRad) in a FluorChemE unit (Cell Biosciences). The second gel was silver stained with Pierce Silver Stain Kit (Thermo Scientific) and imaged with the same unit (FIG. 22). The remaining deglycosylated IgG and IgM was buffer-exchanged into PBS using 50 MWCO spin-x columns (Corning), quantified based on $A_{280}$, and their binding affinity to PEG was measured using ELISA.

High Resolution Multiple Particle Tracking:

The trajectories of the fluorescent particles were recorded using an EMCCD camera (Evolve 512; Photometrics, Tucson, Ariz.) mounted on an inverted epifluorescence microscope (AxioObserver D1; Zeiss, Thornwood, N.Y.), equipped with an Alpha Plan-Apo 100x/1.46 NA objective, environmental (temperature and $CO_2$) control chamber and an LED light source (Lumencor Light Engine DAPI/GFP/543/623/690). 20 s videos (512×512, 16-bit image depth) were captured with MetaMorph imaging software (Molecular Devices, Sunnyvale, Calif.) at a temporal resolution of 66.7 ms and spatial resolution of 10 nm (nominal pixel resolution 0.156 µm/pixel). The tracking resolution was determined by tracking the displacements of particles immobilized with a strong adhesive, following a previously described method (Apgar et al., *Biophys. J.* 79:1095 (2000)). Particle trajectories were analyzed using MATLAB software as described previously (Wang et al., *J. Control. Release* 220:37 (2015)). Sub-pixel tracking resolution was achieved by determining the precise location of the particle centroid by light-intensity-weighted averaging of neighboring pixels. Trajectories of n≥40 particles per frame on average (corresponding to n≥100 total traces) were analyzed for each experiment, and 3-4 independent experiments were performed for each condition. The coordinates of particle centroids were transformed into time-averaged mean squared displacements (MSD), calculated as $<\Delta r^2(\tau)>=[x(t+T)-x(t)]^2+[y(t+\tau)-y(t)]^2$ (where $\tau$=time scale or time lag), from which distributions of MSDs and effective diffusivities ($D_{eff}$) were calculated, as previously demonstrated (Lai et al., *Proc. Natl. Acad. Sci. USA* 104:1482 (2007); Dawson et al., *J. Biol. Chem.* 278:50393 (2003); Suh et al., *Adv. Drug Deliv. Rev.* 57:63 (2005)). MSD may also be expressed as $MSD=4D_0\tau^\alpha$, where $\alpha$, the slope of the curve on a log-log scale, is a measure of the extent of impediment to particle diffusion ($\alpha=1$ for pure unobstructed Brownian diffusion; $\alpha<1$ indicates increasing impediment to particle movement as a decreases). Mobile particles were defined as those with $D_{eff} \geq 10^{-1}$ µm²/s at $\tau=0.2667$ s (this $\tau$ corresponds to a minimum trajectory length of 5 frames), based on multiple datasets of mobile and immobile nanoparticles (e.g., PS and PS-PEG nanoparticles) in human mucus (Lai et al., *Proc. Natl. Acad. Sci. USA* 104:1482 (2007); Lai et al., *Proc. Natl. Acad. Sci. USA* 107:598 (2010)).

Biolayer Interferometry Experiments:

On an Octet QK instrument (ForteBio), streptavidin biosensors (ForteBio) hydrated in running buffer (PBS) were loaded with biotinylated biopolymer or biotinylated PEG at 5 µg/mL for 600 s. Sensors were washed in running buffer for 180 s and a baseline set in running buffer for 300 s. Antibody (IgG or IgM) at different concentrations was associated with these customized biosensors for 600 s and dissociated for 600 s. Loading ligands and analytes were diluted in running buffer. Data were adjusted for reference sensors and baseline values and aligned to dissociation, then processed with Savitzky-Golay filtering. Analysis was performed with ForteBio software using a 1:1 global curve fit model to obtain values for $k_{on}$, $k_{off}$, and $K_D$.

*Salmonella* Invasion Across BM:

BM (final concentration 2.2 mg/mL) or LAM (final concentration 1.5 mg/mL) with Luria Broth (LB, BD Falcon), BSA, and varying concentrations of anti-*Salmonella typhimurium* $IgG_1$ (6331; WHERE) were mixed and incubated for 2 hours at 37° C. in the upper chamber of a HTS FluoroBlok MultiWell System with 3.0 µm pores (BD Falcon) in a custom hydration chamber. After confirming mobility in the above-mentioned epifluorescence microscope, GFP-labeled *S. typhimurium* in 104 LB was then added to the top of each well, and 200 µL LB to each well in the bottom chamber. After 2 hours of incubation at 37° C., the top chamber was removed and OD600 in the lower chamber was measured with a SpectraMax M2 (Molecular Devices). Experiment was performed in triplicate, n=3.

Statistical Analysis:

MSD data were log-transformed and compared within groups using a repeated-measures two-way ANOVA and post hoc Tukey test. Log-transformed average $D_{eff}$ and % mobile were compared with ANOVA and subsequent Tukey's HSD tests. Binding curve $K_D$, $k_{on}$, and $k_{off}$ were compared with two-way ANOVA and post hoc Tukey test. *Salmonella* invasion data was normalized within each replicate by controlling for background (defined as OD600 of LB only) and maximal invasion of *Salmonella* in a given matrix. Data were compared within groups using a repeated-measures two-way ANOVA and post hoc Neuman-Keuls test. In all analyses, global $\alpha=0.05$. Error bars and ± represent SEM.

Results

PEG-Binding IgG and IgM Immobilizes PEG-Coated Nanoparticles in BM:

To begin to investigate whether the barrier properties of BM can be selectively tuned, we first mixed fluorescent polystyrene nanoparticles modified with either carboxyl groups (PS-COOH) or a dense layer of polyethylene glycol (PS-PEG) into reconstituted BM from Engelbreth-Holm-Swarm sarcoma (commercially available as Matrigel®) and performed high resolution multiple particle tracking to quantify the diffusion of hundreds of individual nanoparticles in each specimen. In good agreement with previous reports (Lieleg et al., *Biophys. J.* 97:1569 (2009)), nearly all PS-PEG nanoparticles exhibited largely unhindered Brownian motion, capable of diffusing many microns on the order of seconds, hindered only 1.6-fold compared to its movement in water (FIGS. 23A-23E). In contrast, PS-COOH beads in the same BM specimen were extensively immobilized, exhibiting a geometrically averaged ensemble effective diffusivity ($<D_{eff}>$) ~4000-fold reduced compared to PS-PEG (FIGS. 23A-23E; p<0.0018). Only 0.2%±0.09% of PS-COOH beads were classified as mobile (possessing $<D_{eff}>$ in excess of $10^{-6}$ mm²/s) vs. 96%±2% for PS-PEG beads. The effective immobilization of PS-COOH but not PS-PEG nanoparticles confirms BM affords a sufficiently rigid matrix that can immobilize virus-sized nanoparticles by adhesive interactions, and that PS-PEG nanoparticles are adequately modified with PEG to evade adhesive interactions with the matrix constituents.

We next tested whether exogenously introduced Ab can specifically immobilize the otherwise readily diffusing PS- PEG beads in BM. The addition of control IgG did not appreciably alter the diffusive motion of PS-PEG; the $<D_{eff}>$ of PS-PEG were slowed only ~1.6 fold compared to their theoretical speeds in water (Table S1). However, in BM treated with anti-PEG IgG to a final Ab concentration of 10 μg/mL, the majority of PS-PEG became effectively immobilized, moving less than the particle diameter over the course of 20 s movies, similar to PS-COOH nanoparticles (FIG. 24A). Indeed, the $<D_{eff}>$ of PS-PEG was reduced by ~17-fold compared to control IgG (FIG. 24B), and the mobile fraction was reduced from 96±1% in control IgG to 21±9% (p=0.018). The impediment to free Brownian diffusion caused by anti-PEG IgG was also reflected by the slope a from the log-log plot of geometrically averaged ensemble mean squared displacements <MSD> vs. time scale plots (α=1 for pure unobstructed Brownian diffusion, e.g., particles in water, and a becomes smaller and approaches zero as obstruction to Brownian diffusion increases): the average α value was 0.88 and 0.55 for PS-PEG in control IgG- and anti-PEG IgG-treated BM, respectively (p=0.0014 vs. control). We further reduced the anti-PEG IgG concentrations in BM and observed comparable trapping potency at 5 μg/mL (FIG. 1), but not at 1 μg/mL. These results underscore the ability for antigen-specific IgG to immobilize virus-sized nanoparticles in BM.

TABLE 2

Effective diffusivity of PEG beads with IgG and IgM antibodies in BM and LAM as compared to the theoretical diffusivity of PEG beads in water at 37° C.

| Antibody | Matrix | $D_{water}/D_{matrix}$ |
| --- | --- | --- |
| None (PS-COOH) | BM | 5943.9 |
| None (PS-PEG) | BM | 1.53 |
| Control IgG | BM | 1.6 |
| IgG 5 μg/mL | BM | 26.0 |
| IgG 10 μg/mL | BM | 26.7 |
| Control IgM | BM | 0.6 |
| IgM 1 μg/mL | BM | 61.8 |
| IgM 3 μg/mL | BM | 136.5 |
| IgM 5 μg/mL | BM | 240.5 |
| Deg. IgG 10 μg/mL | BM | 11.6 |
| Deg IgM 5 μg/mL | BM | 21.8 |
| Control IgG | LAM | 8.6 |
| IgG 10 μg/mL | LAM | 187.2 |
| Control IgM | LAM | 6.2 |
| IgM 5 μg/mL | LAM | 242.6 |

Figure 25C:
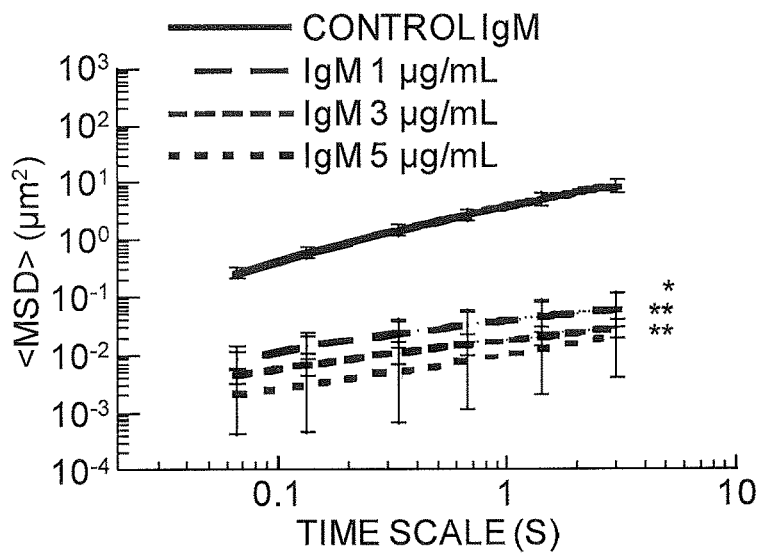
Figure 25D:
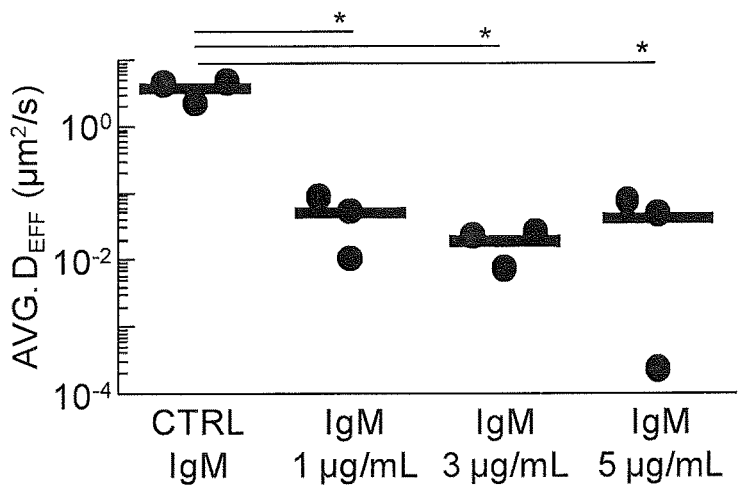
Figure 25E:
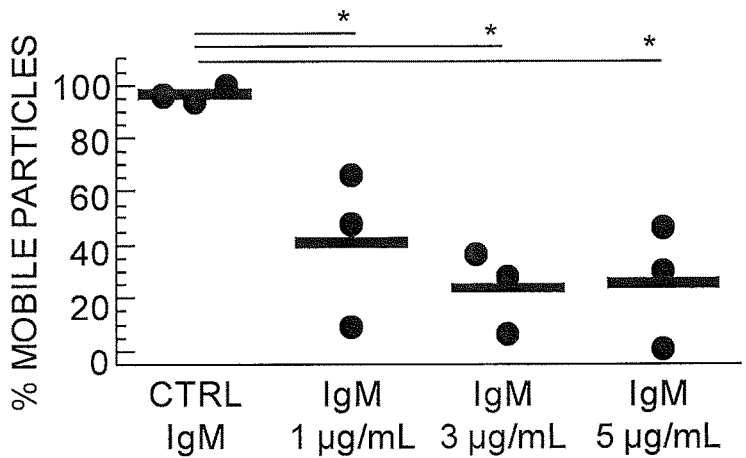

In addition to IgG, another major class of antibody is IgM, the pentameric antibody that occurs early in the adaptive immune response against foreign pathogens. We therefore also investigated whether IgM can also immobilize virus-sized nanoparticles in BM. Addition of control IgM did not alter the diffusion of PS-PEG; the $<D_{eff}>$ of PS-PEG were slowed to only ~0.6 fold compared to their theoretical speeds in water (Table 2), with 97±2% of the nanoparticles exhibited $<D_{eff}>$ in excess of $10^{-6}$ mm$^2$/s. In contrast, anti-PEG IgM immobilized an even greater fraction of PS-PEG than anti-PEG IgG, even at lower concentrations (FIGS. 25A and 25B). Anti-PEG IgM at 5 μg/mL reduced the <MSD> of PS-PEG in BM by ~90-fold compared to control IgM (FIG. 25C), reflecting a drop in the mobile fraction to 26±13% (FIG. 25E). Anti-PEG IgM also reduced the average a value of PS-PEG from 0.86 to 0.61 (p=0.0014 vs. control), underscoring the extent of antibody-mediated immobilization. Anti-PEG IgM mediated potent trapping of PS-PEG beads even at 1 and 3 μg/mL, reducing the $<D_{eff}>$ by 62- and 137-fold, respectively. Surprisingly, despite the common assumption that IgM can mediate efficient agglutination, we did not observe appreciable nanoparticle agglutination in BM with anti-PEG IgM.

Figure 26A:
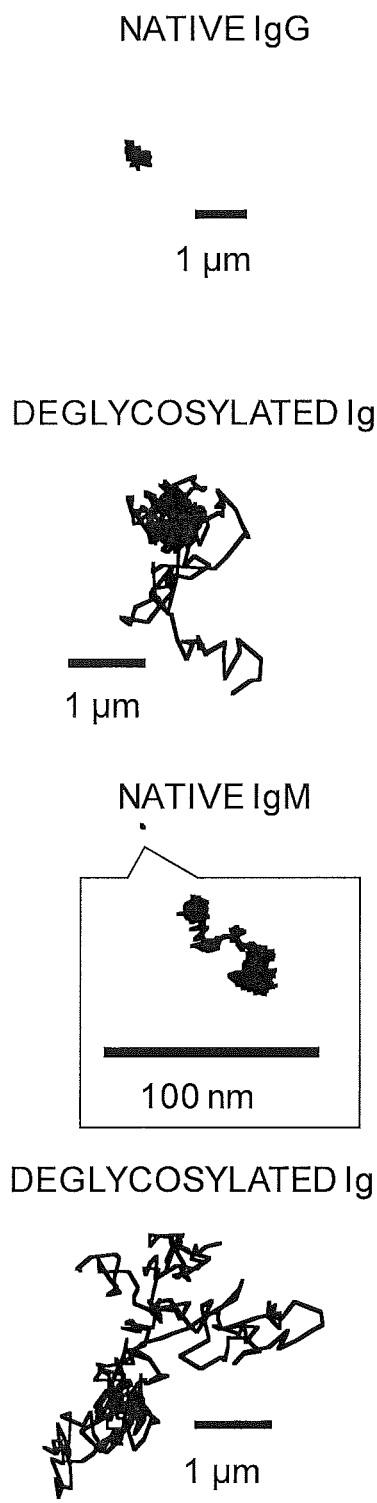
Figure 26B:
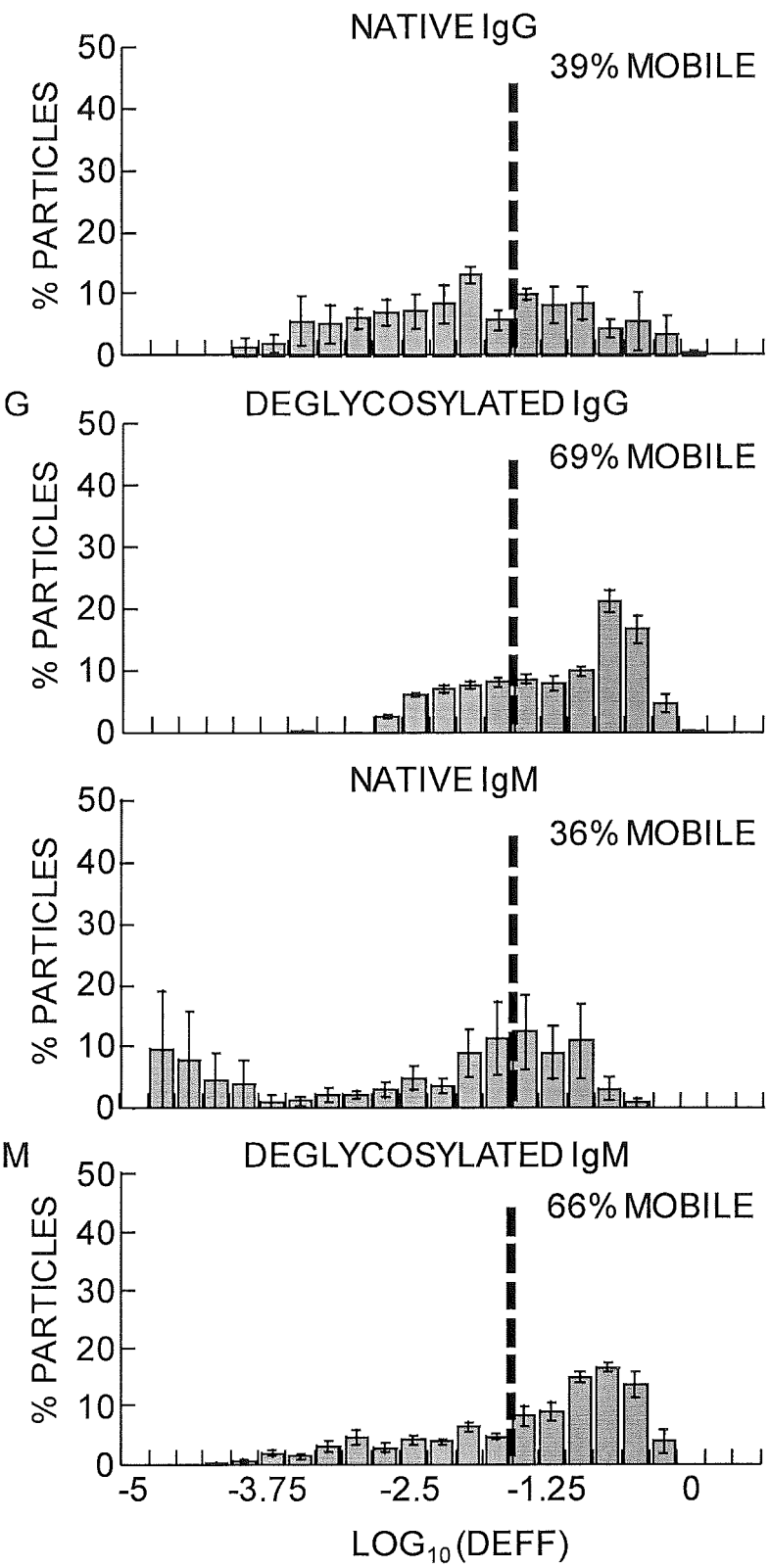
Figure 26C:
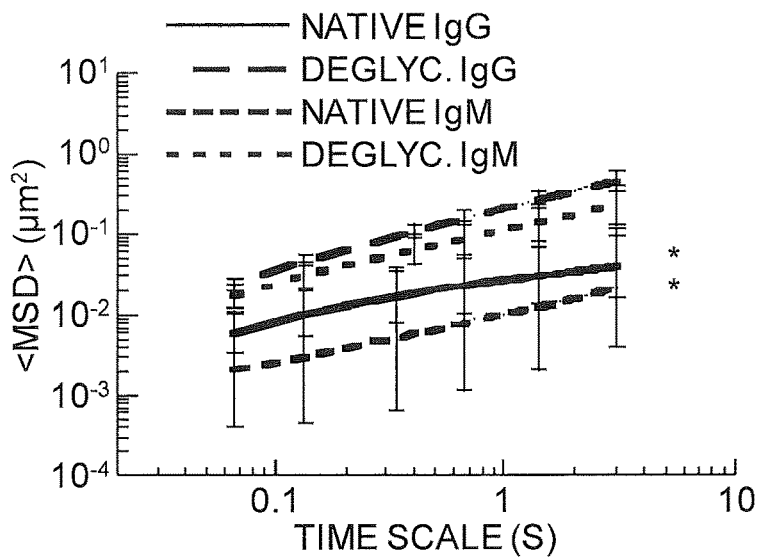
Figure 26D:
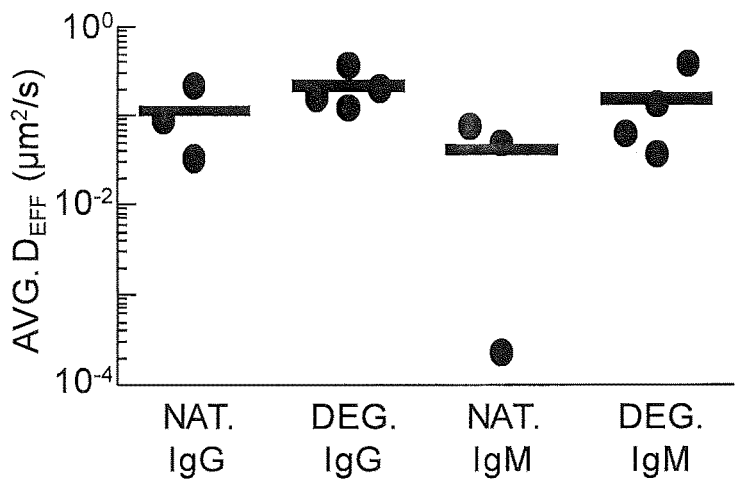
Figure 26E:
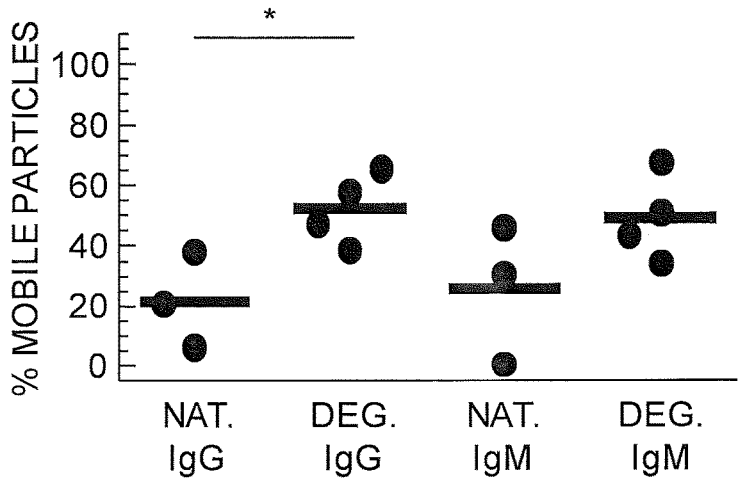
Figure 27A:
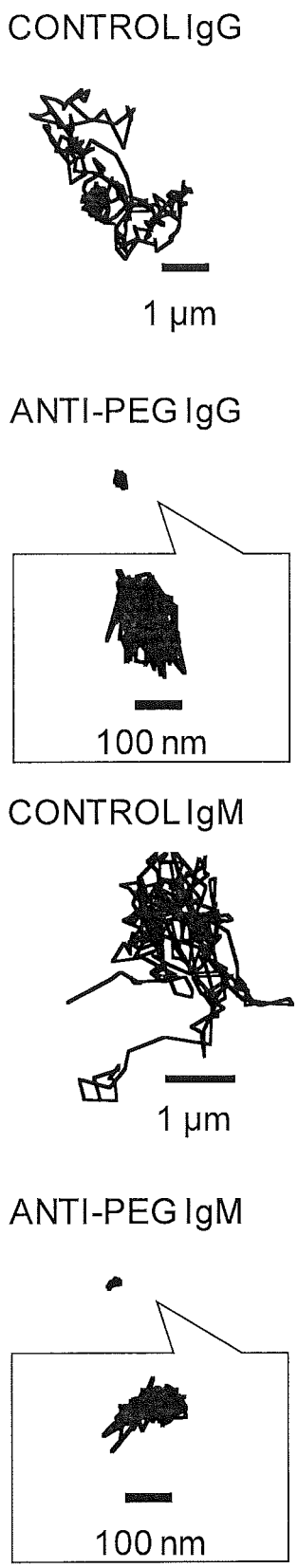
Figure 27B:
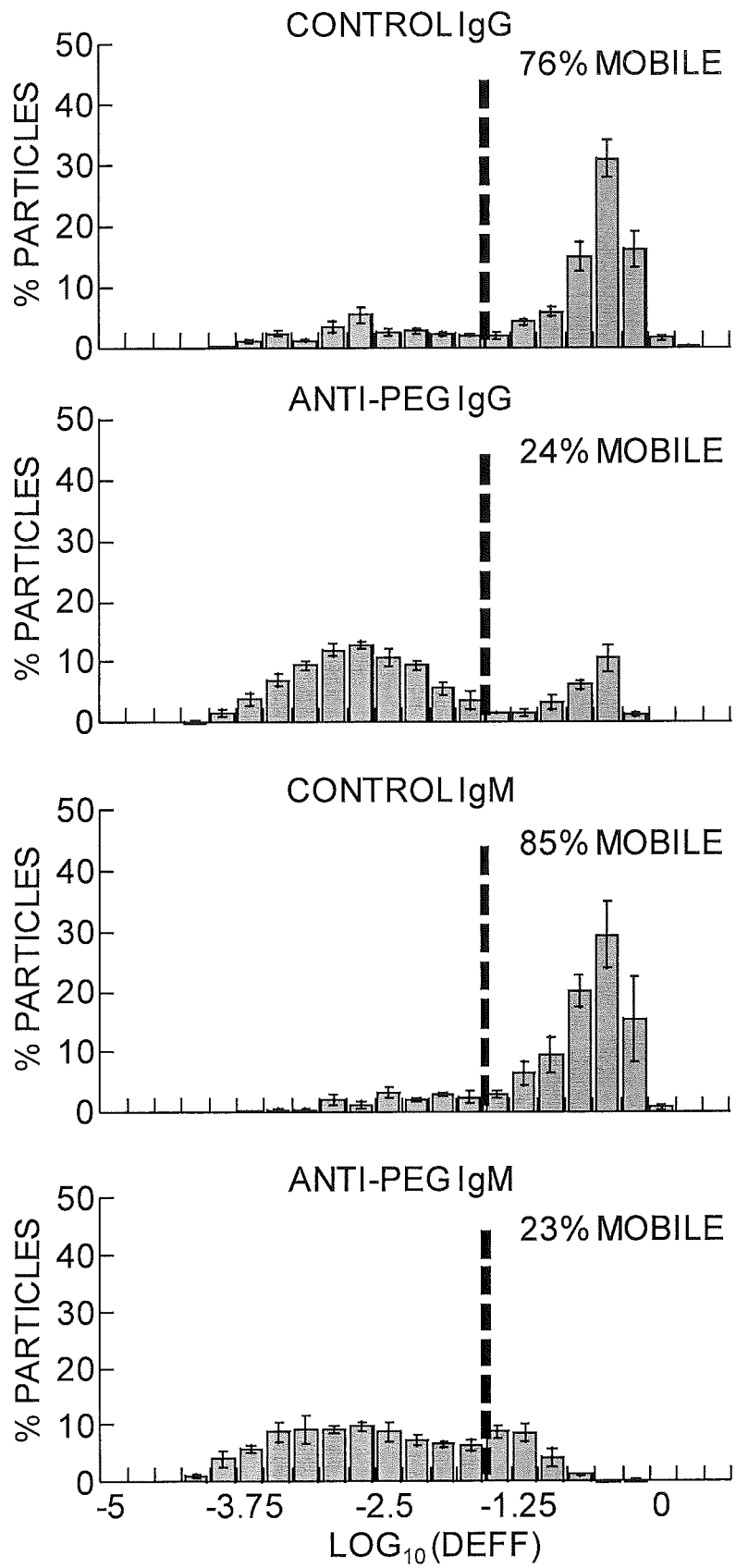
Figure 27C:
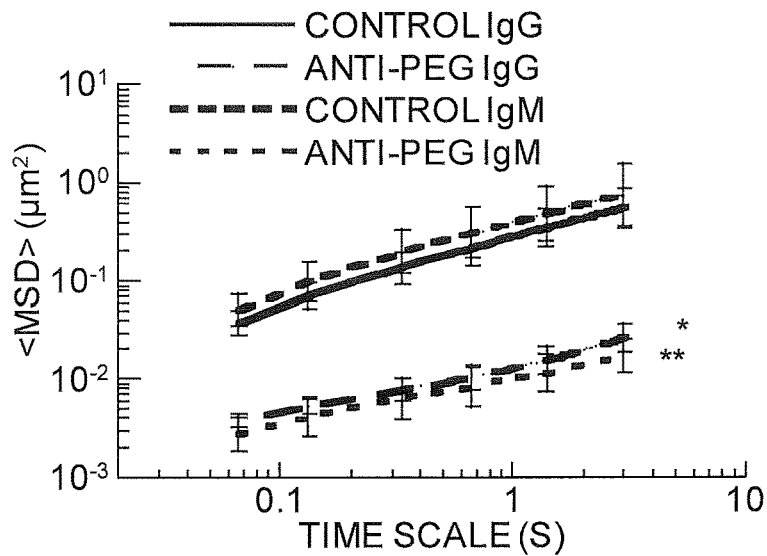
Figure 27D:
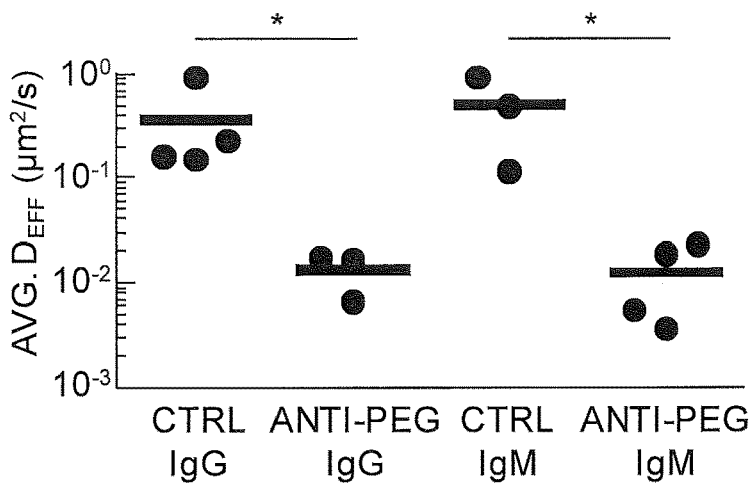
Figure 27E:
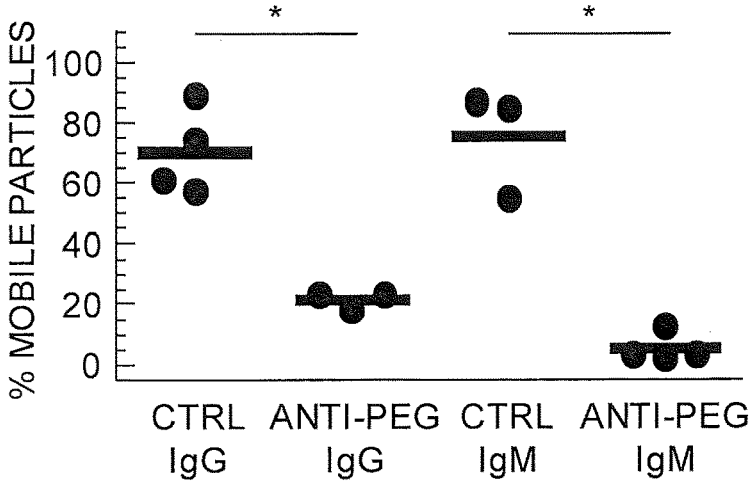

Elucidating the Molecular Basis of Ab-BM Interactions:

We next sought to determine the molecular basis of Ab-BM bonds that facilitate crosslinking of nanoparticles to BM constituents. Since nanoparticle trapping in BM require $F_{ab}$ specificity, we hypothesized that it is the $F_c$-domain, in particular N-glycans on IgG-$F_c$ as well as on the heavy chains of IgM, that mediate binding interactions with BM constituents. To test this hypothesis, we treated anti-PEG IgG and IgM with PNGase F and confirmed that removal of N-glycans did not appreciably alter the binding affinity of either Ab to PEG (FIGS. 22A-22B). In good agreement with our hypothesis, removal of N-glycans from anti-PEG IgG substantially reduced its trapping potency. The fraction of mobile PS-PEG nanoparticles in BM treated with deglycosylated anti-PEG IgG was markedly increased (52±6%) compared to native anti-PEG IgG (21±9%) (p=0.032), consistent with the ~10-fold increase in <MSD> (p<0.0001; FIGS. 26A-276). Similarly, the fraction of mobile PS-PEG beads and their corresponding <MSD> in BM treated with deglycosylated anti-PEG IgM was markedly increased. These results suggest N-glycans on Ab contribute to the association of both IgG and IgM to BM constituents.

Laminin/entactin associate strongly with each other and together represent the largest constituent of BM by mass. To determine the components of BM involved in Ab-mediated trapping, we first studied matrices composed of only laminin/entactin (LAM). Similar to native BM, LAM was able to effectively immobilize PS-COOH but not PS-PEG nanoparticles, confirming the presence of a rigid matrix. We found that anti-PEG IgG and IgM also exhibited comparable trapping potency in LAM. The $<D_{eff}>$ of PS-PEG was reduced ~20-fold and ~40-fold in anti-PEG IgG- and IgM-treated LAM compared to corresponding controls, respectively. Similarly, the fraction of mobile PS-PEG nanoparticles was reduced from 70±7% and 75±10% in LAM mixed with control IgG and IgM to 21±2% and 5±2.5% in LAM mixed with anti-PEG IgG- and IgM, respectively (FIGS. 27A-27E). Since collagen represents another major constituent in BM, we also sought to investigate matrices consisting of purely collagen. However, the collagen-only gel never formed an adequately intact and rigid matrix to immobilize PS-COOH beads, and thus trapping potency was not measured.

Ab-BM Interactions can Prevent Bacterial Translocation:

Finally, as a proof of concept that we can harness Ab to reinforce the barrier properties of BM, as well as demonstrate that Ab-BM bonds are sufficient to immobilize even highly motile bacterial pathogens, we decided to evaluate whether IgG that binds Salmonella typhimurium can prevent the invasion of the bacteria across BM gel. We first added BM and Ab to the upper chamber of transwell system and allowed the gel to form, followed by the addition of fluorescent Salmonella bacteria, and monitored the amount of bacteria found in the bottom chamber. Anti-LPS IgG markedly reduced the flux of Salmonella in native BM in a dose-dependent manner, with >90% reduction in the amount of Salmonella that could penetrate across the BM layer at IgG doses ≥10 μg/mL (FIG. 28). We further investigated matrix composed of LAM only, and found no appreciable difference in the abilities of BM or LAM to prevent Salmonella flux in conjunction with Abs.

Figure 24C:
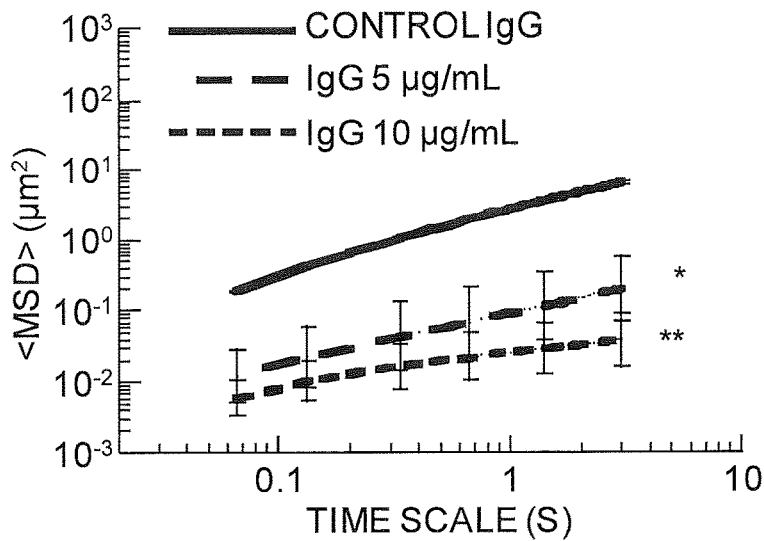
Figure 24D:
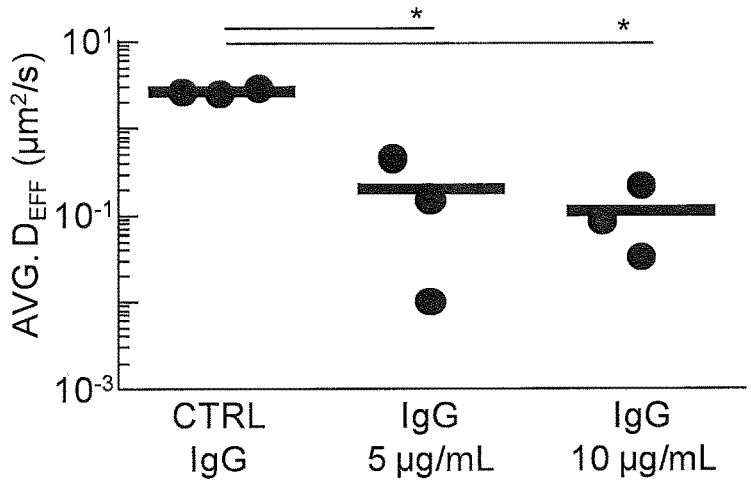
Figure 24E:
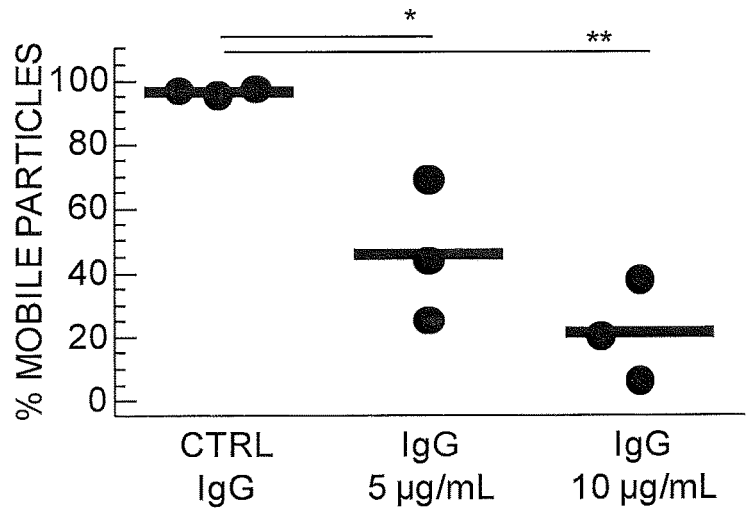

We next assessed whether we can selectively tune the barrier properties of Matrigel® simply by introducing specific antibodies. We mixed in different concentrations of IgG that specifically bind PEG; the antibody possesses weak affinity to collagen and laminin as measured by biolayer interferometry (Table 3). In Matrigel® that contains a final concentration of 10 µg/mL anti-PEG IgG, the $<D_{eff}>$ for PS-PEG was reduced ~167-fold compared to control anti-biotin IgG (FIG. 24D), and the mobile nanoparticle fraction was reduced from 96±0.7% in control IgG to 13±4.2% (p=0.018; FIG. 24E). Anti-PEG IgG enabled substantial trapping of PS-PEG at 5 µg/mL (FIG. 24), but not at 1 µg/mL. The appearance of the PS-PEG nanoparticles remained identical between control IgG and anti-PEG IgG conditions, indicating that the impeded motion of the nanoparticles were not attributed to anti-PEG IgG crosslinking multiple nanoparticles together.

TABLE 3

Binding affinities of anti-PEG IgG and IgM to BLI probes coated with biotinylated collagen or laminin.

| | Collagen | | | Laminin | | |
|---|---|---|---|---|---|---|
| | kon [1/Ms] | Koff [1/s] | KD [M] | kon [1/Ms] | Koff [1/s] | KD [M] |
| IgG | $4.05 \times 10^3$ | $9.49 \times 10^{-4}$ | $2.34 \times 10^{-7}$ | $4.23 \times 10^4$ | $2.98 \times 10^{-4}$ | $7.05 \times 10^{-9}$ |
| IgM | $5.54 \times 10^4$ | $8.79 \times 10^{-4}$ | $1.59 \times 10^{-8}$ | $4.71 \times 10^4$ | $1.77 \times 10^{-4}$ | $3.76 \times 10^{-9}$ |

To further confirm the antigen specificity and ability to reinforce barrier properties against different antigens, we mixed in nanoparticles conjugated with biotin-PEG, and found they were effectively immobilized in Matrigel® treated with anti-biotin IgG (FIGS. 29A-29B). To demonstrate the ability of antigen-specific IgG to mediate trapping even in the presence of large quantities of other crosslinkers, we further evaluated the mobility of PS-PEG in BM simultaneously treated with both 10 µg/mL anti-PEG IgG and 100-fold excess anti-biotin IgG (i.e., 1 mg/mL). We found no appreciable reduction in the trapping potency of anti-PEG IgG despite the excess levels of other antigen-specific IgG (FIGS. 30A-30B). These results underscore antigen-specific IgG can robustly immobilize virus-sized nanoparticles in Matrigel®, and that this strategy can accommodate trapping of a large number of diverse nanoparticle species without compromising the ability to trap any individual foreign species.

Since many antibody-effector functions are influenced by N-glycans on IgG-Fc, not being bound by the theory, it is possible that N-glycans on Fc may also mediate interactions with BM constituents. We deglycosylated anti-PEG IgG and IgM with PNGase F and found that the removal of N-glycans substantially abrogated the trapping potency of IgG and IgM, with the fraction of mobile nanoparticles increasing from 13±4.2% to 57±5.3% for IgG (p=0.0006) and from 13±6.7% to 67±9.4% for IgM (0<0.0001; FIG. 31). Both IgG and IgM antibodies appear to anchor nanoparticles to laminin/entactin (LAM), since we observe comparable trapping with a hydrogel composed of LAM alone: the $<D_{eff}>$ of PS-PEG was reduced ~20-fold and ~40-fold in anti-PEG IgG- and IgM-treated LAM compared to corresponding controls, respectively (FIG. 27).

The foregoing is illustrative of the present invention, and is not to be construed as limiting thereof. The invention is defined by the following claims, with equivalents of the claims to be included therein.

We claim:

1. A method for preventing or treating an infection on a mucosa in a subject, wherein the infection is caused by a respiratory syncytial virus (RSV), said method comprising: administering to the subject in need thereof an effective amount of a population of an antibody against RSV, wherein the antibody in the population has been selected so that the antibody associates with the mucins between 20% to less than 95% of the time, has a rate of binding to the pathogen greater than about $1 \times 10^4$ M$^{-1}$ s$^{-1}$, and has a diffusion coefficient between 20% to 99% less compared to the diffusion coefficient of the antibody in water.

2. The method of claim 1, wherein the antibody has been selected so that the antibody in the population associates with the mucins about 75% of the time and has a diffusion coefficient about 75% less compared to the diffusion coefficient of the antibody in water.

3. The method of claim 1, wherein the mucosa is selected from an oral mucosa, a nasal mucosa, a lung mucosa, a genital mucosa, uterine mucosa, a vaginal mucosa an ocular mucosa and a gastrointestinal mucosa.

4. The method of claim 1, wherein the administering comprises topically administering the antibody to the mucosa of the subject.

5. The method of claim 1, wherein the antibody is formulated into a composition suitable for intranasal, oral, intravaginal, by inhalation, or topical administration to a mucosal surface.

6. The method of claim 5, wherein the composition further comprises a second antibody.

7. The method of claim 1, wherein the antibody binds to a non-neutralizing epitope on the RSV.

8. The method of claim 1, wherein the antibody binds a neutralizing epitope on the RSV.

9. The method of claim 1, wherein the antibody in the population has been selected so that the antibody has a trapping potency at a sub-neutralization dose.

10. A method for preventing or treating an infection on a mucosa in a subject, wherein the infection is caused by a respiratory syncytial virus (RSV), said method comprising: administering to the subject in need thereof an effective amount of a population of an IgM antibody against RSV, wherein the IgM antibody in the population has been selected so that the antibody associates with the mucins between 30% to 85% of the time, has a rate of binding to the pathogen greater than about $1 \times 10^4$ M$^{-1}$ s$^{-1}$, and has a diffusion coefficient between 30% to 85% less compared to the diffusion coefficient of the antibody in water.

11. The method of claim 10, wherein the antibody has been selected so that the antibody in the population associates with the mucins about 75% of the time and has a diffusion coefficient about 75% less compared to the diffusion coefficient of the antibody in water.

12. The method of claim 10, wherein the mucosa is selected from an oral mucosa, a nasal mucosa, a lung mucosa, a genital mucosa, uterine mucosa, a vaginal mucosa an ocular mucosa and a gastrointestinal mucosa.

13. The method of claim 10, wherein the administering comprises topically administering the antibody to the mucosa of the subject.

14. The method of claim 10, wherein the antibody is formulated into a composition suitable for intranasal, oral, intravaginal, by inhalation, or topical administration to a mucosal surface.

15. The method of claim 10, wherein the composition further comprises a second antibody.

16. A method for preventing or treating an infection on a mucosa in a subject, wherein the infection is caused by a pathogen having a mobility of greater than 0.1 $\mu m^2/s$, said method comprising: administering to the subject in need thereof an effective amount of a population of an antibody that specifically binds the pathogen, wherein the antibody has been selected so that the antibody associates with the mucins between 20% to less than 95% of the time, has a rate of binding to the pathogen greater than about $1 \times 10^4 \, M^{-1} \, s^{-1}$, and has a diffusion coefficient between 20% to 99% less compared to the diffusion coefficient of the antibody in water.

17. The method of claim 16, wherein the pathogen comprises one of: respiratory syncytial virus (RSV), influenza, severe acute respiratory syndrome (SARS), parainfluenza, adenovirus, human rhinovirus, coronavirus and norovirus.

* * * * *

UNITED STATES PATENT AND TRADEMARK OFFICE
CERTIFICATE OF CORRECTION

PATENT NO. : 10,793,623 B2  
APPLICATION NO. : 15/977432  
DATED : October 6, 2020  
INVENTOR(S) : Lai et al.

Page 1 of 1

It is certified that error appears in the above-identified patent and that said Letters Patent is hereby corrected as shown below:

In the Specification

Column 9, Line 32: Please correct "Log $D_{off}$" to read -- Log $D_{eff}$ --

Column 33, Line 40: Please correct "$2.5 \times 10^5$ $M^{-1}s^{-1}$" to read -- $2.5 \times 10^5$ $M^{-1}s^{-1}$ --

Column 58, Line 35: Please correct "binding sites is" to read -- binding sites ξ is --

Column 67, Line 44: Please correct "T) – $x(t)]^2$ + $[y(t + \tau) – y(t)]^2$" to read -- $\tau) – x(t)]^2$ + $[y(t + \tau) – y(t)]$ --

Column 68, Line 17: Please correct "104 LB" to read -- 10 μL LB --

Signed and Sealed this  
Ninth Day of March, 2021

Drew Hirshfeld  
*Performing the Functions and Duties of the*  
*Under Secretary of Commerce for Intellectual Property and*  
*Director of the United States Patent and Trademark Office*